(12) United States Patent
Hirayama et al.

(10) Patent No.: US 10,774,083 B2
(45) Date of Patent: Sep. 15, 2020

(54) HETEROCYCLIC AMIDE COMPOUND

(71) Applicant: TAKEDA PHARMACEUTICAL COMPANY LIMITED, Osaka (JP)

(72) Inventors: Takaharu Hirayama, Kanagawa (JP); Yasuhiro Hirata, Kanagawa (JP); Yusuke Tominari, Kanagawa (JP); Naoki Iwamura, Kanagawa (JP); Yusuke Sasaki, Kanagawa (JP); Moriteru Asano, Tokushima (JP); Terufumi Takagi, Kanagawa (JP); Masanori Okaniwa, Cambridge, MA (US); Shinichi Imamura, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/333,296

(22) PCT Filed: Sep. 14, 2017

(86) PCT No.: PCT/JP2017/033213
§ 371 (c)(1),
(2) Date: Mar. 14, 2019

(87) PCT Pub. No.: WO2018/052065
PCT Pub. Date: Mar. 22, 2018

(65) Prior Publication Data
US 2019/0241566 A1 Aug. 8, 2019

(30) Foreign Application Priority Data
Sep. 15, 2016 (JP) ................... 2016-180748

(51) Int. Cl.
*C07D 401/04* (2006.01)
*C07D 401/14* (2006.01)
(Continued)

(52) U.S. Cl.
CPC .......... *C07D 473/28* (2013.01); *A61K 31/437* (2013.01); *A61K 31/444* (2013.01);
(Continued)

(58) Field of Classification Search
CPC ........................... C07D 401/04; C07D 401/14
See application file for complete search history.

(56) References Cited

U.S. PATENT DOCUMENTS

2004/0224981 A1 11/2004 Janjic et al.
2011/0039893 A1 2/2011 Kori et al.
(Continued)

FOREIGN PATENT DOCUMENTS

WO 2008/063669 5/2008
WO 2009/006389 1/2009
WO 2009/006404 1/2009

OTHER PUBLICATIONS

Arita et al. (Biochemical and Biophysical Research Communications, 488, 2017, 648-654).*
(Continued)

*Primary Examiner* — Brian E McDowell
(74) *Attorney, Agent, or Firm* — Wenderoth, Lind & Ponack, L.L.P.

(57) ABSTRACT

Provided is a heterocyclic amide compound that may have a PRS inhibitory action and is expected to be useful as a prophylactic or therapeutic agent for PRS associated diseases and the like including cancer. A compound represented by the following formula (I):

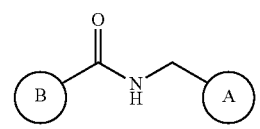

(I)

wherein a group represented by

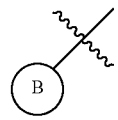

is a group represented by the following formula (II) or the following formula (III):

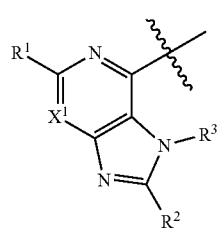

(II)

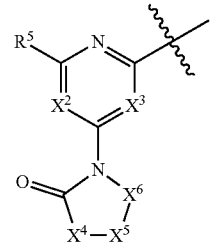

(III)

(Continued)

and other symbols are as described in the DESCRIPTION, or a salt thereof.

5 Claims, No Drawings

Specification includes a Sequence Listing.

(51) Int. Cl.

| | |
|---|---|
| *C07D 473/28* | (2006.01) |
| *C07D 405/14* | (2006.01) |
| *C07D 413/14* | (2006.01) |
| *C07D 409/14* | (2006.01) |
| *C07D 417/14* | (2006.01) |
| *C07D 471/04* | (2006.01) |
| *C07D 473/40* | (2006.01) |
| *C07D 519/00* | (2006.01) |
| *A61P 35/00* | (2006.01) |
| *A61K 31/506* | (2006.01) |
| *A61K 31/444* | (2006.01) |
| *A61K 31/4439* | (2006.01) |
| *C07D 473/00* | (2006.01) |
| *C07D 473/32* | (2006.01) |
| *A61K 31/5377* | (2006.01) |
| *A61K 31/501* | (2006.01) |
| *A61K 31/52* | (2006.01) |
| *A61P 43/00* | (2006.01) |
| *A61K 31/437* | (2006.01) |
| *C12N 9/99* | (2006.01) |

(52) U.S. Cl.
CPC ........ *A61K 31/4439* (2013.01); *A61K 31/501* (2013.01); *A61K 31/506* (2013.01); *A61K 31/52* (2013.01); *A61K 31/5377* (2013.01); *A61P 35/00* (2018.01); *A61P 43/00* (2018.01); *C07D 401/04* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 473/00* (2013.01); *C07D 473/32* (2013.01); *C07D 473/40* (2013.01); *C07D 519/00* (2013.01); *C12N 9/99* (2013.01)

(56) References Cited

U.S. PATENT DOCUMENTS

| | | |
|---|---|---|
| 2011/0263532 A1 | 10/2011 | Keller et al. |
| 2015/0057297 A1 | 2/2015 | Whitman |
| 2016/0159773 A1 | 6/2016 | Saitoh et al. |

OTHER PUBLICATIONS

Jain et al., "Structure of Prolyl-tRNA Synthetase-Halofuginone Complex Provides Basis for Development of Drugs against Malaria and Toxoplasmosis", Structure, vol. 23, pp. 819-829 (2015).

Keller et al., "Halofuginone and other febrifugine derivatives inhibit prolyl-tRNA synthetase", Nature Chemical Biology, vol. 8, pp. 311-317 (2012).

Lamora et al., "Anticancer activity of halofuginone in a preclinical model of osteosarcoma: inhibition of tumor growth and lung metastases", Oncotarget, vol. 6, No. 16, pp. 14413-14427 (2015).

Chen et al., "Halofuginone inhibits colorectal cancer growth through suppression of Akt/mTORC1 signaling and glucose metabolism", vol. 6, No. 27, pp. 24148-24162 (2015).

Kim et al., "Aminoacyl-tRNA synthetases and tumorigenesis: more than housekeeping", Nature Reviews Cancer, vol. 11, pp. 708-718 (2011).

Supplemental European Search Report issued Mar. 10, 2020 in corresponding European Patent Application No. EP 17 85 0966.

Keller et al., "Halofuginone and other febrifugine derivatives inhibit prolyl-tRNA synthetase", Nature Chemical Biology, vol. 8, vol. 3, pp. 311-317 (2012).

\* cited by examiner

HETEROCYCLIC AMIDE COMPOUND

TECHNICAL FIELD

The present invention relates to a heterocyclic amide compound that may have a prolyl-tRNA synthetase (PRS) inhibitory action and is expected to be useful as a prophylactic or therapeutic agent for PRS associated diseases and the like including cancer.

BACKGROUND OF THE INVENTION

As a compound having a PRS inhibitory activity, febrifugine derivatives represented by halofuginone can be mentioned. They were known as antimalarial drugs in the past and application thereof to cancer, fibrosis, inflammatory diseases and the like has been expected in recent years (non-patent documents 1, 2). As for halofuginone, for example, an anti-cancer action against osteosarcoma and colorectal cancer has been reported (non-patent documents 3, 4). PRS is one of the aminoacyl tRNA synthases, involved in the synthesis of proteins, and is suggested to be related to cancer (non-patent document 5).

DOCUMENT LIST

Non-Patent Documents non-patent document 1: Jain V et al., Structure 23, 819-829, May 5, 2015
non-patent document 2: Keller T L et al., Nat Chem Biol. 2012 Feb. 12; 8(3):311-7
non-patent document 3: Lamora A et al., Oncotarget. 2015 Jun. 10; 6(16):14413-27
non-patent document 4: Chen G Q et al., Oncotarget. 2015 Sep. 15; 6(27):24148-62
non-patent document 5: Kim S et al., Nat Rev Cancer. 2011 Sep. 23; 11(10):708-18

SUMMARY OF THE INVENTION

Problems to be Solved by the Invention

An object of the present invention is to provide a novel heterocyclic amide compound that may have a PRS inhibitory action and is expected to be useful as a prophylactic or therapeutic agent for PRS associated diseases and the like including cancer, and a medicament containing same.

Means of Solving the Problems

The present inventors have conducted intensive studies in an attempt to solve the above-mentioned problems and found that a compound represented by the following formula (I) may have a superior PRS inhibitory action, which resulted in the completion of the present invention.

Therefore, the present invention provides the following.
[1] A compound represented by the following formula (I):

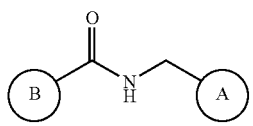

(I)

wherein a group represented by

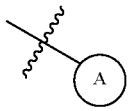

is an optionally substituted aromatic ring group; and a group represented by

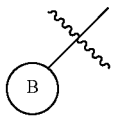

is a group represented by the following formula (II) or the following formula (III):

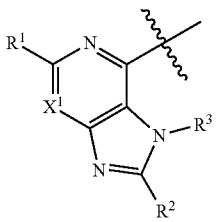

(II)

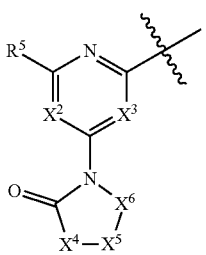

(III)

wherein $R^1$ is a hydrogen atom, a halogen atom, a cyano group, an optionally substituted alkyl group, an optionally substituted cycloalkyl group, an optionally substituted alkenyl group, an optionally substituted alkynyl group, an optionally substituted amino group, or an optionally substituted hydroxy group;

$R^2$ is an optionally substituted hydrocarbon group, or an optionally substituted heterocyclic group;

$R^3$ is a hydrogen atom, an optionally substituted hydrocarbon group, or an optionally substituted heterocyclic group;

$X^1$ is $CR^4$ or a nitrogen atom;

$R^4$ is a hydrogen atom, a halogen atom, or an optionally substituted alkyl group;

$R^5$ is a hydrogen atom, a halogen atom, a cyano group, an optionally substituted alkyl group, an optionally substituted cycloalkyl group, an optionally substituted alkenyl group, an optionally substituted alkynyl group, an optionally substituted amino group, or an optionally substituted hydroxy group;

$X^2$ is $CR^6$ or a nitrogen atom;
$X^3$ is $CR^7$ or a nitrogen atom;
$R^6$ and $R^7$ are each independently a hydrogen atom, a halogen atom, or an optionally substituted alkyl group;

$X^4$ is $CR^8R^9$ or $NR^{10}$, $X^5$ is $CR^{11}R^{12}$ or carbonyl, $X^6$ is $CR^{13}R^{14}$ or an oxygen atom;

$R^8$ and $R^9$ are each independently a hydrogen atom, a cyano group, an optionally substituted hydrocarbon group, or an optionally substituted heterocyclic group;

$R^8$ and $R^9$ are optionally bonded to each other to form, together with the adjacent carbon atom, an optionally further substituted ring;

$R^{10}$, $R^{13}$, and $R^{14}$ are each independently a hydrogen atom, an optionally substituted hydrocarbon group, or an optionally substituted heterocyclic group;

$R^{11}$ and $R^{12}$ are each independently a hydrogen atom, an optionally substituted hydrocarbon group, an optionally substituted heterocyclic group, or an optionally substituted hydroxy group;

or a salt thereof (sometimes to be abbreviated as "compound (I)" in the present specification).

[2] The compound of [1] wherein the group represented by

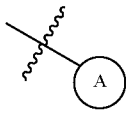

is a $C_{6-14}$ aryl group, a 5- or 6-membered monocyclic aromatic heterocyclic group or a 8 to 14-membered fused polycyclic aromatic heterocyclic group, each of which is optionally substituted by 1 to 5 substituents selected from (1) a halogen atom,
(2) a cyano group,
(3) a $C_{1-6}$ alkyl group optionally substituted by 1 to 3 halogen atoms,
(4) a $C_{6-14}$ aryl group,
(5) a $C_{1-6}$ alkoxy group,
(6) a carboxy group,
(7) a $C_{1-6}$ alkoxy-carbonyl group,
(8) a carbamoyl group optionally mono- or di-substituted by a 5- to 14-membered aromatic heterocyclic group optionally substituted by 1 to 3 $C_{1-6}$ alkyl groups, and
(9) a 5- to 14-membered aromatic heterocyclic group optionally substituted by 1 to 3 substituents selected from
  (i) a cyano group,
  (ii) a $C_{1-6}$ alkyl group optionally substituted by 1 to 3 substituents selected from a halogen atom, a hydroxy group and a 3- to 14-membered non-aromatic heterocyclic group,
  (iii) a $C_{3-10}$ cycloalkyl group,
  (iv) a $C_{1-6}$ alkoxy group,
  (v) an oxo group,
  (vi) a $C_{1-6}$ alkoxy-carbonyl group and
  (vii) a 3- to 14-membered non-aromatic heterocyclic group;
the group represented by

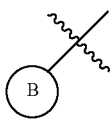

is (1) a group represented by the following formula (II):

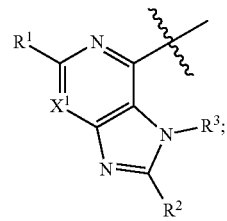

(II)

$R^1$ is a hydrogen atom, a halogen atom, a cyano group, an alkyl group, an amino group optionally mono- or di-substituted by a $C_{1-6}$ alkyl group, or a hydroxy group optionally substituted by a $C_{1-6}$ alkyl group;

$R^2$ is
(1) a $C_{1-6}$ alkyl group optionally substituted by 1 to 3 substituents selected from a $C_{3-10}$ cycloalkyl group and a $C_{6-14}$ aryl group,
(2) a $C_{3-10}$ cycloalkyl group optionally substituted by 1 to 3 substituents selected from a halogen atom, a hydroxy group and a $C_{1-6}$ alkyl group, or
(3) a 3- to 14-membered non-aromatic heterocyclic group optionally substituted by 1 to 3 oxo groups;

$R^3$ is
(1) a hydrogen atom,
(2) a $C_{1-6}$ alkyl group optionally substituted by 1 to 3 substituents selected from
  (i) a cyano group,
  (ii) a hydroxy group,
  (iii) a $C_{3-10}$ cycloalkyl group,
  (iv) a $C_{6-14}$ aryl group,
  (v) a $C_{7-16}$ aralkyloxy group,
  (vi) a carboxy group and
  (vii) a carbamoyl group optionally mono- or di-substituted by a $C_{1-6}$ alkyl group or
(3) a $C_{3-10}$ cycloalkyl group;

$X^1$ is $CR^4$ ($R^4$ is a hydrogen atom or a fluorine atom) or a nitrogen atom; or (2) a group represented by the following formula (III):

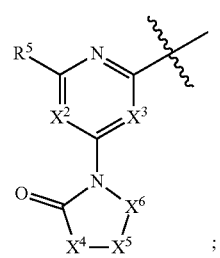

(III)

$R^5$ is a hydrogen atom, a $C_{1-6}$ alkyl group optionally substituted by 1 to 3 halogen atoms, a cycloalkyl group, or a hydroxy group optionally substituted by a $C_{1-6}$ alkyl group;

$X^2$ is $CR^6$ ($R^6$ is a hydrogen atom) or a nitrogen atom;
$X^3$ is $CR^7$ ($R^7$ is a hydrogen atom) or a nitrogen atom;
$X^4$ is $CR^8R^9$ ($R^8$ and $R^9$ are each independently
(1) a hydrogen atom,
(2) a cyano group, (3) a $C_{1-6}$ alkyl group optionally substituted by 1 to 3 substituents selected from a hydroxy group and a $C_{3-10}$ cycloalkyl group or (4) a $C_{3-10}$ cycloalkyl group optionally substituted by 1 to 3 $C_{1-6}$ alkyl groups, or $R^8$ and $R^9$ are bonded to each other to form $C_{3-10}$ cycloalkane together with the adjacent carbon atom) or $NR^{10}$ ($R^{10}$ is a $C_{1-6}$ alkyl group);

$X^5$ is $CR^{11}R^{12}$ ($R^{11}$ and $R^{12}$ are each independently a hydrogen atom or a hydroxy group) or a carbonyl; and $X^6$ is $CR^{13}R^{14}$ ($R^{13}$ and $R^{14}$ are each independently a hydrogen atom or a $C_{1-6}$ alkyl group) or an oxygen atom; or a salt thereof.

[3] A medicament comprising the compound of [1] or a salt thereof.

[4] The medicament of [3] which is a PRS inhibitor.

[5] The medicament of [3] which is a prophylactic or therapeutic agent for cancer.

[6] The compound of [1] or a salt thereof which is used for the prophylaxis or treatment of cancer.

[7] A method for inhibiting PRS in a mammal, comprising administering an effective amount of the compound of [1] or a salt thereof to the mammal.

[8] A method for preventing or treating cancer in a mammal, comprising administering an effective amount of the compound of [1] or a salt thereof to the mammal.

[9] Use of the compound of [1] or a salt thereof for producing a prophylactic or therapeutic agent for cancer.

Effect of the Invention

According to the present invention, a heterocyclic amide compound that may have a PRS inhibitory action and is expected to be useful as a prophylactic or therapeutic agent for PRS associated diseases and the like including cancer, and a medicament containing same are provided.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$-alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,

(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and
8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxycarbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include "an amino group optionally having" 1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-16}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$-alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "aromatic ring group" of the "optionally substituted aromatic ring group" include the above-mentioned "$C_{6-14}$ aryl group" and "aromatic heterocyclic group", and examples of the substituent thereof include the above-mentioned "substituent".

In the present specification, examples of the "ring" of the "optionally further substituted ring" include the above-mentioned "hydrocarbon ring" and the above-mentioned "heterocycle", and examples of the substituent thereof include the above-mentioned "substituent".

The definition of each symbol in the formula (I) is explained below.

The group represented by

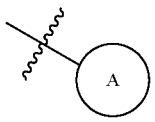

(hereinafter sometimes to be referred to as "ring A group" for simplification) is an optionally substituted aromatic ring group;

a group represented by

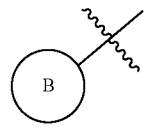

(hereinafter sometimes to be referred to as "ring B group" for simplification) is a group represented by the following formula (II) or the following formula (III):

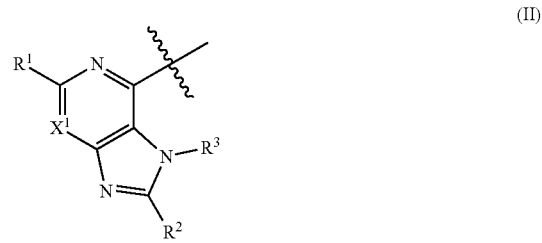

(II)

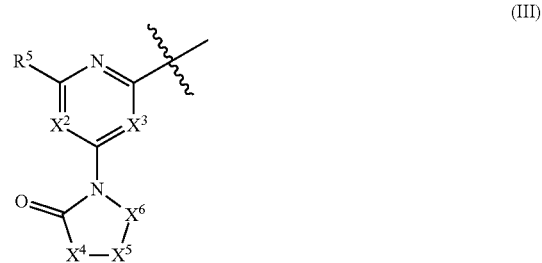

(III)

wherein $R^1$ is a hydrogen atom, a halogen atom, a cyano group, an optionally substituted alkyl group, an optionally substituted cycloalkyl group, an optionally substituted alkenyl group, an optionally substituted alkynyl group, an optionally substituted amino group, or an optionally substituted hydroxy group;
$R^2$ is an optionally substituted hydrocarbon group, or an optionally substituted heterocyclic group;
$R^3$ is a hydrogen atom, an optionally substituted hydrocarbon group, or an optionally substituted heterocyclic group;
$X^1$ is $CR^4$ or a nitrogen atom;
$R^4$ is a hydrogen atom, a halogen atom, or an optionally substituted alkyl group;
wherein $R^5$ is a hydrogen atom, a halogen atom, a cyano group, an optionally substituted alkyl group, an optionally substituted cycloalkyl group, an optionally substituted alkenyl group, an optionally substituted alkynyl group, an optionally substituted amino group, or an optionally substituted hydroxy group;
$X^2$ is $CR^6$ or a nitrogen atom;
$X^3$ is $CR^7$ or a nitrogen atom;
$R^6$ and $R^7$ are each independently a hydrogen atom, a halogen atom, or an optionally substituted alkyl group;
$X^4$ is $CR^8R^9$ or $NR^{10}$, $X^5$ is $CR^{11}R^{12}$ or carbonyl, $X^6$ is $CR^{13}R^{14}$ or an oxygen atom;
$R^8$ and $R^9$ are each independently a hydrogen atom, a cyano group, an optionally substituted hydrocarbon group, or an optionally substituted heterocyclic group;
$R^8$ and $R^9$ are optionally bonded to each other to form, together with the adjacent carbon atom, an optionally further substituted ring;
$R^{10}$, $R^{12}$, $R^{13}$, and $R^{14}$ are each independently a hydrogen atom, an optionally substituted hydrocarbon group, or an optionally substituted heterocyclic group;

$R^{11}$ and $R^{12}$ are each independently a hydrogen atom, an optionally substituted hydrocarbon group, an optionally substituted heterocyclic group, or an optionally substituted hydroxy group.

(1) When Ring B Group is a Group Represented by the Formula (II):

The "aromatic ring group" of the "optionally substituted aromatic ring group" for ring A group is preferably a $C_{6-14}$ aryl group (e.g., phenyl) or an aromatic heterocyclic group (pyridyl, pyrimidinyl, indazolyl, pyrazolopyridyl, imidazopyridyl, benzimidazolyl), more preferably, a $C_{6-14}$ aryl group (e.g., phenyl), a 5- or 6-membered monocyclic aromatic heterocyclic group (e.g., pyridyl, pyrimidinyl) or a 8- to 14-membered fused polycyclic (preferably bicyclic or tricyclic) aromatic heterocyclic group (e.g., indazolyl, pyrazolopyridyl, imidazopyridyl, benzimidazolyl), further preferably phenyl.

The "aromatic ring group" of the "optionally substituted aromatic ring group" for ring A group is optionally substituted by 1 to 5 (preferably 1 to 3, more preferably 1 or 2) substituents other than —CO—NH—CH$_2$— group at substitutable position(s). Examples of such substituent include the above-mentioned "substituent", preferably, (1) a halogen atom (e.g., fluorine atom, chlorine atom, bromine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) a carboxy group, (7) an optionally substituted $C_{1-6}$ alkoxy-carbonyl group (e.g., methoxycarbonyl), (8) an optionally substituted carbamoyl group, or (9) an optionally substituted 5- to 14-membered aromatic heterocyclic group (e.g., pyrazolyl, imidazolyl, triazolyl, pyridyl, pyridazinyl), more preferably, (1) a halogen atom (e.g., fluorine atom, chlorine atom, bromine atom), (2) a cyano group, (3) a $C_{1-6}$ alkyl group (e.g., methyl), (4) a $C_{6-14}$ aryl group (e.g., phenyl), (5) a $C_{1-6}$ alkoxy group (e.g., methoxy), (6) a carboxy group, (7) a $C_{1-6}$ alkoxy-carbonyl group (e.g., methoxycarbonyl), (8) a carbamoyl group optionally mono- or di-substituted by a 5- to 14-membered aromatic heterocyclic group (e.g., pyrazolyl) optionally substituted by 1 to 3 $C_{1-6}$ alkyl groups (e.g., methyl), or (9) a 5- to 14-membered aromatic heterocyclic group (e.g., pyrazolyl, imidazolyl, triazolyl, pyridyl, pyridazinyl) optionally substituted by 1 to 3 substituents selected from (i) a cyano group, (ii) a $C_{1-6}$ alkyl group (e.g., methyl, ethyl, isopropyl, tert-butyl) optionally substituted by 1 to 3 substituents selected from a halogen atom (e.g., fluorine atom) and a hydroxy group, (iii) a $C_{3-10}$ cycloalkyl group (e.g., cyclopropyl), (iv) a $C_{1-6}$ alkoxy group (e.g., methoxy) and (v) an oxo group, further preferably, (1) a halogen atom (e.g., fluorine atom), (2) a cyano group, or (3) a 5- to 14-membered aromatic heterocyclic group (e.g., pyrazolyl) optionally substituted by 1 to 3 $C_{1-6}$ alkyl groups (e.g., methyl), particularly preferably, (1) a halogen atom (e.g., fluorine atom), or (2) a 5- to 14-membered aromatic heterocyclic group (e.g., pyrazolyl) optionally substituted by 1 to 3 $C_{1-6}$ alkyl groups (e.g., methyl).

Ring A group is preferably a $C_{6-14}$ aryl group (e.g., phenyl) or an aromatic heterocyclic group (pyridyl, pyrimidinyl, benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) a carboxy group, (7) an optionally substituted $C_{1-6}$ alkoxy-carbonyl group (e.g., methoxycarbonyl), (8) an optionally substituted carbamoyl group, and (9) an optionally substituted 5- to 14-membered aromatic heterocyclic group (e.g., pyrazolyl, imidazolyl, triazolyl, pyridyl, pyridazinyl), more preferably a $C_{6-14}$ aryl group (e.g., phenyl), a 5- or 6-membered monocyclic aromatic heterocyclic group (e.g., pyridyl, pyrimidinyl) or a 8- to 14-membered fused polycyclic (preferably bicyclic or tricyclic) aromatic heterocyclic group (e.g., benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) a $C_{1-6}$ alkyl group (e.g., methyl), (4) a $C_{6-14}$ aryl group (e.g., phenyl), (5) a $C_{1-6}$ alkoxy group (e.g., methoxy), (6) a carboxy group, (7) a $C_{1-6}$ alkoxy-carbonyl group (e.g., methoxycarbonyl), (8) a carbamoyl group optionally mono- or di-substituted by a 5- to 14-membered aromatic heterocyclic group (e.g., pyrazolyl) optionally substituted by 1 to 3 $C_{1-6}$ alkyl groups (e.g., methyl), or (9) a 5- to 14-membered aromatic heterocyclic group (e.g., pyrazolyl, imidazolyl, triazolyl, pyridyl, pyridazinyl) optionally substituted by 1 to 3 substituents selected from (i) a cyano group, (ii) a $C_{1-6}$ alkyl group (e.g., methyl, ethyl, isopropyl, tert-butyl) optionally substituted by 1 to 3 substituents selected from a halogen atom (e.g., fluorine atom) and a hydroxy group, (iii) a $C_{3-10}$ cycloalkyl group (e.g., cyclopropyl), (iv) a $C_{1-6}$ alkoxy group (e.g., methoxy) and (v) an oxo group, further preferably phenyl optionally substituted by 1 to 5 (preferably 1 to 3, more preferably 1 or 2) substituents selected from (1) a halogen atom (e.g., fluorine atom), (2) a cyano group, and (3) a 5- to 14-membered aromatic heterocyclic group (e.g., pyrazolyl) optionally substituted by 1 to 3 $C_{1-6}$ alkyl groups (e.g., methyl), particularly preferably phenyl optionally substituted by 1 to 5 (preferably 1 to 3, more preferably 1 or 2) substituents selected from (1) a halogen atom (e.g., fluorine atom), and (2) a 5- to 14-membered aromatic heterocyclic group (e.g., pyrazolyl) optionally substituted 1 to 3 $C_{1-6}$ alkyl groups (e.g., methyl).

$R^1$ is preferably a hydrogen atom, a halogen atom (e.g., chlorine atom), a cyano group, an optionally substituted alkyl group (e.g., methyl), an optionally substituted amino group, or an optionally substituted hydroxy group, more preferably a hydrogen atom, a halogen atom (e.g., chlorine atom), a cyano group, an alkyl group (e.g., methyl), an amino group optionally mono- or di-substituted by a $C_{1-6}$ alkyl group (e.g., methyl), or a hydroxy group optionally substituted by a $C_{1-6}$ alkyl group (e.g., methyl), further preferably a hydrogen atom.

The "hydrocarbon group" of the "optionally substituted hydrocarbon group" for $R^2$ is preferably a $C_{1-6}$ alkyl group (e.g., methyl, ethyl, isopropyl) or a $C_{3-10}$ cycloalkyl group (e.g., cyclopropyl, cyclobutyl, cyclopentyl, bicyclo[1.1.1]pentyl), and the substituent thereof is preferably a halogen atom (e.g., fluorine atom), a hydroxy group, a $C_{1-6}$ alkyl group (e.g., methyl), a $C_{3-10}$ cycloalkyl group (e.g., cyclopropyl, cyclopentyl) or a $C_{6-14}$ aryl group (e.g., phenyl).

The "heterocyclic group" of the "optionally substituted heterocyclic group" for $R^2$ is preferably a 3- to 14-membered non-aromatic heterocyclic group (e.g., tetrahydrofuranyl, tetrahydropyranyl, 1,4-dioxanyl, tetrahydrothienyl), and the substituent thereof is preferably an oxo group.

$R^2$ is preferably an optionally substituted $C_{1-6}$ alkyl group (e.g., methyl, ethyl, isopropyl), an optionally substituted $C_{3-10}$ cycloalkyl group (e.g., cyclopropyl, cyclobutyl, cyclopentyl, bicyclo[1.1.1]pentyl) or an optionally substituted 3- to 14-membered non-aromatic heterocyclic group (e.g., tetrahydrofuranyl, tetrahydropyranyl, 1,4-dioxanyl, tetrahydrothienyl), more preferably (1) a $C_{1-6}$ alkyl group (e.g., methyl, ethyl, isopropyl) optionally substituted by 1 to 3 substituents selected from a $C_{3-10}$ cycloalkyl group (e.g., cyclopropyl, cyclopentyl) and a $C_{6-14}$ aryl group (e.g., phenyl), (2) a $C_{3-10}$ cycloalkyl group (e.g., cyclopropyl, cyclobutyl, cyclopentyl, bicyclo[1.1.1]pentyl) optionally substituted by 1 to 3 substituents selected from a halogen atom (e.g., fluorine atom), a hydroxy group and a $C_{1-6}$ alkyl group (e.g., methyl), or (3) a 3- to 14-membered non-aromatic heterocyclic group (e.g., tetrahydrofuranyl, tetrahydropyranyl, 1,4-dioxanyl, tetrahydrothienyl) optionally substituted by 1 to 3 oxo groups, further preferably a $C_{3-10}$ cycloalkyl group (e.g., cyclopentyl) or a 3- to 14-membered non-aromatic heterocyclic group (e.g., tetrahydrofuranyl, tetrahydropyranyl, 1,4-dioxanyl), particularly preferably a 3- to 14-membered non-aromatic heterocyclic group (e.g., 1,4-dioxanyl).

The "hydrocarbon group" of the "optionally substituted hydrocarbon group" for $R^3$ is preferably a $C_{1-6}$ alkyl group (e.g., methyl, ethyl) or a $C_{3-10}$ cycloalkyl group (e.g., cyclopropyl), and the substituent thereof is preferably a cyano group, a hydroxy group, a $C_{3-10}$ cycloalkyl group (e.g., cyclopropyl), a $C_{6-14}$ aryl group (e.g., phenyl), a $C_{7-16}$ aralkyloxy group (e.g., benzyloxy), a carboxy group or an optionally substituted carbamoyl group.

$R^3$ is preferably a hydrogen atom, an optionally substituted $C_{1-6}$ alkyl group (e.g., methyl, ethyl) or an optionally substituted $C_{3-10}$ cycloalkyl group (e.g., cyclopropyl), more preferably (1) a hydrogen atom, (2) a $C_{1-6}$ alkyl group (e.g., methyl, ethyl) optionally substituted by 1 to 3 substituents selected from (i) a cyano group, (ii) a hydroxy group, (iii) a $C_{3-10}$ cycloalkyl group (e.g., cyclopropyl), (iv) a $C_{6-14}$ aryl group (e.g., phenyl), (v) a $C_{7-16}$ aralkyloxy group (e.g., benzyloxy), (vi) a carboxy group and (vii) a carbamoyl group optionally mono- or di-substituted by a $C_{1-6}$ alkyl group (e.g., methyl) or (3) a $C_{3-10}$ cycloalkyl group (e.g., cyclopropyl), further preferably a hydrogen atom or a $C_{1-6}$ alkyl group (e.g., methyl), particularly preferably a hydrogen atom.

$X^1$ is preferably $CR^4$ ($R^4$ is a hydrogen atom or a halogen atom (e.g., fluorine atom)) or a nitrogen atom, more preferably $CR^4$ ($R^4$ is a hydrogen atom or a fluorine atom) or a nitrogen atom, further preferably a nitrogen atom.

(2) When Ring B Group is a Group Represented by the Formula (III):

The "aromatic ring group" of the "optionally substituted aromatic ring group" for ring A group is preferably a $C_{6-14}$ aryl group (e.g., phenyl) or an aromatic heterocyclic group (thienyl), more preferably a $C_{6-14}$ aryl group (e.g., phenyl) or a 5- or 6-membered monocyclic aromatic heterocyclic group (e.g., thienyl), further preferably phenyl.

The "aromatic ring group" of the "optionally substituted aromatic ring group" for ring A group is optionally substituted by 1 to 5 (preferably 1 to 3, more preferably 1 or 2) substituents other than —CO—NH—CH$_2$— group at substitutable position(s). Examples of such substituent include the above-mentioned "substituent", preferably, (1) a halogen atom (e.g., fluorine atom, chlorine atom, bromine atom), (2) a cyano group, (3) an optionally substituted $C_{1-6}$ alkyl group (e.g., methyl), or (4) an optionally substituted 5- to 14-membered aromatic heterocyclic group (e.g., pyrazolyl, imidazolyl, triazolyl, thiazolyl, pyridyl, pyrimidinyl, pyridazinyl), more preferably, (1) a halogen atom (e.g., fluorine atom, chlorine atom, bromine atom), (2) a cyano group, (3) a $C_{1-6}$ alkyl group (e.g., methyl) optionally substituted by 1 to 3 halogen atoms (e.g., fluorine atom), or (4) a 5- to 14-membered aromatic heterocyclic group (e.g., pyrazolyl, imidazolyl, triazolyl, thiazolyl, pyridyl, pyrimidinyl, pyridazinyl) optionally substituted by 1 to 3 substituents selected from (i) a halogen atom (e.g., fluorine atom), (ii) a $C_{1-6}$ alkyl group (e.g., methyl, ethyl, isopropyl, tert-butyl) optionally substituted by 1 to 3 substituents selected from a halogen atom (e.g., fluorine atom), a hydroxy group and a 3- to 14-membered non-aromatic heterocyclic group (e.g., morpholinyl), (iii) a $C_{3-10}$ cycloalkyl group (e.g., cyclopropyl), (iv) a $C_{1-6}$ alkoxy group (e.g., methoxy), (v) an oxo group, (vi) a $C_{1-6}$ alkoxy-carbonyl group (e.g., tert-butoxycarbonyl) and (vii) a 3- to 14-membered non-aromatic heterocyclic group (e.g., tetrahydropyranyl), further preferably (1) a halogen atom (e.g., fluorine atom) or (2) a 5- to 14-membered aromatic heterocyclic group (e.g., pyrazolyl) optionally substituted by 1 to 3 substituents selected from a $C_{1-6}$ alkyl group (e.g., methyl) and a $C_{3-10}$ cycloalkyl group (e.g., cyclopropyl), particularly preferably (1) a halogen atom (e.g., fluorine atom) or (2) a 5- to 14-membered aromatic heterocyclic group (e.g., pyrazolyl) optionally substituted by 1 to 3 $C_{1-6}$ alkyl groups (e.g., methyl).

Ring A group is preferably a $C_{6-14}$ aryl group (e.g., phenyl) or an aromatic heterocyclic group (thienyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) an optionally substituted $C_{1-6}$ alkyl group (e.g., methyl), and (4) an optionally substituted 5- to 14-membered aromatic heterocyclic group (e.g., pyrazolyl, imidazolyl, triazolyl, thiazolyl, pyridyl, pyrimidinyl, pyridazinyl), more preferably, a $C_{6-14}$ aryl group (e.g., phenyl) or a 5- or 6-membered monocyclic aromatic heterocyclic group (e.g., thienyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) a $C_{1-6}$ alkyl group (e.g., methyl) optionally substituted by 1 to 3 halogen atoms (e.g., fluorine atom) and (4) a 5- to 14-membered aromatic heterocyclic group (e.g., pyrazolyl, imidazolyl, triazolyl, thiazolyl, pyridyl, pyrimidinyl, pyridazinyl) optionally substituted by 1 to 3 substituents selected from (i) a halogen atom (e.g., fluorine atom), (ii) a $C_{1-6}$ alkyl group (e.g., methyl, ethyl, isopropyl, tert-butyl) optionally substituted by 1 to 3 substituents selected from a halogen atom (e.g., fluorine atom), a hydroxy group and a 3- to 14-membered non-aromatic heterocyclic group (e.g., morpholinyl), (iii) a $C_{3-10}$ cycloalkyl group (e.g., cyclopropyl), (iv) a $C_{1-6}$ alkoxy group (e.g., methoxy), (v) an oxo group, (vi) a $C_{1-6}$ alkoxy-carbonyl group (e.g., tert-butoxycarbonyl) and (vii) a 3- to 14-membered non-aromatic heterocyclic group (e.g., tetrahydropyranyl), further preferably phenyl optionally substituted by 1 to 5 (preferably 1 to 3, more preferably 1 or 2) substituents selected from (1) a halogen atom (e.g., fluorine atom), and (2) a 5- to 14-membered aromatic heterocyclic group (e.g., pyrazolyl) optionally substituted by to 3 substituents selected from a $C_{1-6}$ alkyl group (e.g., methyl) and a $C_{3-10}$ cycloalkyl group (e.g., cyclopropyl), particularly preferably phenyl optionally substituted by 1 to 5 (preferably 1 to 3, more preferably 1 or 2) substituents selected from (1) a halogen atom (e.g., fluorine atom), and (2) a 5- to 14-membered aromatic heterocyclic group (e.g., pyrazolyl) optionally substituted by 1 to 3 $C_{1-6}$ alkyl groups (e.g., methyl).

$R^5$ is preferably a hydrogen atom, an optionally substituted alkyl group (e.g., methyl, ethyl), an optionally substituted cycloalkyl group (e.g., cyclopropyl), or an optionally substituted hydroxy group, more preferably a hydrogen atom, a $C_{1-6}$ alkyl group (e.g., methyl, ethyl) optionally substituted by 1 to 3 halogen atoms (e.g., fluorine atom), a cycloalkyl group (e.g., cyclopropyl), or a hydroxy group optionally substituted by a $C_{1-6}$ alkyl group (e.g., methyl), further preferably a $C_{1-6}$ alkyl group (e.g., methyl).

$X^2$ is preferably CH or a nitrogen atom, more preferably CH.

$X^3$ is preferably CH or a nitrogen atom, more preferably CH.

The "hydrocarbon group" of the "optionally substituted hydrocarbon group" for $R^8$ or $R^9$ is preferably a $C_{1-6}$ alkyl group (e.g., methyl, ethyl, tert-butyl) or a $C_{3-10}$ cycloalkyl group (e.g., cyclopropyl, cyclobutyl), and the substituent thereof is preferably a hydroxy group, a $C_{1-6}$ alkyl group (e.g., methyl) or a $C_{3-10}$ cycloalkyl group (e.g., cyclopropyl).

The "ring" of the "optionally further substituted ring" formed by $R^8$ and $R^9$, which are bonded to each other, together with the adjacent carbon atom is preferably $C_{3-10}$ cycloalkane (e.g., cyclopropane, cyclobutane).

The "hydrocarbon group" of the "optionally substituted hydrocarbon group" for $R^{10}$ is preferably a $C_{1-6}$ alkyl group (e.g., isopropyl).

$X^4$ is preferably $CR^6R^9$ ($R^8$ and $R^9$ are each independently a hydrogen atom, a cyano group, an optionally substituted $C_{1-6}$ alkyl group (e.g., methyl, ethyl, tert-butyl) or an optionally substituted $C_{3-10}$ cycloalkyl group (e.g., cyclopropyl, cyclobutyl), or $R^8$ and $R^9$ may be bonded to each other to form, together with the adjacent carbon atom, an optionally further substituted $C_{3-10}$ cycloalkane (e.g., cyclopropane, cyclobutane)) or $NR^{10}$ ($R^{10}$ is an optionally substituted $C_{1-6}$ alkyl group (e.g., isopropyl)), more preferably $CR^8R^9$ ($R^8$ and $R^9$ are each independently (1) a hydrogen atom, (2) a cyano group, (3) a $C_{1-6}$ alkyl group (e.g., methyl, ethyl, tert-butyl) optionally substituted by 1 to 3 substituents selected from a hydroxy group and a $C_{3-10}$ cycloalkyl group (e.g., cyclopropyl) or (4) a $C_{3-10}$ cycloalkyl group (e.g., cyclopropyl, cyclobutyl) optionally substituted by 1 to 3 $C_{1-6}$ alkyl groups (e.g., methyl), or $R^8$ and $R^9$ may be bonded to each other to form, together with the adjacent carbon atom, $C_{3-10}$ cycloalkane (e.g., cyclopropane, cyclobutane)) or $NR^{10}$ ($R^{10}$ is a $C_{1-6}$ alkyl group (e.g., isopropyl)), further preferably $CR^8R^9$ ($R^8$ and $R^9$ are each independently a cyano group or a $C_{3-10}$ cycloalkyl group (e.g., cyclopropyl)).

$X^5$ is preferably $CR^{11}R^{12}$ ($R^{11}$ and $R^{12}$ are each independently a hydrogen atom or an optionally substituted hydroxy group) or carbonyl, more preferably $CR^{11}R^{12}$ ($R^{11}$ and $R^{12}$ are each independently a hydrogen atom or a hydroxy group) or carbonyl, further preferably $CH_2$.

In another embodiment of the present invention, a compound wherein $X^5$ is $CH_2$ is preferable.

The "hydrocarbon group" of the "optionally substituted hydrocarbon group" for $R^{13}$ or $R^{14}$ is preferably a $C_{1-6}$ alkyl group (e.g., methyl).

$X^6$ is preferably $CR^{13}R^{14}$ ($R^{13}$ and $R^{14}$ are each independently a hydrogen atom or an optionally substituted $C_{1-6}$ alkyl group (e.g., methyl)) or an oxygen atom, more preferably $CR^{13}R^{14}$ ($R^{13}$ and $R^{14}$ are each independently a hydrogen atom or a $C_{1-6}$ alkyl group (e.g., methyl)) or an oxygen atom, further preferably $CH_2$.

Preferable examples of compound (I) include the following compounds.

[Compound A]

Compound (I) wherein ring A group is a $C_{6-14}$ aryl group (e.g., phenyl) or an aromatic heterocyclic group (thienyl, pyridyl, pyrimidinyl, benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) a carboxy group, (7) an optionally substituted $C_{1-6}$ alkoxy-carbonyl group (e.g., methoxycarbonyl), (8) an optionally substituted carbamoyl group, and (9) an optionally substituted 5- to 14-membered aromatic heterocyclic group (e.g., pyrazolyl, imidazolyl, triazolyl, thiazolyl, pyridyl, pyrimidinyl, pyridazinyl);

ring B group is (1) A Group Represented by the Formula (II);

$R^1$ is a hydrogen atom, a halogen atom (e.g., chlorine atom), a cyano group, an optionally substituted alkyl group (e.g., methyl), an optionally substituted amino group, or an optionally substituted hydroxy group;

$R^2$ is an optionally substituted $C_{1-6}$ alkyl group (e.g., methyl, ethyl, isopropyl), an optionally substituted $C_{3-10}$ cycloalkyl group (e.g., cyclopropyl, cyclobutyl, cyclopentyl, bicyclo[1.1.1]pentyl) or an optionally substituted 3- to 14-membered non-aromatic heterocyclic group (e.g., tetrahydrofuranyl, tetrahydropyranyl, 1,4-dioxanyl, tetrahydrothienyl);

$R^3$ is a hydrogen atom, an optionally substituted $C_{1-6}$ alkyl group (e.g., methyl, ethyl) or an optionally substituted $C_{3-10}$ cycloalkyl group (e.g., cyclopropyl);

$X^1$ is $CR^4$ ($R^4$ is a hydrogen atom or a halogen atom (e.g., fluorine atom)) or a nitrogen atom; or (2) a group represented by the formula (III);

$R^5$ is a hydrogen atom, an optionally substituted alkyl group (e.g., methyl, ethyl), an optionally substituted cycloalkyl group (e.g., cyclopropyl), or an optionally substituted hydroxy group;

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently a hydrogen atom, a cyano group, an optionally substituted $C_{1-6}$ alkyl group (e.g., methyl, ethyl, tert-butyl) or an optionally substituted $C_{3-10}$ cycloalkyl group (e.g., cyclopropyl, cyclobutyl), or $R^8$ and $R^9$ may be bonded to each other to form, together with the adjacent carbon atom, an optionally further substituted $C_{3-10}$ cycloalkane (e.g., cyclopropane, cyclobutane)) or $NR^{10}$ ($R^{10}$ is an optionally substituted $C_{1-6}$ alkyl group (e.g., isopropyl));

$X^5$ is $CR^{11}R^{12}$ ($R^{11}$ and $R^{12}$ are each independently a hydrogen atom or an optionally substituted hydroxy group) or carbonyl; and $X^6$ is $CR^{13}R^{14}$ ($R^{13}$ and $R^{14}$ are each independently a hydrogen atom or an optionally substituted $C_{1-6}$ alkyl group (e.g., methyl)) or an oxygen atom.

[Compound B]

Compound (I) wherein ring A group is a $C_{6-14}$ aryl group (e.g., phenyl), a 5- or 6-membered monocyclic aromatic heterocyclic group (e.g., thienyl, pyridyl, pyrimidinyl) or a 8- to 14-membered fused polycyclic (preferably bicyclic or tricyclic) aromatic heterocyclic group (e.g., benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) a $C_{1-6}$ alkyl group (e.g., methyl) optionally substituted by 1 to 3 halogen atoms (e.g., fluorine atom), (4) a $C_{6-14}$ aryl group (e.g., phenyl), (5) a $C_{1-6}$ alkoxy group (e.g., methoxy), (6) a carboxy group, (7) a $C_{1-6}$ alkoxy-carbonyl group (e.g., methoxycarbonyl), (8) a carbamoyl group optionally mono- or di-substituted by a 5- to 14-membered aromatic heterocyclic group (e.g., pyrazolyl) optionally substituted by 1 to 3 $C_{1-6}$ alkyl groups (e.g., methyl), and (9) a 5- to 14-membered aromatic heterocyclic group (e.g., pyrazolyl, imidazolyl, triazolyl, thiazolyl, pyridyl, pyrimidinyl, pyridazinyl) optionally substituted by 1 to 3 substituents selected from (i) a cyano group, (ii) a $C_{1-6}$ alkyl group (e.g., methyl, ethyl, isopropyl, isobutyl, tert-butyl) optionally substituted by 1 to 3 substituents selected from a halogen atom (e.g., fluorine atom), a hydroxy group and a 3- to 14-membered non-aromatic heterocyclic group (e.g., morpholinyl), (iii) a $C_{3-10}$ cycloalkyl group (e.g., cyclopropyl), (iv) a $C_{1-6}$ alkoxy group (e.g., methoxy), (v) an oxo group, (vi) a $C_{1-6}$ alkoxy-carbonyl group (e.g., tert-butoxycarbonyl) and (vii) a 3- to 14-membered non-aromatic heterocyclic group (e.g., tetrahydropyranyl);

ring B group is (1) a group represented by the formula (II);

$R^1$ is a hydrogen atom, a halogen atom (e.g., chlorine atom), a cyano group, an alkyl group (e.g., methyl), an amino group optionally mono- or di-substituted by a $C_{1-6}$ alkyl group (e.g., methyl), or a hydroxy group optionally substituted by a $C_{1-6}$ alkyl group (e.g., methyl);

$R^2$ is (1) a $C_{1-6}$ alkyl group (e.g., methyl, ethyl, isopropyl) optionally substituted by 1 to 3 substituents selected from a $C_{3-10}$ cycloalkyl group (e.g., cyclopropyl, cyclopentyl) and a $C_{6-14}$ aryl group (e.g., phenyl), (2) a $C_{3-10}$ cycloalkyl group (e.g., cyclopropyl, cyclobutyl, cyclopentyl, bicyclo[1.1.1]pentyl) optionally substituted by 1 to 3 substituents selected from a halogen atom (e.g., fluorine atom), a hydroxy group and a $C_{1-6}$-alkyl group (e.g., methyl), or (3) a 3- to 14-membered non-aromatic heterocyclic group (e.g., tetrahydrofuranyl, tetrahydropyranyl, 1,4-dioxanyl, tetrahydrothienyl) optionally substituted by 1 to 3 oxo groups;

$R^3$ is (1) a hydrogen atom, (2) a $C_{1-6}$ alkyl group (e.g., methyl, ethyl) optionally substituted by 1 to 3 substituents selected from (i) a cyano group, (ii) a hydroxy group, (iii) a $C_{3-10}$ cycloalkyl group (e.g., cyclopropyl), (iv) a $C_{6-14}$ aryl group (e.g., phenyl), (v) a $C_{7-16}$ aralkyloxy group (e.g., benzyloxy), (vi) a carboxy group and (vii) a carbamoyl group optionally mono- or di-substituted by a $C_{1-6}$ alkyl group (e.g., methyl), or (3) a $C_{3-10}$ cycloalkyl group (e.g., cyclopropyl);

$X^1$ is $CR^4$ ($R^4$ is a hydrogen atom or a fluorine atom) or a nitrogen atom; or (2) a group represented by the formula (III);

$R^5$ is a hydrogen atom, a $C_{1-6}$ alkyl group (e.g., methyl, ethyl) optionally substituted by 1 to 3 halogen atoms (e.g., fluorine atom), a cycloalkyl group (e.g., cyclopropyl), or a hydroxy group optionally substituted by a $C_{1-6}$ alkyl group (e.g., methyl);

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently, (1) a hydrogen atom, (2) a cyano group, (3) a $C_{1-6}$ alkyl group (e.g., methyl, ethyl, tert-butyl) optionally substituted by 1 to 3 substituents selected from a hydroxy group and a $C_{3-10}$ cycloalkyl group (e.g., cyclopropyl), or (4) a $C_{3-10}$ cycloalkyl group (e.g., cyclopropyl, cyclobutyl) optionally substituted by 1 to 3 $C_{1-6}$ alkyl groups (e.g., methyl), or $R^8$ and $R^9$ may be bonded to each other to form, together with the adjacent carbon atom, $C_{3-10}$ cycloalkane (e.g., cyclopropane, cyclobutane)) or $NR^{10}$ ($R^{10}$ is a $C_{1-6}$ alkyl group (e.g., isopropyl));

$X^5$ is $CR^{11}R^{12}$ ($R^{11}$ and $R^{12}$ are each a hydrogen atom or a hydroxy group) or carbonyl; and $X^6$ is $CR^{13}R^{14}$ ($R^{13}$ and $R^{14}$ are each independently a hydrogen atom or a $C_{1-6}$ alkyl group (e.g., methyl)) or an oxygen atom.

[Compound C]

Compound (I) wherein ring A group is phenyl optionally substituted by 1 to 5 (preferably 1 to 3, more preferably 1 or 2) substituents selected from (1) a halogen atom (e.g., fluorine atom), (2) a cyano group, and (3) a 5- to 14-membered aromatic heterocyclic group (e.g., pyrazolyl) optionally substituted by 1 to 3 substituents selected from a $C_{1-6}$ alkyl group (e.g., methyl) and a $C_{3-10}$ cycloalkyl group (e.g., cyclopropyl);

ring B group is (1) a group represented by the formula (II);

$R^1$ is a hydrogen atom;

$R^2$ is a $C_{3-10}$ cycloalkyl group (e.g., cyclopentyl) or a 3- to 14-membered non-aromatic heterocyclic group (e.g., tetrahydrofuranyl, tetrahydropyranyl, 1,4-dioxanyl);

$R^3$ is a hydrogen atom or a $C_{1-6}$ alkyl group (e.g., methyl);

$X^1$ is nitrogen atom; or (2) a group represented by the formula (III);

$R^5$ is a $C_{1-6}$ alkyl group (e.g., methyl);

$X^2$ is $CR^6$ ($R^{66}$ is a hydrogen atom);

$X^3$ is $CR^7$ ($R^7$ is a hydrogen atom) or a nitrogen atom;

$X^4$ is $CR^8R^9$ ($R^8$ and $R^9$ are each independently, a cyano group or a $C_{3-10}$ cycloalkyl group (e.g., cyclopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are hydrogen atoms).

[Compound D]

Compound (I) wherein ring A group is phenyl optionally substituted by 1 to 5 (preferably 1 to 3, more preferably 1 or 2) substituents selected from (1) a halogen atom (e.g., fluorine atom) and (2) a 5- to 14-membered aromatic heterocyclic group (e.g., pyrazolyl) optionally substituted by 1 to 3 $C_{1-6}$ alkyl groups (e.g., methyl);

ring B group is (1) a group represented by the formula (II);

$R^1$ is a hydrogen atom;

$R^2$ is a 3- to 14-membered non-aromatic heterocyclic group (e.g., 1,4-dioxanyl);

$R^3$ is a hydrogen atom;

$X^1$ is nitrogen atom; or (2) a group represented by the formula (III);

$R^5$ is a $C_{1-6}$ alkyl group (e.g., methyl);

$X^2$ is $CR^6$ ($R^{66}$ is a hydrogen atom);

$X^3$ is $CR^7$ ($R^7$ is a hydrogen atom);

$X^4$ is $CR^8R^9$ ($R^8$ and $R^9$ are each independently a cyano group or a $C_{3-10}$ cycloalkyl group (e.g., cyclopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are hydrogen atoms).

[Compound A-1]

Compound (I) wherein ring A group is a $C_{6-14}$ aryl group (e.g., phenyl) or an aromatic heterocyclic group (pyridyl, pyrimidinyl, benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) a carboxy group, (7) an optionally substituted $C_{1-6}$ alkoxy-carbonyl group (e.g., methoxycarbonyl), (8) an optionally substituted carbamoyl group, and (9) an optionally substituted 5- to 14-membered aromatic heterocyclic group (e.g., pyrazolyl, imidazolyl, triazolyl, pyridyl, pyridazinyl);

ring B group is a group represented by the formula (II);

$R^1$ is a hydrogen atom, a halogen atom (e.g., chlorine atom), a cyano group, an optionally substituted alkyl group (e.g., methyl), an optionally substituted amino group, or an optionally substituted hydroxy group;

$R^2$ is an optionally substituted $C_{1-6}$ alkyl group (e.g., methyl, ethyl, isopropyl), an optionally substituted $C_{3-10}$ cycloalkyl group (e.g., cyclopropyl, cyclobutyl, cyclopentyl, bicyclo[1.1.1]pentyl) or an optionally substituted 3- to 14-membered non-aromatic heterocyclic group (e.g., tetrahydrofuranyl, tetrahydropyranyl, 1,4-dioxanyl, tetrahydrothienyl);

$R^3$ is a hydrogen atom, an optionally substituted $C_{1-6}$ alkyl group (e.g., methyl, ethyl) or an optionally substituted $C_{3-10}$ cycloalkyl group (e.g., cyclopropyl); and $X^1$ is $CR^4$ ($R^4$ is a hydrogen atom or a halogen atom (e.g., fluorine atom)) or a nitrogen atom.

[Compound B-1]

Compound (I) wherein ring A group is a $C_{6-14}$ aryl group (e.g., phenyl), a 5- or 6-membered monocyclic aromatic heterocyclic group (e.g., pyridyl, pyrimidinyl) or a 8- to 14-membered fused polycyclic (preferably bicyclic or tricyclic) aromatic heterocyclic group (e.g., benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) a $C_{1-6}$ alkyl group (e.g., methyl), (4) a $C_{6-14}$ aryl group (e.g., phenyl), (5) a $C_{1-6}$ alkoxy group (e.g., methoxy), (6) a carboxy group, (7) a $C_{1-6}$ alkoxy-carbonyl group (e.g., methoxycarbonyl), (8) a carbamoyl group optionally mono- or di-substituted by a 5- to 14-membered aromatic heterocyclic group (e.g., pyrazolyl) optionally substituted by 1 to 3 $C_{1-6}$ alkyl groups (e.g., methyl), and (9) a 5- to 14-membered aromatic heterocyclic group (e.g., pyrazolyl, imidazolyl, triazolyl, pyridyl, pyridazinyl) optionally substituted by 1 to 3 substituents selected from (i) a cyano group, (ii) a $C_{1-6}$ alkyl group (e.g., methyl, ethyl, isopropyl, tert-butyl) optionally substituted by 1 to 3 substituents selected from a halogen atom (e.g., fluorine atom) and a hydroxy group, (iii) a $C_{3-10}$ cycloalkyl group (e.g., cyclopropyl), (iv) a $C_{1-6}$ alkoxy group (e.g., methoxy) and (v) an oxo group;

ring B group is a group represented by the formula (II);

$R^1$ is a hydrogen atom, a halogen atom (e.g., chlorine atom), a cyano group, an alkyl group (e.g., methyl), an amino group optionally mono- or di-substituted by a $C_{1-6}$ alkyl group (e.g., methyl), or a hydroxy group optionally substituted by a $C_{1-6}$ alkyl group (e.g., methyl);

$R^2$ is (1) a $C_{1-6}$ alkyl group (e.g., methyl, ethyl, isopropyl) optionally substituted by 1 to 3 substituents selected from a $C_{3-10}$ cycloalkyl group (e.g., cyclopropyl, cyclopentyl) and a $C_{6-14}$ aryl group (e.g., phenyl), (2) a $C_{3-10}$ cycloalkyl group (e.g., cyclopropyl, cyclobutyl, cyclopentyl, bicyclo[1.1.1]pentyl) optionally substituted by 1 to 3 substituents selected from a halogen atom (e.g., fluorine atom), a hydroxy group and a $C_{1-6}$ alkyl group (e.g., methyl), or (3) a 3- to 14-membered non-aromatic heterocyclic group (e.g., tetrahydrofuranyl, tetrahydropyranyl, 1,4-dioxanyl, tetrahydrothienyl) optionally substituted by 1 to 3 oxo groups;

$R^3$ is (1) a hydrogen atom, (2) a $C_{1-6}$ alkyl group (e.g., methyl, ethyl) optionally substituted by 1 to 3 substituents selected from (i) a cyano group, (ii) a hydroxy group, (iii) a $C_{3-10}$ cycloalkyl group (e.g., cyclopropyl), (iv) a $C_{6-14}$ aryl group (e.g., phenyl), (v) a $C_{7-16}$ aralkyloxy group (e.g., benzyloxy), (vi) a carboxy group and (vii) a carbamoyl group optionally mono- or di-substituted by a $C_{1-6}$ alkyl group (e.g., methyl), or (3) a $C_{3-10}$ cycloalkyl group (e.g., cyclopropyl); and $X^1$ is $CR^4$ ($R^4$ is a hydrogen atom or a fluorine atom) or a nitrogen atom.

[Compound C-1]

Compound (I) wherein ring A group is phenyl optionally substituted by 1 to 5 (preferably 1 to 3, more preferably 1 or 2) substituents selected from (1) a halogen atom (e.g., fluorine atom), (2) a cyano group, and (3) a 5- to 14-membered aromatic heterocyclic group (e.g., pyrazolyl) optionally substituted by 1 to 3 $C_{1-6}$ alkyl groups (e.g., methyl);

ring B group is a group represented by the formula (II);

$R^1$ is a hydrogen atom;

$R^2$ is a $C_{3-10}$ cycloalkyl group (e.g., cyclopentyl) or a 3- to 14-membered non-aromatic heterocyclic group (e.g., tetrahydrofuranyl, tetrahydropyranyl, 1,4-dioxanyl);

$R^3$ is a hydrogen atom or a $C_{1-6}$ alkyl group (e.g., methyl); and $X^1$ is nitrogen atom.

[Compound D-1]

Compound (I) wherein ring A group is phenyl optionally substituted by 1 to 5 (preferably 1 to 3, more preferably 1 or 2) substituents selected from (1) a halogen atom (e.g., fluorine atom) and (2) a 5- to 14-membered aromatic heterocyclic group (e.g., pyrazolyl) optionally substituted by 1 to 3 $C_{1-6}$ alkyl groups (e.g., methyl);

ring B group is a group represented by the formula (II);

$R^1$ is a hydrogen atom;

$R^2$ is a 3- to 14-membered non-aromatic heterocyclic group (e.g., 1,4-dioxanyl);

$R^3$ is a hydrogen atom; and $X^1$ is nitrogen atom.

[Compound A-2]

Compound (I) wherein ring A group is a $C_{6-14}$ aryl group (e.g., phenyl) or an aromatic heterocyclic group (thienyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) an optionally substituted $C_{1-6}$ alkyl group (e.g., methyl), and (4) an optionally substituted 5- to 14-membered aromatic heterocyclic group (e.g., pyrazolyl, imidazolyl, triazolyl, thiazolyl, pyridyl, pyrimidinyl, pyridazinyl);

ring B group is a group represented by the formula (III);

$R^5$ is a hydrogen atom, an optionally substituted alkyl group (e.g., methyl, ethyl), an optionally substituted cycloalkyl group (e.g., cyclopropyl), or an optionally substituted hydroxy group;

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently a hydrogen atom, a cyano group, an optionally substituted $C_{1-6}$ alkyl group (e.g., methyl, ethyl, tert-butyl) or an optionally substituted $C_{3-10}$ cycloalkyl group (e.g., cyclopropyl, cyclobutyl), or $R^8$ and $R^9$ may be bonded to each other to form, together with the adjacent carbon atom, an optionally further substituted $C_{3-10}$ cycloalkane (e.g., cyclopropane, cyclobutane)) or $NR^{10}$ ($R^{10}$ is an optionally substituted $C_{1-6}$ alkyl group (e.g., isopropyl));

$X^5$ is $CR^{11}R^{12}$ ($R^{11}$ and $R^{12}$ are each independently a hydrogen atom or an optionally substituted hydroxy group) or carbonyl; and $X^6$ is $CR^{13}R^{14}$ ($R^{13}$ and $R^{14}$ are each independently a hydrogen atom or an optionally substituted $C_{1-6}$ alkyl group (e.g., methyl)) or an oxygen atom.

[Compound B-2]

Compound (I) wherein ring A group is a $C_{6-14}$ aryl group (e.g., phenyl) or a 5- or 6-membered monocyclic aromatic heterocyclic group (e.g., thienyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) a $C_{1-6}$ alkyl group (e.g., methyl) optionally substituted by 1 to 3 halogen atoms (e.g., fluorine atom) and (4) a 5- to 14-membered aromatic heterocyclic group (e.g., pyrazolyl, imidazolyl, triazolyl, pyridyl, pyridazinyl) optionally substituted by 1 to 3 substituents selected from (i) a halogen atom (e.g., fluorine atom), (ii) a $C_{1-6}$ alkyl group (e.g., methyl, ethyl, isopropyl, tert-butyl) optionally substituted by 1 to 3 substituents selected from a halogen atom (e.g., fluorine atom), a hydroxy group and a 3- to 14-membered non-aromatic heterocyclic group (e.g., morpholinyl), (iii) a $C_{3-10}$ cycloalkyl group (e.g., cyclopropyl), (iv) a $C_{1-6}$ alkoxy group (e.g., methoxy), (v) an oxo group, (vi) a $C_{1-6}$ alkoxy-carbonyl group (e.g., tert-butoxycarbonyl) and (vii) a 3- to 14-membered non-aromatic heterocyclic group (e.g., tetrahydropyranyl);

ring B group is a group represented by the formula (III);

$R^5$ is a hydrogen atom, a $C_{1-6}$ alkyl group (e.g., methyl, ethyl) optionally substituted by 1 to 3 halogen atoms (e.g., fluorine atom), a cycloalkyl group (e.g., cyclopropyl), or a hydroxy group optionally substituted by a $C_{1-6}$ alkyl group (e.g., methyl);

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently, (1) a hydrogen atom, (2) a cyano group, (3) a $C_{1-6}$ alkyl group (e.g., methyl, ethyl, tert-butyl) optionally substituted by 1 to 3 substituents selected from a hydroxy group and a $C_{3-10}$ cycloalkyl group (e.g., cyclopropyl) or (4) a $C_{3-10}$ cycloalkyl group (e.g., cyclopropyl, cyclobutyl) optionally substituted by 1 to 3 $C_{1-6}$ alkyl groups (e.g., methyl), or $R^8$ and $R^9$ may be bonded to each other to form, together with the adjacent carbon atom, $C_{3-10}$ cycloalkane (e.g., cyclopropane, cyclobutane)) or $NR^{10}$ ($R^{10}$ is a $C_{1-6}$ alkyl group (e.g., isopropyl));

$X^5$ is $CR^{11}R^{12}$ ($R^{11}$ and $R^{12}$ are each independently a hydrogen atom or a hydroxy group) or carbonyl; and $X^6$ is $CR^{13}R^{14}$ ($R^{13}$ and $R^{14}$ are each independently a hydrogen atom or a $C_{1-6}$ alkyl group (e.g., methyl)) or an oxygen atom.

[Compound C-2]

Compound (I) wherein ring A group is phenyl optionally substituted by 1 to 5 (preferably 1 to 3, more preferably 1 or 2) substituents selected from (1) a halogen atom (e.g., fluorine atom), and (2) a 5- to 14-membered aromatic heterocyclic group (e.g., pyrazolyl) optionally substituted by to 3 substituents selected from a $C_{1-6}$ alkyl group (e.g., methyl) and a $C_{3-10}$ cycloalkyl group (e.g., cyclopropyl);

ring B group is a group represented by the formula (III);

$R^5$ is a $C_{1-6}$ alkyl group (e.g., methyl);

$X^2$ is $CR^6$ ($R^{66}$ is a hydrogen atom);

$X^3$ is $CR^7$ ($R^7$ is a hydrogen atom) or a nitrogen atom;

$X^4$ is $CR^8R^9$ ($R^8$ and $R^9$ are each independently, a cyano group or a $C_{3-10}$ cycloalkyl group (e.g., cyclopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are hydrogen atoms).

[Compound D-2]

Compound (I) wherein ring A group is (1) a halogen atom (e.g., fluorine atom) or (2) a 5- to 14-membered aromatic heterocyclic group (e.g., pyrazolyl) optionally substituted by 1 to 3 $C_{1-6}$ alkyl groups (e.g., methyl);

ring B group is a group represented by the formula (III);

$R^5$ is a $C_{1-6}$ alkyl group (e.g., methyl);

$X^2$ is $CR^6$ ($R^{66}$ is a hydrogen atom);

$X^3$ is $CR^7$ ($R^7$ is a hydrogen atom);

$X^4$ is $CR^8R^9$ ($R^8$ and $R^9$ are each independently a cyano group or a $C_{3-10}$ cycloalkyl group (e.g., cyclopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are hydrogen atoms).

[Compound A-3]

Compound (I) wherein ring A group is a $C_{6-14}$ aryl group (e.g., phenyl) or an aromatic heterocyclic group (thienyl, pyridyl, pyrimidinyl, benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) a carboxy group, (7) an optionally substituted $C_{1-6}$ alkoxy-carbonyl group (e.g., methoxycarbonyl), (8) an optionally substituted carbamoyl group, and (9) an optionally substituted 5- to 14-membered aromatic heterocyclic group (e.g., pyrazolyl, imidazolyl, triazolyl, thiazolyl, pyridyl, pyrimidinyl, pyridazinyl);

ring B group is (1) a group represented by the formula (II);

$R^1$ is a hydrogen atom, a halogen atom (e.g., chlorine atom), a cyano group, an optionally substituted alkyl group (e.g., methyl), an optionally substituted amino group, or an optionally substituted hydroxy group;

$R^2$ is an optionally substituted $C_{1-6}$ alkyl group (e.g., methyl, ethyl, isopropyl), an optionally substituted $C_{3-10}$ cycloalkyl group (e.g., cyclopropyl, cyclobutyl, cyclopentyl, bicyclo[1.1.1]pentyl) or an optionally substituted 3- to 14-membered non-aromatic heterocyclic group (e.g., tetrahydrofuranyl, tetrahydropyranyl, 1,4-dioxanyl, tetrahydrothienyl);

$R^3$ is a hydrogen atom, an optionally substituted $C_{1-6}$ alkyl group (e.g., methyl, ethyl) or an optionally substituted $C_{3-10}$ cycloalkyl group (e.g., cyclopropyl);

$X^1$ is $CR^4$ ($R^4$ is a hydrogen atom or a halogen atom (e.g., fluorine atom)) or a nitrogen atom; or (2) a group represented by the formula (III);

$R^5$ is a hydrogen atom, an optionally substituted alkyl group (e.g., methyl, ethyl), an optionally substituted cycloalkyl group (e.g., cyclopropyl), or an optionally substituted hydroxy group;

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently a hydrogen atom, a cyano group, an optionally substituted $C_{1-6}$ alkyl group (e.g., methyl, ethyl, tert-butyl) or an optionally substituted $C_{3-10}$ cycloalkyl group (e.g., cyclopropyl, cyclobutyl), or $R^8$ and $R^9$ may be bonded to each other to form, together with the adjacent carbon atom, an optionally further substituted $C_{3-10}$ cycloalkane (e.g., cyclopropane, cyclobutane)) or $NR^{10}$ ($R^{10}$ is an optionally substituted $C_{1-6}$ alkyl group (e.g., isopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are each independently a hydrogen atom or an optionally substituted $C_{1-6}$ alkyl group (e.g., methyl)) or an oxygen atom.

[Compound B-3]

Compound (I) wherein ring A group is a $C_{6-14}$ aryl group (e.g., phenyl), a 5- or 6-membered monocyclic aromatic heterocyclic group (e.g., thienyl, pyridyl, pyrimidinyl) or a 8- to 14-membered fused polycyclic (preferably bicyclic or tricyclic) aromatic heterocyclic group (e.g., benzopyrazolyl, pyrazolopyridyl, imidazopyridyl, benzimidazolyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) a $C_{1-6}$ alkyl group (e.g., methyl) optionally substituted by 1 to 3 halogen atoms (e.g., fluorine atom), (4) a $C_{6-14}$ aryl group (e.g., phenyl), (5) a $C_{1-6}$ alkoxy group (e.g., methoxy), (6) a carboxy group, (7) a $C_{1-6}$ alkoxy-carbonyl group (e.g., methoxycarbonyl), (8) a carbamoyl group optionally mono- or di-substituted by a 5- to 14-membered aromatic heterocyclic group (e.g., pyrazolyl) optionally substituted by 1 to 3 $C_{1-6}$ alkyl groups (e.g., methyl), and (9) a 5- to 14-membered aromatic heterocyclic group (e.g., pyrazolyl, imidazolyl, triazolyl, thiazolyl, pyridyl, pyrimidinyl, pyridazinyl) optionally substituted by 1 to 3 substituents selected from (i) a cyano group, (ii) a $C_{1-6}$ alkyl group (e.g., methyl, ethyl, isopropyl, isobutyl, tert-butyl) optionally substituted by 1 to 3 substituents selected from a halogen atom (e.g., fluorine atom), a hydroxy group and a 3- to 14-membered non-aromatic heterocyclic group (e.g., morpholinyl), (iii) a $C_{3-10}$ cycloalkyl group (e.g., cyclopropyl), (iv) a $C_{1-6}$ alkoxy group (e.g., methoxy), (v) an oxo group, (vi) a $C_{1-6}$ alkoxy-carbonyl group (e.g., tert-butoxycarbonyl), and (vii) a 3- to 14-membered non-aromatic heterocyclic group (e.g., tetrahydropyranyl);

ring B group is (1) a group represented by the formula (II);

$R^1$ is a hydrogen atom, a halogen atom (e.g., chlorine atom), a cyano group, an alkyl group (e.g., methyl), an amino group optionally mono- or di-substituted by a $C_{1-6}$ alkyl group (e.g., methyl), or a hydroxy group optionally substituted by a $C_{1-6}$ alkyl group (e.g., methyl);

$R^2$ is (1) a $C_{1-6}$ alkyl group (e.g., methyl, ethyl, isopropyl) optionally substituted by 1 to 3 substituents selected from a $C_{3-10}$ cycloalkyl group (e.g., cyclopropyl, cyclopentyl) and a $C_{6-14}$ aryl group (e.g., phenyl), (2) a $C_{3-10}$ cycloalkyl group (e.g., cyclopropyl, cyclobutyl, cyclopentyl, bicyclo[1.1.1]pentyl) optionally substituted by 1 to 3 substituents selected from a halogen atom (e.g., fluorine atom), a hydroxy group and a $C_{1-6}$ alkyl group (e.g., methyl), or (3) a 3- to 14-membered non-aromatic heterocyclic group (e.g., tetrahydrofuranyl, tetrahydropyranyl, 1,4-dioxanyl, tetrahydrothienyl) optionally substituted by 1 to 3 oxo groups;

$R^3$ is (1) a hydrogen atom, (2) a $C_{1-6}$ alkyl group (e.g., methyl, ethyl) optionally substituted by 1 to 3 substituents selected from (i) a cyano group, (ii) a hydroxy group, (iii) a $C_{3-10}$ cycloalkyl group (e.g., cyclopropyl), (iv) a $C_{6-14}$ aryl group (e.g., phenyl), (v) a $C_{7-16}$ aralkyloxy group (e.g., benzyloxy), (vi) a carboxy group and (vii) a carbamoyl group optionally mono- or di-substituted by a $C_{1-6}$ alkyl group (e.g., methyl), or (3) a $C_{3-10}$ cycloalkyl group (e.g., cyclopropyl);

$X^1$ is $CR^4$ ($R^4$ is a hydrogen atom or a fluorine atom) or a nitrogen atom; or (2) a group represented by the formula (III);

$R^5$ is a hydrogen atom, a $C_{1-6}$ alkyl group (e.g., methyl, ethyl) optionally substituted by 1 to 3 halogen atoms (e.g., fluorine atom), a cycloalkyl group (e.g., cyclopropyl), or a hydroxy group optionally substituted by a $C_{1-6}$ alkyl group (e.g., methyl);

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently, (1) a hydrogen atom, (2) a cyano group, (3) a $C_{1-6}$ alkyl group (e.g., methyl, ethyl, tert-butyl) optionally substituted by 1 to 3 substituents selected from a hydroxy group and a $C_{3-10}$ cycloalkyl group (e.g., cyclopropyl) or (4) a $C_{3-10}$ cycloalkyl group (e.g., cyclopropyl, cyclobutyl) optionally substituted by 1 to 3 $C_{1-6}$ alkyl groups (e.g., methyl), or $R^8$ and $R^9$ may be bonded to each other to form, together with the adjacent carbon atom, $C_{3-10}$ cycloalkane (e.g., cyclopropane, cyclobutane)) or $NR^{10}$ ($R^{10}$ is a $C_{1-6}$ alkyl group (e.g., isopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are each independently a hydrogen atom or a $C_{1-6}$ alkyl group (e.g., methyl)) or an oxygen atom.

[Compound A-4]

Compound (I) wherein ring A group is a $C_{6-14}$ aryl group (e.g., phenyl) or an aromatic heterocyclic group (thienyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) an optionally substituted $C_{1-6}$ alkyl group (e.g., methyl), and (4) an optionally substituted 5- to 14-membered aromatic heterocyclic group (e.g., pyrazolyl, imidazolyl, triazolyl, thiazolyl, pyridyl, pyrimidinyl, pyridazinyl);

ring B group is a group represented by the formula (III);

$R^5$ is a hydrogen atom, an optionally substituted alkyl group (e.g., methyl, ethyl), an optionally substituted cycloalkyl group (e.g., cyclopropyl), or an optionally substituted hydroxy group;

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently a hydrogen atom, a cyano group, an optionally substituted $C_{1-6}$ alkyl group (e.g., methyl, ethyl, tert-butyl) or an optionally substituted $C_{3-10}$ cycloalkyl group (e.g., cyclopropyl, cyclobutyl), or $R^8$ and $R^9$ may be bonded to each other to form, together with the adjacent carbon atom, an optionally further substituted $C_{3-10}$ cycloalkane (e.g., cyclopropane, cyclobutane)) or $NR^{10}$ ($R^{10}$ is an optionally substituted $C_{1-6}$ alkyl group (e.g., isopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are each independently a hydrogen atom or an optionally substituted $C_{1-6}$ alkyl group (e.g., methyl)) or an oxygen atom.

[Compound B-4]

Compound (I) wherein ring A group is a $C_{6-14}$ aryl group (e.g., phenyl) or a 5- or 6-membered monocyclic aromatic heterocyclic group (e.g., thienyl), each of which is optionally substituted by 1 to 5 (preferably 1 to 3, more preferably 1 or 2) substituents selected from (1) a halogen atom (e.g., fluorine atom, chlorine atom, bromine atom), (2) a cyano group, (3) a $C_{1-6}$ alkyl group (e.g., methyl) optionally substituted by 1 to 3 halogen atoms (e.g., fluorine atom) and (4) a 5- to 14-membered aromatic heterocyclic group (e.g., pyrazolyl, imidazolyl, triazolyl, pyridyl, pyridazinyl) optionally substituted by 1 to 3 substituents selected from (i) a halogen atom (e.g., fluorine atom), (ii) a $C_{1-6}$ alkyl group (e.g., methyl, ethyl, isopropyl, tert-butyl) optionally substituted by 1 to 3 substituents selected from a halogen atom (e.g., fluorine atom), a hydroxy group and a 3- to 14-membered non-aromatic heterocyclic group (e.g., morpholinyl), (iii) a $C_{3-10}$ cycloalkyl group (e.g., cyclopropyl), (iv) a $C_{1-6}$ alkoxy group (e.g., methoxy), (v) an oxo group, (vi) a $C_{1-6}$ alkoxy-carbonyl group (e.g., tert-butoxycarbonyl) and (vii) a 3- to 14-membered non-aromatic heterocyclic group (e.g., tetrahydropyranyl);

ring B group is a group represented by the formula (III);

$R^5$ is a hydrogen atom, a $C_{1-6}$ alkyl group (e.g., methyl, ethyl) optionally substituted by 1 to 3 halogen atoms (e.g., fluorine atom), a cycloalkyl group (e.g., cyclopropyl), or a hydroxy group optionally substituted by a $C_{1-6}$ alkyl group (e.g., methyl);

$X^2$ is $CR^6$ ($R^6$ is a hydrogen atom) or a nitrogen atom;

$X^3$ is $CR^7$ ($R^7$ is a hydrogen atom) or a nitrogen atom;

$X^4$ is $CR^8R^9$ ($R^8$ and $R^9$ are each independently, (1) a hydrogen atom, (2) a cyano group, (3) a $C_{1-6}$ alkyl group (e.g., methyl, ethyl, tert-butyl) optionally substituted by 1 to 3 substituents selected from a hydroxy group and a $C_{3-10}$ cycloalkyl group (e.g., cyclopropyl) or (4) a $C_{3-10}$ cycloalkyl group (e.g., cyclopropyl, cyclobutyl) optionally substituted by 1 to 3 $C_{1-6}$ alkyl groups (e.g., methyl), or $R^8$ and $R^9$ may be bonded to each other to form, together with the adjacent carbon atom, $C_{3-10}$ cycloalkane (e.g., cyclopropane, cyclobutane)) or $NR^{10}$ ($R^{10}$ is a $C_{1-6}$ alkyl group (e.g., isopropyl));

$X^5$ is $CR^{11}R^{12}$ ($R^{11}$ and $R^{12}$ are hydrogen atoms); and $X^6$ is $CR^{13}R^{14}$ ($R^{13}$ and $R^{14}$ are each independently a hydrogen atom or a $C_{1-6}$ alkyl group (e.g., methyl)) or an oxygen atom.

Specific examples of compound (I) include the compounds of the below-mentioned Examples 1-152 and 154-240.

Among those, 8-cyclopentyl-N-(3-fluoro-5-(l-methyl-1H-pyrazol-4-yl)benzyl)-7H-purine-6-carboxamide or a salt thereof;

N-(3-cyano-5-(l-methyl-1H-pyrazol-4-yl)benzyl)-7-methyl-8-(tetrahydrofuran-2-yl)-7H-purine-6-carboxamide or a salt thereof;

8-(1,4-dioxan-2-yl)-N-(3-fluoro-5-(1-methyl-1H-pyrazol-4-yl)benzyl)-7H-purine-6-carboxamide or a salt thereof;

8-(1,4-dioxan-2-yl)-N-(3-fluoro-5-(1-methyl-1H-pyrazol-4-yl)benzyl)-7H-purine-6-carboxamide or a salt thereof (tR1);

8-(1,4-dioxan-2-yl)-N-(3-fluoro-5-(1-methyl-1H-pyrazol-4-yl)benzyl)-7H-purine-6-carboxamide or a salt thereof (tR2);

N-(3-fluoro-5-(1-methyl-1H-pyrazol-4-yl)benzyl)-7-methyl-8-(tetrahydro-2H-pyran-2-yl)-7H-purine-6-carboxamide or a salt thereof;

4-((3S)-3-cyano-3-cyclopropyl-2-oxopyrrolidin-1-yl)-N-(3-fluoro-5-(1-methyl-1H-pyrazol-4-yl)benzyl)-6-methylpyridine-2-carboxamide or a salt thereof;

4-((3S)-3-cyano-3-cyclopropyl-2-oxopyrrolidin-1-yl)-N-(3-(1-cyclopropyl-1H-pyrazol-4-yl)-5-fluorobenzyl)-6-methylpyridine-2-carboxamide or a salt thereof; or 4-((3S)-3-cyano-3-cyclopropyl-2-oxopyrrolidin-1-yl)-N-(3-fluoro-5-(1-methyl-1H-pyrazol-4-yl)benzyl)-6-methylpyrimidine-2-carboxamide or a salt thereof is preferable, particularly, 8-(1,4-dioxan-2-yl)-N-(3-fluoro-5-(1-methyl-1H-pyrazol-4-yl)benzyl)-7H-purine-6-carboxamide or a salt thereof; or 4-((3S)-3-cyano-3-cyclopropyl-2-oxopyrrolidin-1-yl)-N-(3-fluoro-5-(1-methyl-1H-pyrazol-4-yl)benzyl)-6-methylpyridine-2-carboxamide or a salt thereof is preferable.

As a salt of a compound represented by the formula (I), a pharmacologically acceptable salt is preferable. Examples of such salt include salts with inorganic base, salts with organic base, salts with inorganic acid, salts with organic acid, and salts with basic or acidic amino acid.

Preferable examples of the salt with inorganic base include alkali metal salts such as sodium salt, potassium salt and the like; alkaline earth metal salts such as calcium salt, magnesium salt, and the like; aluminum salt; ammonium salt, and the like.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N'-dibenzylethylenediamine and the like.

Preferable examples of the salt with inorganic acid include salts with hydrogen chloride, hydrobromic acid, nitric acid, sulfuric acid, and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with basic amino acid include salts with arginine, lysine, and ornithine.

Preferable examples of the salt with acidic amino acid include salts with aspartic acid, and glutamic acid.

When compound (I) is a salt, salts with hydrogen chloride, trifluoroacetic acid are particularly preferable.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature-300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbon s: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
s inorganic acids: hydrochloric acid, sulfuric acid and the like;
esters: ethyl acetate and the like;
ketones: acetone, methyl ethyl ketone and the like; and
water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, t-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as t-butylcarbonate and the like, and the like.

Examples of the protecting group of the carbonyl group of aldehyde include acetal protecting groups such as dimethyl acetal and the like; cyclic acetal protecting groups such as cyclic 1,3-dioxane and the like, and the like.

Examples of the protecting group of the carbonyl group of ketone include ketal protecting groups such as dimethyl ketal and the like; cyclic ketal protecting groups such as cyclic 1,3-dioxane and the like; oxime protecting groups such as O-methyloxime and the like; hydrazone protecting groups such as N,N-dimethylhydrazone and the like, and the like.

Examples of the protecting group for carboxy group include ester-type protecting groups such as methyl ester and the like; and amide-type protecting groups such as N,N-dimethylamide and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an acid anhydride such as acetic anhydride and the like can also be used instead of an acid chloride.

When an aromatic nucleophilic substitution reaction is performed in each step, a nucleophilic agent (e.g., amines, imidazole and the like) and a base (e.g., basic salts, organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; 2,4,6-tripropyl-1,3,5,2,4,6-trioxatriphosphorinane-2,4,6-trioxide (T3P); combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When a coupling reaction is performed in each step, examples of the metal catalyst to be used include palladium compounds such as palladium(II) acetate, tetrakis(triphenylphosphine)palladium(0), dichlorobis(triphenylphosphine)

palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases, basic salts and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining an alkyl halide form from alcohol by reacting with triphenylphosphine and carbon tetrachloride or carbon tetrabromide, and the like may be used. Alternatively, a method of synthesizing an alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of t-butyl ester is performed, formic acid, triethylsilane and the like are sometimes added to reductively trap the by-produced t-butyl cation.

When a dehydration reaction is performed in each step, sulfuric acid, phosphorus pentaoxide, phosphorus oxychloride, N,N'-dicyclohexylcarbodiimide, alumina, polyphosphoric acid and the like are used as the dehydrating agent.

When an alkylation reaction of alcohols, amines, aromatic heterocycle (e.g., imidazole, pyrazole) having an NH group in the ring and the like is performed in each step, optionally substituted alkyl halide (e.g., iodomethane) or an optionally substituted alkyl having an optionally substituted $C_{1-6}$ alkylsulfonyloxy group as a leaving group, an optionally substituted alkyl having a $C_{6-14}$ arylsulfonyloxy group optionally substituted by a $C_{1-6}$ alkyl group, or sodium 2-chloro-2,2-difluoroacetate, 2,2-difluoro-2-(fluorosulfonyl)acetic acid and the like are used as the alkylating agents. In addition, organic lithiums, metal alkoxides, inorganic bases, organic bases and the like are used as the base.

When a fluorination reaction is performed in each step, DAST (diethylaminosulfur trifluoride), bis(2-methoxyethyl) aminosulfur trifluoride and the like are used as fluorinating agents.

When a coupling reaction is performed in each step, Suzuki coupling, Stille coupling, Buchwald coupling, Negishi coupling, Heck reaction, cyanation reaction using copper cyanide or zinc cyanide can be mentioned as the coupling reaction. Reagents used in a coupling reaction such as metal catalyst, phosphine ligand, base and the like, in addition to the aforementioned reagents, can be used according to a method known per se [for example, methods described in J. F. Hartwig, S. Shekhar, Q. Shen, F. Barrios-Landeros, in The Chemistry of Anilines, Z. Rappoport, Ed., Wiley-Intersicence, New York (2007); L. Jiang, S. L. Buchwald, in Metal-Catalyzed Cross-Coupling Reactions, $2^{nd}$ Ed., A. de Meijere, F. Diederich, Eds., Wiley-VCH, Weinheim, Germany (2004); J. F. Hartwig, in Handbook of Organopalladium Chemistry for Organic Synthesis, A. de Meijere, F. Diederich, Eds., Wiley, New York (2002); J. F. Hartwig, in Modern Amination Methods, A. Ricci, Ed., Wiley-VCH, Weinheim, (2000)], or a method analogous thereto.

Examples of the leaving group to be used in each step include a halogen atom (e.g., fluorine atom, chlorine atom, bromine atom, iodine atom), a $C_{1-6}$ alkoxy group (e.g., methoxy etc.), a $C_{6-14}$ aryloxy group (e.g., phenoxy etc.), an optionally substituted acyl-oxy group (e.g., acetyloxy, benzoyloxy etc.), an optionally substituted $C_{1-6}$ alkoxysulfonyloxy group (e.g., methoxysulfonyloxy etc.), an optionally halogenated $C_{1-6}$ alkylsulfonyloxy group [e.g., methanesulfonyloxy, ethanesulfonyloxy, trichloromethanesulfonyloxy, trifluoromethanesulfonyloxy (triflate) etc.], an optionally substituted $C_{6-14}$ arylsulfonyloxy group [e.g., $C_{6-14}$ arylsulfonyloxy group optionally having 1 to 3 substituents selected from $C_{1-6}$ alkyl group (e.g., methyl, ethyl, propyl, isopropyl, butyl, isobutyl, sec-butyl, tert-butyl, pentyl, hexyl etc.), $C_{1-6}$ alkoxy group (e.g., methoxy, ethoxy, propoxy, isopropoxy, butoxy, isobutoxy, sec-butoxy, pentyloxy, hexyloxy etc.) and nitro group and the like; specific examples include benzenesulfonyloxy, m-nitrobenzenesulfonyloxy, p-toluenesulfonyloxy, naphthylsulfonyloxy etc.] and the like.

The production method of compound (I) is described below.

Unless otherwise specified, each symbol in the following reaction formulas is as defined above. The starting compounds are easily commercially available when a specific production method is not described, or can be produced by a method known per se or a method analogous thereto.

The production method of compound (Ia) which is compound (I) wherein ring B group is represented by the following formula (II) is described below.

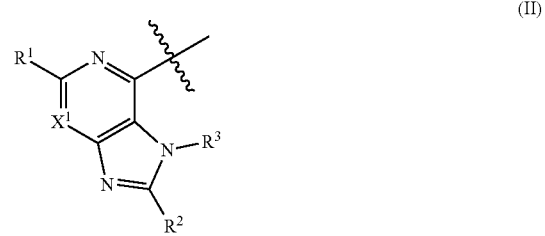

(II)

-continued
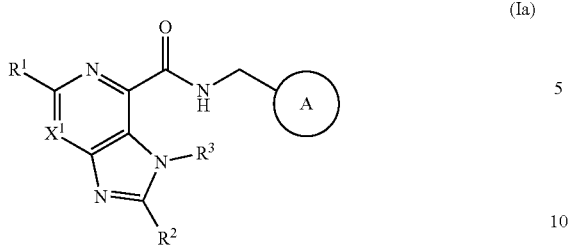
(Ia)
[Production Method 1]
Compound (Ia) wherein $R^3$ is a hydrogen atom can be produced from compound (4) by the method shown in the following Reaction Scheme 1 or a method analogous thereto.
Reaction Scheme 1
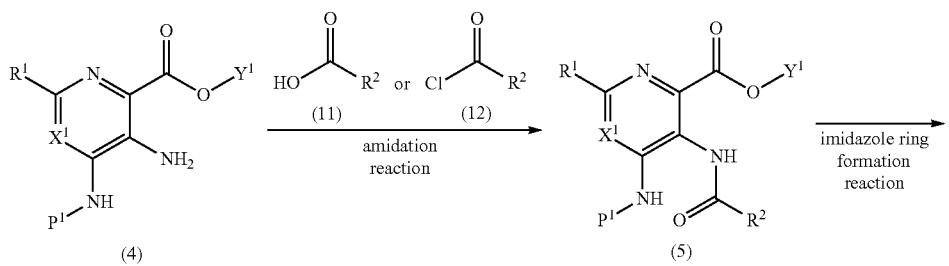
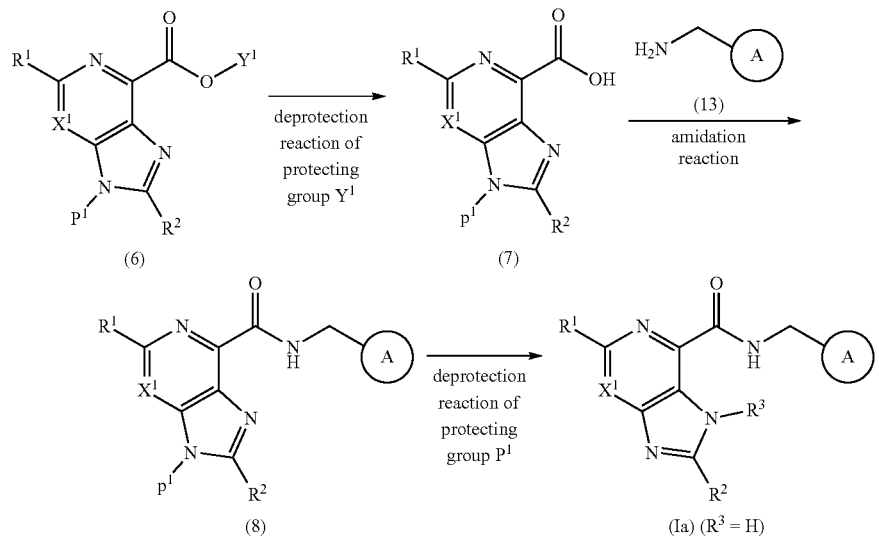
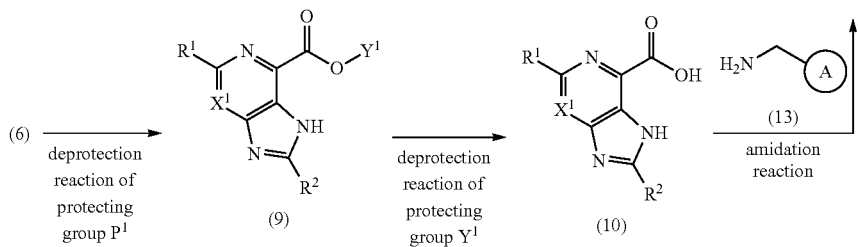

wherein $Y^1$ is a carboxy-protecting group, and $P^1$ is an amino-protecting group.

[Production Method 2]

Compound (Ia) wherein $R^3$ is an optionally substituted hydrocarbon group, or an optionally substituted heterocyclic group can be produced from compound (4) by the method shown in the following Reaction Scheme 2 or a method analogous thereto.

Reaction Scheme 2

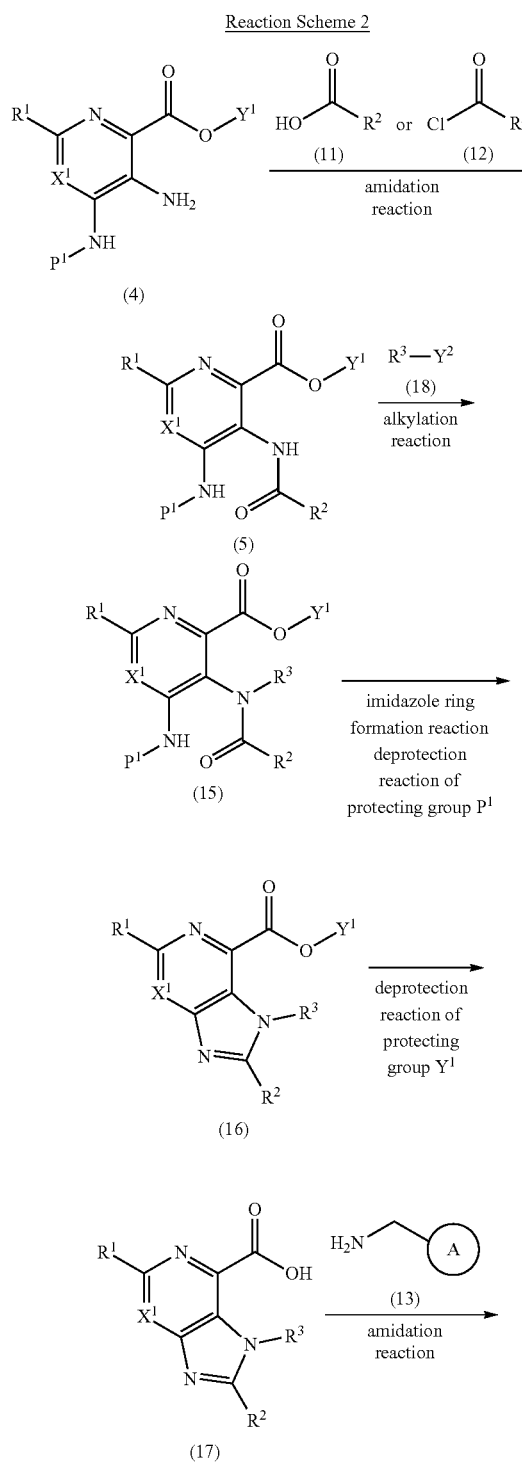

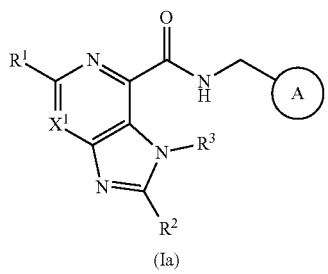

wherein $Y^1$ is a carboxy-protecting group, $Y^2$ is a leaving group, and $P^1$ is an amino-protecting group.

Compound (4) may be commercially available or can also be produced from compound (19) by the method shown in the following Reaction Scheme 3 or a method analogous thereto.

Reaction Scheme 3

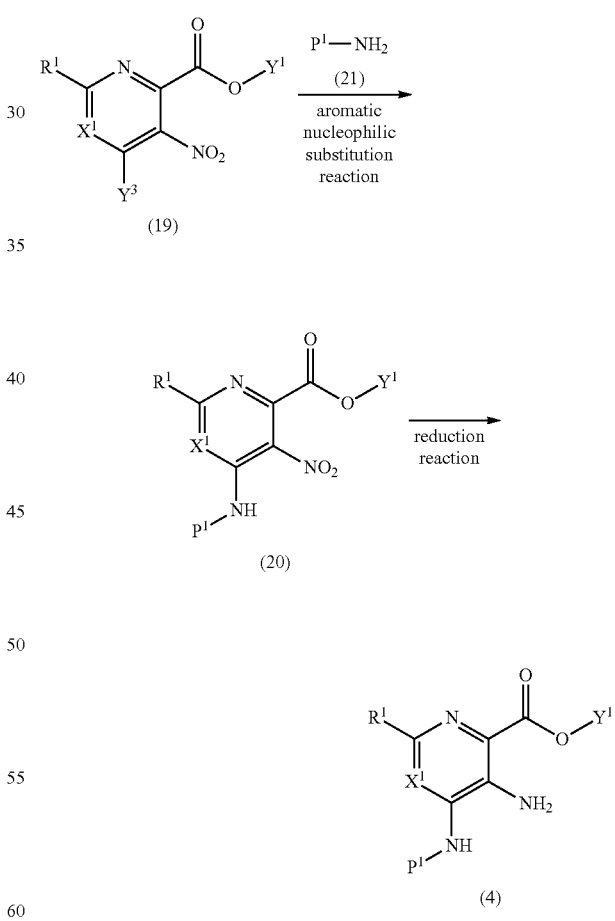

wherein $Y^1$ is a carboxy-protecting group, $Y^3$ is a leaving group, and $P^1$ is an amino-protecting group.

Compound (6) can also be produced from compound (22) by the method shown in the following Reaction Scheme 4 or a method analogous thereto.

Reaction Scheme 4
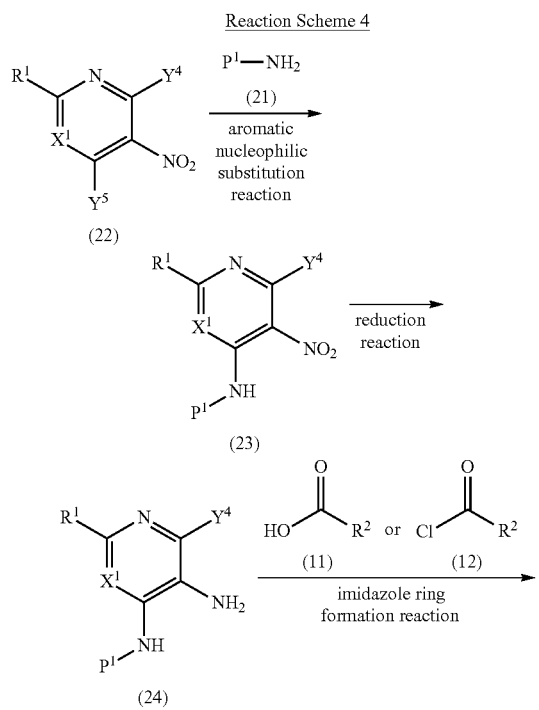
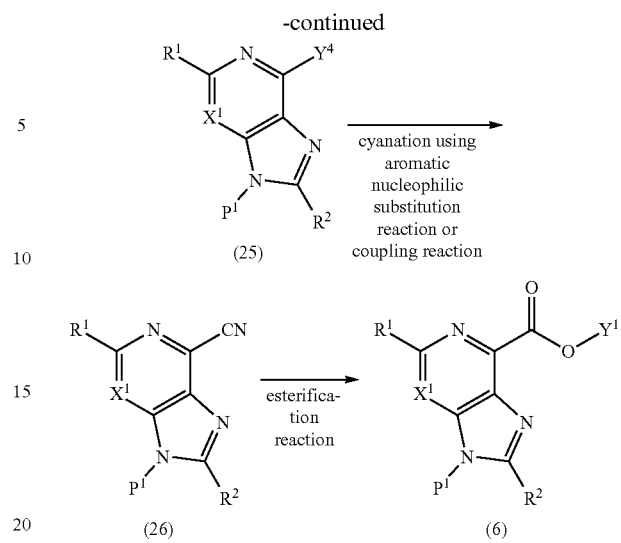
wherein $Y^1$ is a carboxy-protecting group, $Y^4$ and $Y^5$ are leaving groups, and $P^1$ is an amino-protecting group.
Compound (16') which is compound (16) wherein $X^1$ is $CR^4$ can also be produced from compound (27) by the method shown in the following Reaction Scheme 5 or a method analogous thereto.
Reaction Scheme 5
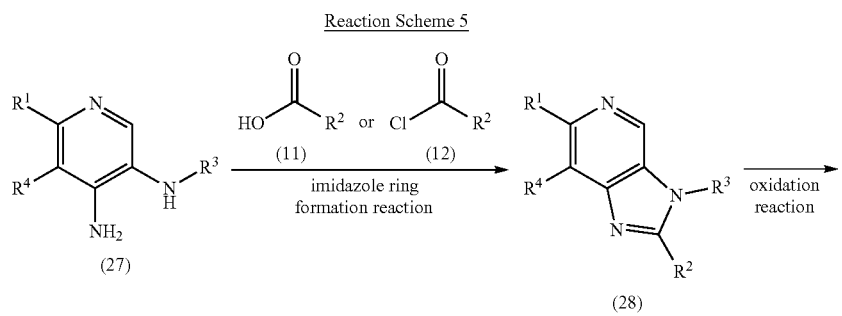
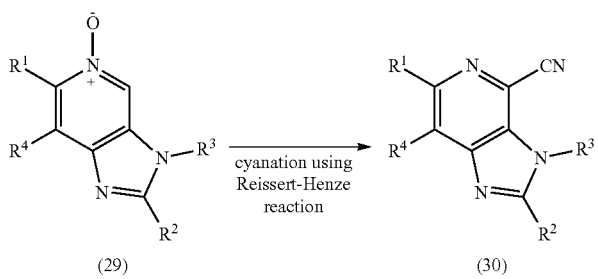

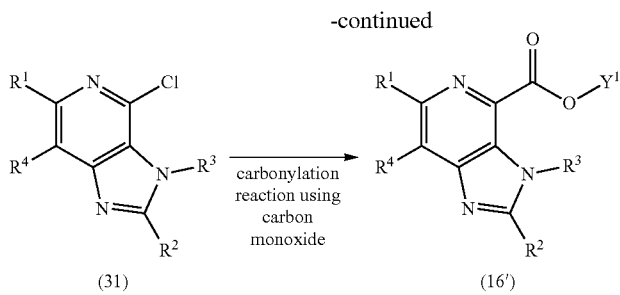

wherein $Y^1$ is a carboxy-protecting group.

When an imidazole ring formation reaction is performed, phosphorus oxychloride, T3P and the like can also be used as the dehydrating reagents. This reaction can also be performed in the presence of an acid or a base.

When an esterification reaction is performed, an alcohol solvent (e.g., methanol etc.) and chlorotrimethylsilane can also be used.

When a Reissert-Henze reaction is performed, acid halide (e.g., dimethylcarbamoyl chloride and the like) and a cyanating agent (e.g., trimethylsilyl cyanide, potassium cyanide, zinc cyanide and the like) are used as the reagents.

When a chlorination reaction is performed, phosphorus oxychloride and the like are used as the chlorinating reagents.

When a carbonylation reaction using carbon monoxide is performed, a metal catalyst, pressurized carbon monoxide, alcohol and the like are used. This reaction can also be performed in the presence of a base.

[Production Method 3]

Compound (Ia) wherein $R^3$ is a hydrogen atom can also be produced from compound (4) by the method shown in the following Reaction Scheme 6 or a method analogous thereto.

Reaction Scheme 6

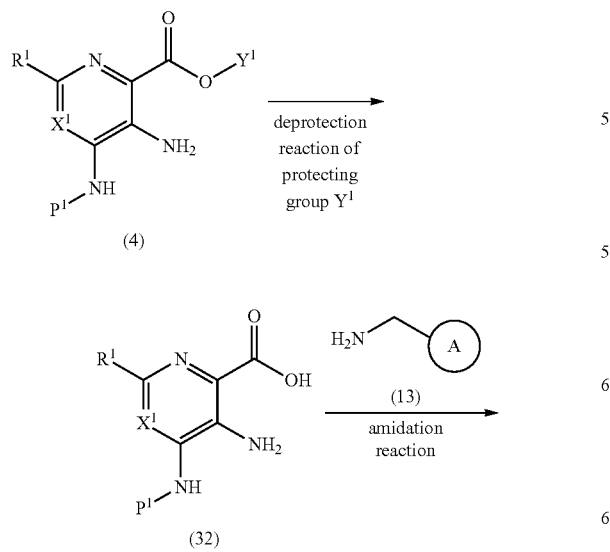

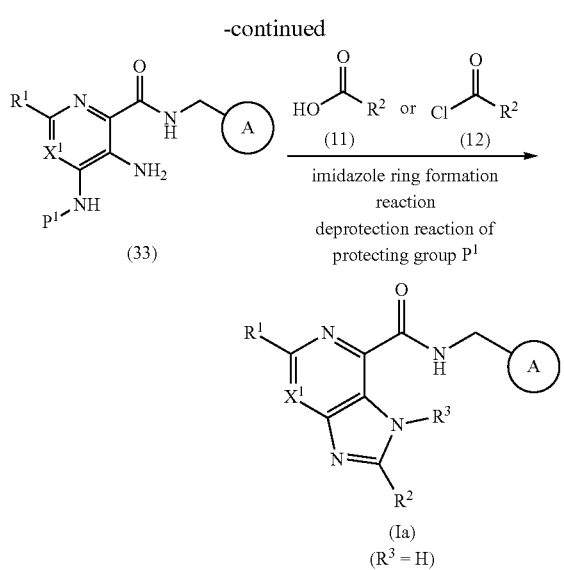

wherein $Y^1$ is a carboxy-protecting group and $P^1$ is an amino-protecting group.

The production method of compound (Ib) which is compound (I) wherein ring B group is represented by the following formula (III) is described below.

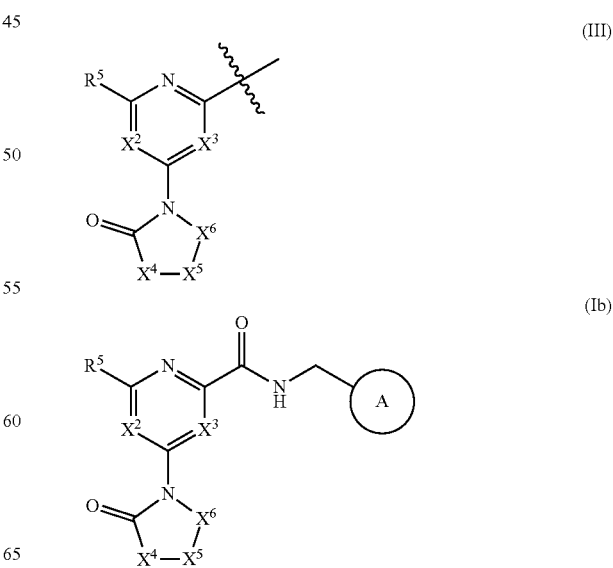

[Production Method 4]

Compound (Ib) can be produced from compound (34) by the method shown in the following Reaction Scheme 7 or a method analogous thereto.

Reaction Scheme 7

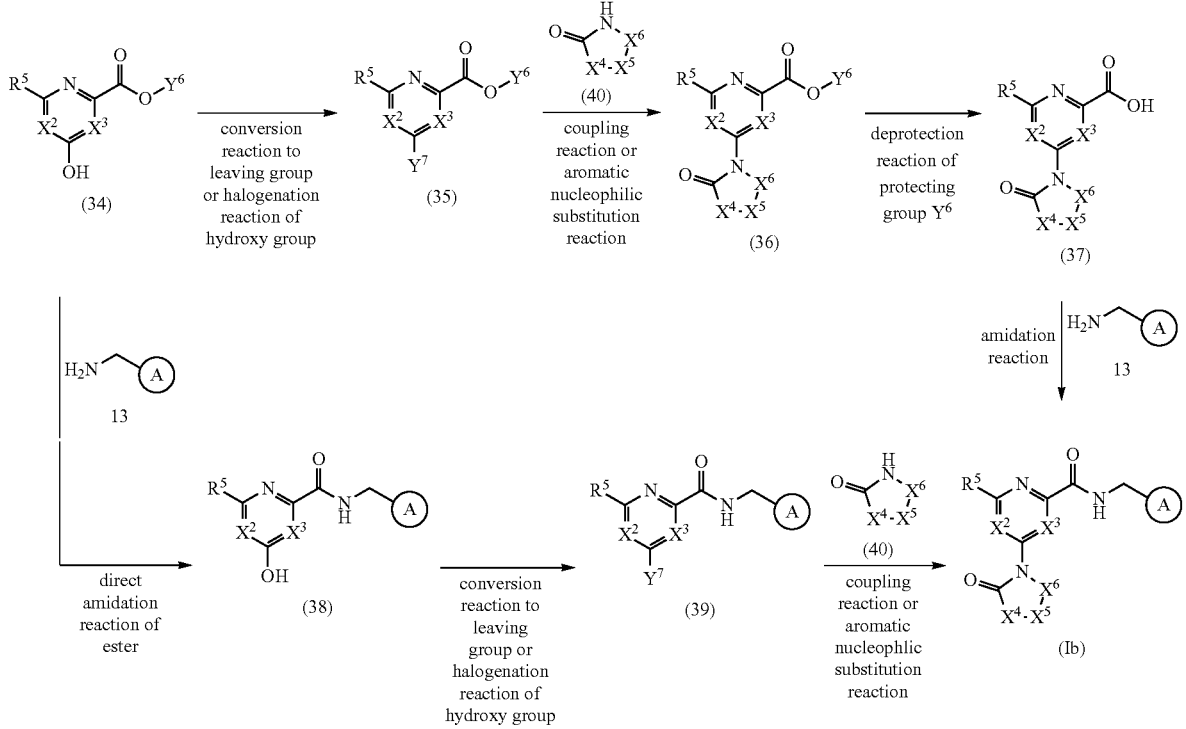

wherein $Y^6$ is a carboxy-protecting group and $Y^7$ is a leaving group.

A conversion reaction to a leaving group is performed by a method known per se, for example, the methods described in "Protective Groups in Organic Synthesis, 4$^{th}$ Ed." Wiley-Interscience 2007 (Theodora W. Greene, Peter G. M. Wuts); "Protecting Groups, 3$^{rd}$ Ed." (P. J. Kocienski) Thieme 2004 and the like, or a method analogous thereto.

Compound (38) can be produced, for example, from compound (34) by a direct amidation reaction of ester. When a direct amidation reaction of ester is performed, compound (13) and an aluminum amide compound prepared from an organic aluminum agent (e.g., trimethylaluminum and the like) are used as the reagents.

Compound (40) may be commercially available or can also be produced by a method known per se (e.g., method described in patent document (WO 2015/016206) and the like) or a method analogous thereto.

The coupling reaction in Production method 1-3 can also be performed in the presence of a phosphine ligand.

Examples of the above-mentioned phosphine ligand include 1,1'-bis(diphenylphosphino)ferrocene, 2,2'-bis(diphenylphosphino)-1,1'-binaphthyl (BINAP), triphenylphosphine, tris(2-methylphenyl)phosphine, bis(diphenylphosphino)ferrocene, 4,5-bis(diphenylphosphino)-9,9-dimethylxanthene (Xantphos) and the like.

Compound (11), compound (12), compound (13), compound (18), and compound (21) may be commercially available, or can also be produced by a method known per se (e.g., the methods described in the Fifth Series of Experimental Chemistry, vol. 13-vol. 19 (The Chemical Society of Japan ed.); Experimental Chemistry, vol. 14-vol. 15 (The Chemical Society of Japan ed.); Fine Organic Chemistry, rev. 2nd edition (L. F. Tietze, Th. Eicher, NANKODO); rev. Organic Name Reaction (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (Kiyoshi Tomioka, supervisor of translation, KAGAKUDOJIN); Comprehensive Organic Transformations (VCH Publishers Inc.) 1989 and the like), or a method analogous thereto.

The substituent of the thus-obtained compound (I) is converted (that is, introduction of a substituent or conversion of a functional group) by applying means known per se to produce another compound or a salt thereof encompassed in compound (I).

As a method for introduction of substituent or conversion of functional group, a known general method is used. For example, conversion of halogen atom (e.g., fluorine, chlorine, bromine, iodine), optionally halogenated $C_{1-6}$ alkylsulfonyl-oxy group [e.g., methanesulfonyloxy, ethanesulfonyloxy, trichloromethanesulfonyloxy, trifluoromethanesulfonyloxy (triflate)] to methyl group, cyclopropyl group, vinyl group, cyano group, formyl group, carbonyl group, carboxyl group, hydroxyl group, amino group, boryl group and the like, conversion of formyl group to ethynyl group by Seyferth-Gilbert homologation reaction, conversion of ester to carboxy group by hydrolysis, conversion of carboxy group to carbamoyl group by amidation, conversion of carboxy group to hydroxymethyl group by reduction, conversion of carbonyl group to alcohol form by reduction or alkylation, reductive amination of carbonyl group, oximation of carbonyl group, acylation of amino group, ureation of amino group, sulfonylation of amino group, alkylation of amino group, substitution or amination of active halogen by amine, alkylation of hydroxy group, substitution or amination of hydroxy group can be mentioned.

In the introduction of substituent and conversion of functional group, when a reactive site possibly causing a reaction other than the desired reaction is present, a protecting group is introduced as necessary into the reactive site in advance by means known per se, the object reaction is performed, and then the protecting group is also removed by means known per se, whereby a compound within the scope of the present invention can also be produced.

When the starting compound and intermediate have an amino group, a carboxy group or a hydroxy group as a substituent, these groups may be protected by a protecting group generally used in the peptide chemistry and the like. In this case, the object compound can be obtained by eliminating the protecting group as necessary after the reaction.

Compound (I) obtained by the above-mentioned production method can be isolated and purified by a known means such as solvent extraction, conversion of solution pH, phase transfer, crystallization, recrystallization and chromatography.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se.

Compound (I) may be a crystal.

A crystal of compound (I) (hereinafter sometimes to be abbreviated as the crystal of the present invention) can be produced by crystallizing compound (I) by applying a crystallization method known per se.

The crystal of the present invention is superior in physicochemical properties (e.g., melting point, solubility, stability) and biological properties (e.g., pharmacokinetics (absorbability, distribution, metabolism, excretion), efficacy expression) and expected to be useful as a medicament.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization methods known per se.

Compound (I) may be a hydrate, non-hydrate, non-solvate or solvate.

Furthermore, compound (I) also encompasses a deuterium conversion form wherein $^1H$ is converted to $^2H(D)$.

Compound (I) may be labeled with an isotope (e.g., $^3H$, $^{13}C$, $^{14}C$, $^{18}F$, $^{35}S$, $^{125}I$) and the like. Compound (I) labeled or substituted with an isotope may be used as, for example, a tracer (PET tracer) used for Positron Emission Tomography (PET), and is expected to be useful in the fields of medical diagnosis and the like.

Compound (I) may be used as a prodrug.

The prodrug of compound (I) is a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or tert-butylation);

a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation);

a compound obtained by subjecting a carboxy group in compound (I) to esterification or amidation (e.g., a compound obtained by subjecting a carboxy group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

In the present specification, the prodrug may form a salt. Examples of such salt include those exemplified as the salt of the aforementioned compound represented by the formula (I).

Compound (I) or a prodrug thereof (hereinafter sometimes to be simply abbreviated as the compound of the present invention) has a PRS inhibitory activity and may be useful as a prophylactic or therapeutic agent for cancer, a cancer proliferation inhibitor, or a cancer metastasis inhibitor.

The compound of the present invention shows a selective inhibitory activity against PRS. In addition, since the compound of the present invention is also superior in efficacy expression, pharmacokinetics (e.g., absorbability, distribution, metabolism, excretion), solubility (e.g., water-solubility), interaction with other pharmaceutical products (e.g., drug-metabolizing enzyme inhibitory action), safety (e.g., acute toxicity, chronic toxicity, genetic toxicity, reproductive toxicity, heart toxicity, carcinogenicity, central nervous system toxicity), and stability (e.g., chemical stability, stability against enzyme), it may be useful as a medicament.

Therefore, the compound of the present invention may be used for inhibiting an excessive (abnormal) PRS action on mammals (e.g., mouse, rat, hamster, rabbit, cat, dog, bovine, sheep, monkey, human).

The compound of the present invention is expected to be useful for the prophylaxis or treatment of diseases possibly influenced by PRS (sometimes to be abbreviated as "PRS associated disease" in the present specification), for example, cancer [e.g., colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell type renal cell carcinoma), transitional cell carcinoma in kidney and ureter), uterine cancer (e.g., cervixcancer, uterine body cancer, uterus sarcoma), gestational choriocarcinoma, brain tumor (e.g., medulloblastoma, glioma, pineal astrocytoma, pilocytic astrocytoma, diffuse astrocytoma, anaplastic astrocytoma, hypophyseal adenoma), retina blastoma, skin cancer (e.g., basalioma, malignant melanoma (melanoma)), sarcoma (e.g., rhabdomyosarcoma, leiomyosarcoma, soft tissue sarcoma, spindle cell sarcoma, osteosarcoma), malignant bone tumor, urinary bladder cancer, hematologic cancer (e.g., multiple myeloma, leukemia (e.g., acute myeloid leukemia, acute lymphocytic leukemia), malignant lymphoma, Hodgkin's disease, chronic myeloproliferative disease), cancer of unknown primary], inhibiting proliferation of cancer, suppression of metastasis, promotion of apoptosis, or prophylaxis or treatment of precancerous lesion (e.g., myelodysplastic syndrome). In addition, the compound of the present invention is expected to be useful for the prophylaxis or treatment of scleroderma, cirrhosis, idiopathic pulmonary fibrosis, inflammatory bowel disease or muscular dystrophy.

Also, the compound of the present invention is expected to be useful for the prophylaxis or treatment of malaria.

The compound of the present invention may be administered orally or parenterally to a mammal (preferably, human) as it is or as a medicament mixed with a pharmacologically acceptable carrier.

A medicament containing the compound of the present invention (sometimes to be abbreviated as "the medicament of the present invention") is described in detail below. Examples of the dosage form of the medicament of the present invention include oral preparations such as tablet (e.g., sugar-coated tablet, film-coated tablet, sublingual tablet, buccal, orally quick-integrating tablet), pill, granule, powder, capsule (e.g., soft capsule, microcapsule), syrup, emulsion, suspension, film (e.g., orally disintegrable film, mouth cavity mucosa patch film) and the like. Also, examples of the dosage form of the medicament of the present invention include parenteral agents such as injection, drip transfusion, transdermal agent (e.g., Iontophoresis transdermal preparation), suppository, ointment, nasal preparation, pulmonary preparation, eye drop and the like. The medicament of the present invention may be a controlled-release preparation such as immediate-release preparation, sustained-release preparation (e.g., sustained-release microcapsule) and the like.

The medicament of the present invention may be produced by a known production method (e.g., the method described in the Japanese Pharmacopoeia) generally used in the technical field of preparation formulations. The medicament of the present invention can contain, where necessary, an appropriate amount of an additive generally used in the pharmaceutical field such as excipient, binder, disintegrant, lubricant, sweetening agent, surfactant, suspending agent, emulsifier, colorant, preservative, aromatic, corrigent, stabilizer, thickening agent and the like.

These additives can be recited as the aforementioned pharmacologically acceptable carrier.

For example, tablet may be produced using excipient, binder, disintegrant, lubricant and the like, and pill and granule may be produced using excipient, binder, disintegrant. In addition, powder and capsule may be produced using excipient and the like, syrup may be produced using sweetening agent and the like, and emulsion and suspension may be produced using suspending agent, surfactant, emulsifier and the like.

Examples of the excipient include lactose, sucrose, glucose, starch, saccharose, microcrystalline cellulose, *Glycyrrhiza uralensis*, mannitol, sodium hydrogen carbonate, calcium phosphate, calcium sulfate.

Examples of the binder include 5 to 10 wt % starch glue solution, 10 to 20 wt % gum arabic solution or gelatin solution, 1 to 5 wt % tragacanth solution, carboxymethylcellulose solution, sodium alginate solution, glycerol.

Examples of the disintegrant include starch, calcium carbonate.

Examples of the lubricant include magnesium stearate, stearic acid, calcium stearate, purified talc.

Examples of the sweetening agent include glucose, fructose, invert sugar, sorbitol, xylitol, glycerol, simple syrup.

Examples of the surfactant include sodium lauryl sulfate, polysorbate 80, sorbitan monofatty acid ester, polyoxyl stearate 40.

Examples of the suspending agent include gum arabic, sodium alginate, sodium carboxymethylcellulose, methylcellulose, bentonite.

Examples of the emulsifier include gum arabic, tragacanth, gelatin, polysorbate 80.

For example, when the medicament of the present invention is a tablet, the tablet may be produced according to a method known per se by adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol 6000) to the compound of the present invention, compression molding the mixture and, where necessary, applying a coating for the purpose of taste masking, enteric property or sustainability by a coating method known per se. As the coating agent used for the coating, hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) and dye (e.g., red iron oxide, titanium dioxide) may be used.

The aforementioned injection includes intravenous injection, subcutaneous injection, intradermal injection, muscular injection, intraperitoneal injection, drip injection and the like.

Such injection may be prepared by a method known per se, that is, by dissolving, suspending or emulsifying the compound of the present invention in an aseptic aqueous solution or oily solution. Examples of the aqueous solution include saline, isotonic solution (e.g., D-sorbitol, D-mannitol, sodium chloride) containing glucose and other auxiliary agents and the like. The aqueous solution may contain suitable solubilizing agents, for example, alcohol (e.g., ethanol), polyalcohol (e.g., propylene glycol, polyethylene glycol), non-ionic surfactant (e.g., polysorbate 80, HCO-50). Examples of the oily solution include sesame oil, soybean oil and the like. The oily solution may contain a suitable solubilizing agent. Examples of the solubilizing agent include benzyl benzoate, benzyl alcohol and the like. The injection may contain buffering agent (e.g., phosphate buffer, sodium acetate buffer), soothing agent (e.g., benzalkonium chloride, procaine hydrochloride), stabilizer (e.g., human serum albumin, polyethylene glycol), preservative (e.g., benzyl alcohol, phenol) and the like. An injection thus prepared may be generally filled in an ampoule.

While the content of the compound of the present invention in the medicament of the present invention varies depending on the preparation form, it is generally about 0.01-about 100 wt %, preferably about 2-about 85 wt %, further preferably about 5-about 70 wt %, relative to the whole preparation.

While the content of the additive in the medicament of the present invention varies depending on the preparation form, it is generally about 1 to about 99.9 wt %, preferably about 10 to about 90 wt %, relative to the whole preparation.

The compound of the present invention is stable, low toxic and may be used safely. While the daily dose of the compound of the present invention varies depending on the condition and body weight of the patients, kind of the compound, administration route and the like, when, for example, it is orally administered to patients for treating cancer, the dose for an adult (body weight about 60 kg) per day is about 1 to about 1000 mg, preferably about 3 to about 300 mg, further preferably about 10 to about 200 mg, based on the compound of the present invention, which may be administered in one or two or three portions.

When the compound of the present invention is parenterally administered, it is generally administered in the form of a liquid (e.g., injection). While a single dose of the compound of the present invention varies depending on the subject of administration, target organ, symptom, administration method and the like, for example, it is generally preferable to administer about 0.01 to about 100 mg, preferably about 0.01 to about 50 mg, more preferably about 0.01 to about 20 mg, of the compound of the present invention per 1 kg body weight by intravenous injection.

The compound of the present invention may be used in combination with other drugs. Specifically, the compound of the present invention may be used in combination with drugs such as hormonal therapeutic agent, chemotherapeutic agent, immunotherapeutic agent or medicament inhibiting actions of cell growth factor and receptor thereof and the like. In the following, a drug that can be used in combination with the compound of the present invention is to be abbreviated as a "concomitant drug".

As the "hormonal therapeutic agent", for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testrolactone, aminoglutethimide, LH-RH agonist (e.g., goserelin acetate, buserelin, leuprorelin acetate), droloxifene, epitiostanol, ethinylestradiol sulfonate, aromatase inhibitor (e.g., fadrozole hydrochloride, anastrozole, retrozole, exemestane, vorozole, formestane), anti-androgen (e.g., flutamide, bicartamide, nilutamide, enzalutamide), 5α-reductase inhibitor (e.g., finasteride, epristeride, dutasteride), adrenocortical hormone drug (e.g., dexamethasone, predonisolone, betamethasone, triamcinolone), androgen synthesis inhibitor (e.g., abiraterone), retinoid and drugs that retard retinoid metabolism (e.g., liarozole), thyroid gland hormone, and DDS (Drug Delivery System) preparation thereof are used.

As the "chemotherapeutic agent", for example, alkylating agents, metabolic antagonists, antitumor antibiotics, and plant-derived antitumor drugs may be used.

As the "alkylating agent", for example, nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof may be used.

As the "metabolic antagonist", for example, mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurin, ambamustine, bendamustine, and DDS preparations thereof may be used.

As the "antitumor antibiotic", for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS preparations thereof (e.g., Doxorubicin encapsulated PEG ribosome) may be used.

As the "plant-derived antitumor drug", for example, etoposide, etoposide phosphate, vinblastine sulfate, vincristine sulfate, vindesine sulfate, teniposide, paclitaxel, docetaxel, cabazitaxel, vinorelbine, and DDS preparations thereof may be used.

As the "immunotherapeutic agent", for example, picibanil, krestin, schizophyllan, lentinan, ubenimex, interferon, interleukin, macrophage colony stimulating factor, granulocyte colony stimulating factor, erythropoietin, lymphotoxin, BCG vaccine, *Corynebacterium parvum*, levamisole, polysaccharide K, procodazole, anti-CTLA4 antibody (e.g., ipilimumab, tremelimumab), anti-PD-1 antibody (e.g., nivolumab, pembrolizumab), anti-PD-L1 antibody may be used.

The "cell growth factors" in the "medicament inhibiting actions of cell growth factor and receptor thereof" may be any substance that promotes cell proliferation, which is normally peptide having not more than 20,000 molecular weight, and capable of exhibiting the activity at low concentrations by binding to a receptor, and specifically (1) EGF (epidermal growth factor) or substances possessing substantially the same activity as EGF (e.g., TGFα);
(2) insulin or substances possessing substantially the same activity as insulin (e.g., insulin, IGF (insulin-like growth factor)-1, IGF-2),
(3) FGF (fibroblast growth factor) or substances possessing substantially the same activity as FGF (e.g., acidic FGF, basic FGF, KGF (keratinocyte growth factor), FGF-10), and
(4) other cell growth factors (e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin); may be used.

The "cell growth factor receptor" may be any receptor capable of binding to the aforementioned cell growth factors, and specifically, EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor, and the like may be used.

As the "medicament inhibiting actions of cell growth factor and receptor thereof", for example, EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, ROR1 inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor, PI3K inhibitor, and the like may be used. More specifically, anti-VEGF antibody (e.g., Bevacizumab, Ramucurumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1 (R)-phenylethyl]-7H-pyrrolo[2,3-d]pyrimidin-4-amine (AEE-788), Vandetanib, Temsirolimus, Everolimus, Enzastaurin, Tozasertib, 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-difluorophenyl)-5H-primido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), Volasertib, Selumetinib, Trametinib, N-[2 (R),3-dihydroxypropoxy]-3,4-difluoro-2-(2-fluoro-4-iodophenylamino)benzamide (PD-0325901), Bosutinib, Regorafenib, Afatinib, Idelalisib, Ceritinib, Dabrafenib, and the like may be used.

Besides the above-mentioned drugs, asparaginase, aceglatone, procarbazine hydrochloride, protoporphyrin-cobalt complex salt, mercuric hematoporphyrin-sodium, topoisomerase I inhibitor (e.g., irinotecan, topotecan, indotecan, Indimitecan), topoisomerase II inhibitor (e.g., sobuzoxane), differentiation-inducing factor (e.g., retinoid, vitamin D), other angiogenesis inhibitor (e.g., fumagillin, shark extract, COX-2 inhibitor), α-blocker (e.g., tamsulosin hydrochloride), bisphosphonic acid (e.g., pamidronate, zoledronate), thalidomide, lenalidomide, pomalidomide, 5-azacytidine, decitabine, proteasome inhibitor (e.g., bortezomib, carfilzomib, ixazomib), NEDD8 inhibitor (e.g., Pevonedistat), UAE inhibitor, PARP inhibitor (e.g., Olaparib, Niraparib, Veliparib), antitumor antibodies such as anti-CD20 antibody (e.g., Rituximab, Obinutuzumab), anti-CCR4 antibody (e.g., Mogamulizumab) and the like, antibody drug complex (e.g., trastuzumab emtansine, brentuximab vedotin), and the like may also be used as a concomitant drug.

By combining the compound of the present invention and a concomitant drug, superior effects such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer, (4) a sustained treatment effect can be designed, (5) a synergistic effect can be afforded by a combined use of the compound of the present invention and a concomitant drug, and the like, can be achieved.

In the following, the compound of the present invention and a concomitant drug used in combination are referred to as the "combination agent of the present invention".

When the combination agent of the present invention is administered, the administration period is not limited and the compound of the present invention and the concomitant drug may be administered simultaneously, or may be administered at a time interval. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

The dose of the concomitant drug may be appropriately determined based on the dose employed in clinical situations. The mixing ratio of the compound of the present invention and a concomitant drug may be appropriately determined depending on the administration subject, administration route, target disease, symptom, combination and the like. For example, when the subject of administration is a human, 0.01 to 100 parts by weight of a concomitant drug may be used per 1 part by weight of the compound of the present invention.

Furthermore, the compound of the present invention or the combination agent of the present invention may be used in combination with a non-drug therapy. Specifically, the compound of the present invention or the combination agent of the present invention may be combined with a non-drug therapy such as (1) surgery, (2) pressurized chemotherapy using angiotensin II and the like, (3) gene therapy, (4) hyperthermic therapy, (5) cryotherapy, (6) laser cautery method, (7) radiation therapy.

For example, using the compound of the present invention or the combination agent of the present invention before or after the aforementioned surgery or the like, or before or after a treatment combining two or three kinds of these, effects such as prevention of resistance expression, elongation of disease-free period (Disease-Free Survival), suppression of cancer metastasis or recurrence, life-prolongation and the like may be achieved.

In addition, a treatment by the compound of the present invention or the combination agent of the present invention and a supporting therapy [(i) administration of various antibiotics (e.g., β-lactams such as pansporin and the like, macrolides such as clarithromycin and the like) for combination of infectious diseases, (ii) administration of intravenous hyperalimentation, amino acid preparation, general vitamin preparation for improvement of malnutrition, (iii) administration of morphine for relieving pain, (iv) administration of medicaments that improve side effects such as nausea, vomiting, anorexia, diarrhea, leucopenia, thrombocytopenia, hemoglobin concentration reduction, hair loss, hepatopathy, renopathy, DIC, fever and the like and (v) administration of medicaments that suppress resistance of cancer to multiple drugs] may also be combined.

EXAMPLES

The present invention is further explained in detail by referring to the following Examples, Experimental Examples and Formulation Examples which do not limit the present invention and may be changed without departing from the scope of the present invention.

The "room temperature" in the following Examples indicates the range of generally from about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel, the indication of Diol means use of 3-(2,3-dihydroxypropoxy)propylsilane-bonded silica gel, and the indication of DiNH means use of N-(2-aminoethyl)-3-aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

In Examples, the following abbreviations are used.
mp: melting point
MS: mass spectrum
$[M+H]^+$, $[M-H]^-$: molecular ion peak
M: mol concentration
N: normal
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electron spray ionization
APCI: atmospheric pressure chemical ionization
IPE: isopropyl ether
DIEA: diisopropylethylamine
DME: 1,2-dimethoxyethane
DMF: N,N-dimethylformamide
HATU: 2-(7-azabenzotriazol-1-yl)-1,1,3,3-tetramethyluronium hexafluorophosphate
LAH: lithium aluminum hydride
$Pd_2(dba)_3$: tris(dibenzylideneacetone)dipalladium(0)
$PdCl_2(dppf)$: [1,1'-bis(diphenylphosphino)ferrocene]palladium(II) dichloride
SFC: supercritical fluid chromatography, supercritical fluid chromatography
TEA: triethylamine
THF: tetrahydrofuran
TFA: trifluoroacetic acid
T3P: 2,4,6-tripropyl-1,3,5,2,4,6-trioxatriphosphorinane-2,4,6-trioxide
Xantphos: 4,5-bis(diphenylphosphino)-9,9-dimethylxanthene $^1$H NMR was measured by Fourier-transform NMR. For the analysis, ACD/SpecManager (trade name) and the like were used. Very mild peaks for protons of a hydroxy group, an amino group and the like are not described.

MS was measured by LC/MS. As the ionization method, ESI method, or APCI method was used. The data indicates those found. Generally, molecular ion peak ($[M+H]^+$, $[M-H]^-$ and the like) is observed; however, when the compound has a tert-butoxycarbonyl group, a peak after elimination of a tert-butoxycarbonyl group or tert-butyl group may be observed as a fragment ion. When the compound has a hydroxyl group, a peak after elimination of $H_2O$ may be observed as a fragment ion. In the case of a salt, a molecular ion peak or fragment ion peak of free form is generally observed.

The unit of sample concentration (c) in optical rotation ($[α]_D$) is g/100 mL.

The elemental analytical value (Anal.) indicates Calculated value (Calcd) and measured value (Found).

Example 2

8-cyclopentyl-N-(3-fluoro-5-(1-methyl-1H-pyrazol-4-yl)benzyl)-7H-purine-6-carboxamide A) 6-chloro-N-(4-methoxybenzyl)-5-nitropyrimidin-4-amine To a mixture of 4,6-dichloro-5-nitropyrimidine (10.0 g), TEA (5.40 mL) and THF (70 mL) was added a mixture of (4-methoxyphenyl)methanamine (6.67 mL) and THF (30 mL) at 0° C. The reaction mixture was stirred at the same temperature for 30 min. To the reaction mixture was added water at the same temperature, and insoluble material was filtered off. The filtrate was extracted with ethyl acetate, and the organic layer was washed with water and saturated brine and dried over anhydrous sodium sulfate. The solvent was evaporated under reduced pressure. The residue was purified by silica gel column chromatography (ethyl acetate/hexane) to give the title compound (10.0 g).

MS: [M+H]$^+$ 295.0.

B) 6-chloro-N$^4$-(4-methoxybenzyl)pyrimidine-4,5-diamine

To a mixture of 6-chloro-N-(4-methoxybenzyl)-5-nitropyrimidin-4-amine (6.1 g) and acetic acid (200 mL) was added reduced iron (11.56 g) at room temperature. The reaction mixture was stirred at the same temperature for 1 hr 30 min. The insoluble material was filtered off, and the filtrate was concentrated under reduced pressure. To the residue were added ethyl acetate (200 mL) and saturated aqueous sodium hydrogen carbonate solution (200 mL) at 0° C. to adjust pH to 6, and the aqueous layer was extracted with ethyl acetate. The organic layer was washed with water and saturated brine and dried over anhydrous sodium sulfate. The solvent was evaporated under reduced pressure to give the title compound (5.28 g). This compound was used in the next step without further purification.

MS: [M+H]$^+$ 265.2.

C) 6-chloro-8-cyclopentyl-9-(4-methoxybenzyl)-9H-purine

A mixture of 6-chloro-N$^4$-(4-methoxybenzyl)pyrimidine-4,5-diamine (6.1 g), phosphorus oxychloride (45.0 mL) and cyclopentanecarbonyl chloride (2.92 mL) was stirred under a nitrogen atmosphere at 100° C. for 6 hr. The solvent was evaporated under reduced pressure, the residue was diluted with ethyl acetate and water and the mixture was neutralized with saturated aqueous sodium hydrogen carbonate solution. The aqueous layer was extracted with ethyl acetate, and the organic layer was washed with water and saturated brine and dried over anhydrous sodium sulfate. The solvent was evaporated under reduced pressure. The residue was purified by silica gel column chromatography (ethyl acetate/hexane) to give the title compound (5.28 g).

MS: [M+H]$^+$ 343.1.

D) 8-cyclopentyl-9-(4-methoxybenzyl)-9H-purine-6-carbonitrile

To a mixture of 6-chloro-8-cyclopentyl-9-(4-methoxybenzyl)-9H-purine (4.7 g), tetraethylammonium cyanide (4.28 g) and acetonitrile (90 mL) was added 1,4-diazabicyclo[2.2.2]octane (0.615 g) at room temperature. The reaction mixture was stirred at 70° C. for 50 min. The reaction mixture was diluted with ethyl acetate and water, and the aqueous layer was extracted with ethyl acetate. The organic layer was washed with saturated brine and dried over anhydrous sodium sulfate. The solvent was evaporated under reduced pressure. The residue was purified by silica gel column chromatography (ethyl acetate/hexane) to give the title compound (4.27 g).

MS: [M+H]$^+$ 334.1.

E) methyl 8-cyclopentyl-9-(4-methoxybenzyl)-9H-purine-6-carboxylate

To a mixture of 8-cyclopentyl-9-(4-methoxybenzyl)-9H-purine-6-carbonitrile (4.7 g) and methanol (100 mL) was added chlorotrimethylsilane (18 mL) at room temperature. The reaction mixture was stirred at 70° C. overnight. The reaction mixture was poured into saturated aqueous sodium hydrogen carbonate solution, and the aqueous layer was extracted with ethyl acetate. The organic layer was washed with water and saturated brine and dried over anhydrous sodium sulfate. The solvent was evaporated under reduced pressure. The residue was purified by silica gel column chromatography (ethyl acetate/hexane) to give the title compound (3.51 g).

MS: [M+H]$^+$ 367.3.

F) 8-cyclopentyl-9-(4-methoxybenzyl)-9H-purine-6-carboxylic acid

To a mixture of methyl 8-cyclopentyl-9-(4-methoxybenzyl)-9H-purine-6-carboxylate (3.0 g), THF (30 mL) and methanol (30 mL) was added 2N aqueous sodium hydroxide solution (25 mL) at room temperature. The reaction mixture was stirred at the same temperature for 40 min. The reaction mixture was cooled to 0° C., neutralized with 2N hydrochloric acid (25 mL), and the aqueous layer was extracted with ethyl acetate. The organic layer was washed with saturated brine and dried over anhydrous sodium sulfate. The solvent was evaporated under reduced pressure to give the title compound (2.86 g).

MS: [M+H]$^+$ 353.2.

G) 8-cyclopentyl-N-(3-fluoro-5-(1-methyl-1H-pyrazol-4-yl)benzyl)-9-(4-methoxybenzyl)-9H-purine-6-carboxamide A mixture of 8-cyclopentyl-9-(4-methoxybenzyl)-9H-purine-6-carboxylic acid (2.0 g), (3-fluoro-5-(1-methyl-1H-pyrazol-4-yl)phenyl)methanamine hydrochloride (1.65 g), DIEA (2.9 mL), 1.7 M T3P/ethyl acetate solution (10 mL) and ethyl acetate (30 mL) was stirred at 50° C. for 50 min. The reaction mixture was diluted with ethyl acetate and water at 0° C., and the aqueous layer was extracted with ethyl acetate. The organic layer was washed with saturated brine and dried over anhydrous sodium sulfate. The solvent was evaporated under reduced pressure. The residue was purified by silica gel column chromatography (NH, ethyl acetate) to give the title compound (2.32 g).

MS: [M+H]$^+$ 540.2.

H) 8-cyclopentyl-N-(3-fluoro-5-(1-methyl-1H-pyrazol-4-yl)benzyl)-7H-purine-6-carboxamide A mixture of 8-cyclopentyl-N-(3-fluoro-5-(1-methyl-1H-pyrazol-4-yl)benzyl)-9-(4-methoxybenzyl)-9H-purine-6-carboxamide (2.3 g), anisole (5 mL) and TFA (80 mL) was stirred at 85° C. overnight. The solvent was evaporated under reduced pressure, and the residue was diluted with ethyl acetate, saturated aqueous sodium hydrogen carbonate solution. The aqueous layer was extracted with ethyl acetate, and the organic layer was washed with water and saturated brine and dried over anhydrous sodium sulfate. The solvent was evaporated under reduced pressure. The residue was purified by silica gel column chromatography (methanol/ethyl acetate) and recrystallized from ethanol/heptane (1/5, 120 mL) to give the title compound (1.31 g).

$^1$H NMR (300 MHz, DMSO-d$_6$) δ 1.61-2.12 (8H, m), 3.43-3.56 (1H, m), 3.85 (3H, s), 4.57 (2H, d, J=6.3 Hz), 6.95-7.03 (1H, m), 7.26-7.33 (1H, m), 7.42 (1H, s), 7.87 (1H, d, J=0.7 Hz), 8.16 (1H, s), 8.96 (1H, s), 9.67-9.79 (1H, m), 13.16 (1H, brs).

Example 23

N-(3-cyano-5-(1-methyl-1H-pyrazol-4-yl)benzyl)-7-methyl-8-(tetrahydrofuran-2-yl)-7H-purine-6-carboxamide

A) ethyl 6-((2,4-dimethoxybenzyl)amino)-5-(tetrahydrofuran-2-carboxamido)pyrimidine-4-carboxylate To a mixture of tetrahydrofuran-2-carboxylic acid (349 mg), DMF (2 drops) and THF (10 mL) was added oxalyl chloride (0.517 mL) at room temperature. The reaction mixture was stirred at the same temperature for 30 min. The solvent was evaporated under reduced pressure, and the residue was diluted with pyridine (15 mL). The obtained mixture was added to a mixture of ethyl 5-amino-6-((2,4-dimethoxybenzyl)amino)pyrimidine-4-carboxylate (500 mg) and pyridine (15 mL) at room temperature. The reaction mixture was stirred at the same temperature for 2 hr. The reaction mixture was diluted with ethyl acetate, water and saturated aqueous sodium hydrogen carbonate solution, and the aqueous layer was extracted with ethyl acetate. The organic layer was washed with saturated brine and dried over anhydrous sodium sulfate. The solvent was evaporated under reduced pressure to give the title compound (648 mg). This compound was used in the next step without further purification.

MS: [M+H]$^+$ 431.1.

B) ethyl 6-((2,4-dimethoxybenzyl)amino)-5-(N-methyltetrahydrofuran-2-carboxamido)pyrimidine-4-carboxylate To a mixture of ethyl 6-((2,4-dimethoxybenzyl)amino)-5-(tetrahydrofuran-2-carboxamido)pyrimidine-4-carboxylate (648 mg) and DMF (10 mL) were added potassium carbonate (624 mg) and iodomethane (112 μL) at room temperature. The reaction mixture was stirred at the same temperature overnight. To the reaction mixture was added iodomethane (37 μL) at room temperature, and the mixture was stirred at the same temperature for 2 hr. To the reaction mixture was further added iodomethane (19 μL) at room temperature, and the mixture was stirred at the same temperature for 1 hr. The reaction mixture was diluted with ethyl acetate and water, and the aqueous layer was extracted with ethyl acetate. The organic layer was washed with saturated brine and dried over anhydrous sodium sulfate. The solvent was evaporated under reduced pressure. The residue was purified by silica gel column chromatography (NH, ethyl acetate/hexane) to give the title compound (559 mg).

MS: [M+H]$^+$ 445.2.

C) ethyl 7-methyl-8-(tetrahydrofuran-2-yl)-7H-purine-6-carboxylate

A mixture of ethyl 6-((2,4-dimethoxybenzyl)amino)-5-(N-methyltetrahydrofuran-2-carboxamido)pyrimidine-4-carboxylate (559 mg) and phosphorus oxychloride (5 mL) was stirred at 100° C. for 45 min. The insoluble material was filtered off, and the filtrate was concentrated under reduced pressure. The residue was diluted with ethyl acetate and saturated aqueous sodium hydrogen carbonate solution, and the aqueous layer was extracted with ethyl acetate. The organic layer was washed with water and saturated brine and dried over anhydrous sodium sulfate. The solvent was evaporated under reduced pressure. The residue was purified by silica gel column chromatography (NH, ethyl acetate/hexane) to give the title compound (100 mg).

MS: [M+H]$^+$ 277.0.

D) 7-methyl-8-(tetrahydrofuran-2-yl)-7H-purine-6-carboxylic acid

To a mixture of ethyl 7-methyl-8-(tetrahydrofuran-2-yl)-7H-purine-6-carboxylate (99.5 mg), ethanol (2 mL) and THF (2 mL) was added 2N aqueous sodium hydroxide solution (0.5 mL) at 0° C. The reaction mixture was stirred at the same temperature for 20 min. To the reaction mixture was added 2N hydrochloric acid at 0° C. to adjust pH to 6. The solvent was evaporated under reduced pressure and to the residue was added ethanol/methanol mixed solvent (5/1, 20 mL) at 50° C., and insoluble material was filtered off. The filtrate was concentrated under reduced pressure to give the title compound (89 mg).

MS: [M+H]$^+$ 249.0.

E) 3-bromo-5-formylbenzonitrile

To a mixture of 3-formylbenzonitrile (14.5 g) and sulfuric acid (50 mL) was added N-bromosuccinimide (21.65 g) at 60° C. The reaction mixture was stirred at the same temperature for 2 hr. The reaction mixture was poured into water at 0° C., and the precipitate was collected by filtration and washed with hexane to give a solid (22.4 g). To a mixture of the obtained solid (22.4 g), pyridine (35.6 mL) and THF (50.0 mL) was gradually added trifluoroacetic anhydride (31.2 mL) at room temperature. The reaction mixture was stirred at 60° C. overnight. The solvent was evaporated under reduced pressure, and the precipitate was collected by filtration and washed with IPE/hexane mixed solvent to give the title compound (4.73 g).

$^1$H NMR (300 MHz, CDCl$_3$) δ 8.02-8.05 (1H, m), 8.08-8.11 (1H, m), 8.22-8.29 (1H, m), 9.96-10.03 (1H, m).

F) 3-formyl-5-(1-methyl-1H-pyrazol-4-yl)benzonitrile

A mixture of 3-bromo-5-formylbenzonitrile (1.0 g), 1-methyl-4-(4,4,5,5-tetramethyl-1,3,2-dioxaborolan-2-yl)-1H-pyrazole (1.49 g), PdCl$_2$(dppf) (0.174 g), 2 M aqueous potassium carbonate solution (5.95 mL) and DME (15 mL) was stirred under a nitrogen atmosphere at 80° C. for 1 hr 30 min. To the reaction mixture was added water at room temperature, insoluble material was filtered off, and the filtrate was extracted with ethyl acetate/THF. The organic layer was washed with saturated brine and dried over anhydrous sodium sulfate. The solvent was evaporated under reduced pressure. The precipitate was collected by filtration and washed with IPE to give the title compound (0.963 g).

MS: [M+H]$^+$ 212.2.

G) 3-((hydroxyimino)methyl)-5-(1-methyl-1H-pyrazol-4-yl)benzonitrile

A mixture of 3-formyl-5-(1-methyl-1H-pyrazol-4-yl)benzonitrile (650 mg), hydroxylamine hydrochloride (321 mg), sodium hydrogen carbonate (517 mg), ethanol (15 mL) and THF (1.0 mL) was stirred at room temperature for 30 min. To the reaction mixture was added water at room temperature, and the precipitate was collected by filtration, washed with water and ethyl acetate, and dried under reduced pressure to give the title compound (630 mg). This compound was used in the next step without further purification.
MS: [M+H]$^+$ 227.3.

H) 3-(aminomethyl)-5-(1-methyl-1H-pyrazol-4-yl) benzonitrile hydrochloride

A mixture of 3-((hydroxyimino)methyl)-5-(1-methyl-1H-pyrazol-4-yl)benzonitrile (300 mg), zinc (867 mg), acetic acid (10 mL) and water (3.0 mL) was stirred at room temperature overnight. The solvent was evaporated under reduced pressure. To the residue were added ethyl acetate (15 mL), methanol (2 mL) and 4N hydrogen chloride/ethyl acetate solution (3.32 mL) at room temperature and the mixture was stirred at room temperature for 20 min. The precipitate was collected by filtration and washed with ethyl acetate to give the title compound (386 mg).
MS: [M+H]$^+$ 213.3.

I) N-(3-cyano-5-(1-methyl-1H-pyrazol-4-yl)benzyl)-7-methyl-8-(tetrahydrofuran-2-yl)-7H-purine-6-carboxamide A mixture of 7-methyl-8-(tetrahydrofuran-2-yl)-7H-purine-6-carboxylic acid (49 mg), 3-(aminomethyl)-5-(1-methyl-1H-pyrazol-4-yl)benzonitrile hydrochloride (63.8 mg), 1.7 M T3P/ethyl acetate solution (0.348 mL), DIEA (0.172 mL) and DMF (3 mL) was stirred at 70° C. for 2 hr. The solvent was evaporated under reduced pressure, and the residue was purified by silica gel column chromatography (NH, methanol/ethyl acetate) and then silica gel column chromatography (ethyl acetate/hexane). The fractions containing the object product were combined and concentrated under reduced pressure. The residue was purified by HPLC (C18, mobile phase: water/acetonitrile (containing 0.1% TFA)). To the fractions containing the object product was added saturated aqueous sodium hydrogen carbonate solution, and the mixture was extracted with ethyl acetate. The organic layer was dried over anhydrous sodium sulfate and concentrated under reduced pressure to give the title compound (10.0 mg).
$^1$H NMR (300 MHz, DMSO-d$_6$) δ 1.95-2.15 (2H, m), 2.23-2.38 (1H, m), 2.56-2.70 (1H, m), 3.83-3.92 (5H, m), 4.02-4.07 (3H, m), 4.61 (2H, d, J=6.3 Hz), 5.35-5.42 (1H, m), 7.62 (1H, s), 7.91 (1H, s), 7.96-8.00 (2H, m), 8.26 (1H, s), 9.03 (1H, s), 9.70 (1H, t, J=6.2 Hz).

Example 32

8-(1,4-dioxan-2-yl)-N-(3-fluoro-5-(1-methyl-1H-pyrazol-4-yl)benzyl)-7H-purine-6-carboxamide

A) 3-fluoro-5-(1-methyl-1H-pyrazol-4-yl)benzonitrile

A mixture of 3-bromo-5-fluorobenzonitrile (1000 mg), 1-methyl-4-(4,4,5,5-tetramethyl-1,3,2-dioxaborolan-2-yl)-1H-pyrazole (1873 mg), PdCl$_2$(dppf) (183 mg), 2 M aqueous potassium carbonate solution (6.25 mL) and DME (15 mL) was stirred under a nitrogen atmosphere at 80° C. for 1 hr. To the reaction mixture was added water at room temperature, and the aqueous layer was extracted with ethyl acetate. The organic layer was washed with water and saturated brine and dried over anhydrous sodium sulfate. The solvent was evaporated under reduced pressure. The residue was washed with IPE to give the title compound (1040 mg).
MS: [M+H]$^+$ 202.1.

B) 1-(3-fluoro-5-(1-methyl-1H-pyrazol-4-yl)phenyl) methanamine hydrochloride To a mixture of 3-fluoro-5-(1-methyl-1H-pyrazol-4-yl) benzonitrile (712.7 mg) and THF (20 mL) was added LAH (269 mg) at 0° C. The reaction mixture was stirred under a nitrogen atmosphere at room temperature for 30 min. To the reaction mixture were added water (1.08 mL) and 4N aqueous sodium hydroxide solution (0.269 mL) at the same temperature, and the mixture was stirred at room temperature for 30 min. The insoluble material was filtered off, and the filtrate was concentrated under reduced pressure. To the residue were added ethyl acetate (10 mL) and 4N hydrogen chloride/ethyl acetate solution (5 mL), and the precipitate was collected by filtration, washed with ethyl acetate, and dried under reduced pressure to give the title compound (810 mg).
MS: [M+H]$^+$ 206.1.

C) ethyl 2-chloro-6-((2,4-dimethoxybenzyl)amino)-5-nitropyrimidine-4-carboxylate To a mixture of ethyl 2,6-dichloro-5-nitropyrimidine-4-carboxylate (20.17 g) and THF (350 mL) was added sodium hydrogen carbonate (19.11 g) at 0° C. To the reaction mixture was added dropwise a mixture of (2,4-dimethoxyphenyl)methanamine (14.58 g) and THF (50 mL) at 0° C., and the mixture was stirred at 0° C. for 1 hr and at room temperature for 7 hr. To the reaction mixture were added water and ethyl acetate at room temperature, and the aqueous layer was extracted with ethyl acetate. The organic layer was washed with saturated brine and dried over anhydrous sodium sulfate. The solvent was evaporated under reduced pressure. The residue was purified by silica gel column chromatography (ethyl acetate/hexane) to give the title compound (20.20 g).
MS: [M+H]$^+$ 397.0.

D) ethyl 5-amino-2-chloro-6-((2,4-dimethoxybenzyl)amino)pyrimidine-4-carboxylate To a mixture of ethyl 2-chloro-6-((2,4-dimethoxybenzyl) amino)-5-nitropyrimidine-4-carboxylate (19.43 g) and ethanol (700 mL) was gradually added tin (II) chloride (46.4 g) at room temperature. The reaction mixture was stirred at the same temperature for 4 hr 30 min. The solvent was evaporated at 40° C. under reduced pressure, and the residue was ice-cooled. The precipitate was collected by filtration, washed with ice-cooled ethanol, and dried under reduced pressure to give the title compound (15.23 g).
MS: [M+H]$^+$ 367.0.

E) ethyl 5-amino-6-((2,4-dimethoxybenzyl)amino) pyrimidine-4-carboxylate

To a mixture of ethyl 5-amino-2-chloro-6-((2,4-dimethoxybenzyl)amino)pyrimidine-4-carboxylate (4540 mg), 10% palladium carbon (450 mg), ethanol (150 mL) and THF (150 mL) was added ammonium formate (7805 mg) at room temperature. The reaction mixture was stirred at 60° C. for 4 hr. The insoluble material was filtered off, and the filtrate was concentrated under reduced pressure. The residue was collected by filtration and washed with ethyl acetate/hexane to give the title compound (4100 mg).
MS: [M+H]$^+$ 333.1.

F) 5-amino-6-((2,4-dimethoxybenzyl)amino)pyrimidine-4-carboxylic acid

To a mixture of ethyl 5-amino-6-((2,4-dimethoxybenzyl) amino)pyrimidine-4-carboxylate (1646 mg), ethanol (40 mL) and THF (20 mL) was added 2N aqueous sodium hydroxide solution (13 mL) at room temperature. The reaction mixture was stirred at the same temperature for 1 hr. The solvent was evaporated under reduced pressure. To the residue was added 2N hydrochloric acid at 0° C. to adjust pH to 5. The precipitate was collected by filtration, washed with water, and dried under reduced pressure to give the title compound (1369 mg).
MS: [M+H]$^+$ 305.1.

G) 5-amino-6-((2,4-dimethoxybenzyl)amino)-N-(3-fluoro-5-(1-methyl-1H-pyrazol-4-yl)benzyl)pyrimidine-4-carboxamide To a mixture of 5-amino-6-((2,4-dimethoxybenzyl) amino)pyrimidine-4-carboxylic acid (1500 mg), (3-fluoro-5-(1-methyl-1H-pyrazol-4-yl)phenyl)methanamine hydrochloride (1430 mg) and DMF (50 mL) were added HATU (2437 mg) and DIEA (4.30 mL) at room temperature. The reaction mixture was stirred at the same temperature for 24 hr. The reaction mixture was diluted with ethyl acetate and saturated aqueous sodium hydrogen carbonate solution, and the aqueous layer was extracted with ethyl acetate. The organic layer was washed with saturated brine and dried over anhydrous sodium sulfate. The solvent was evaporated under reduced pressure. The residue was purified by silica gel column chromatography (NH, ethyl acetate/hexane) and the obtained solid was washed with ethyl acetate/hexane to give the title compound (1910 mg).
MS: [M+H]$^+$ 492.2.

H) 8-(1,4-dioxan-2-yl)-N-(3-fluoro-5-(1-methyl-1H-pyrazol-4-yl)benzyl)-7H-purine-6-carboxamide A mixture of 5-amino-6-((2,4-dimethoxybenzyl)amino)-N-(3-fluoro-5-(1-methyl-1H-pyrazol-4-yl)benzyl)pyrimidine-4-carboxamide (120 mg), 1,4-dioxane-2-carboxylic acid (81 mg), DIEA (0.213 mL), 1.7 M T3P/ethyl acetate solution (0.431 mL) and THF (2.5 mL) was stirred under microwave irradiation at 150° C. for 4 hr. The solvent was evaporated under reduced pressure, and the residue was purified by silica gel column chromatography (NH, ethyl acetate/hexane) to give an oil (92 mg). A mixture of the obtained oil (92 mg), TFA (3 mL) and ethyl acetate (2 mL) was stirred at room temperature for 3 hr. The solvent was evaporated under reduced pressure, and the residue was diluted with ethyl acetate and saturated aqueous sodium hydrogen carbonate solution, and the aqueous layer was extracted with ethyl acetate. The organic layer was washed with saturated brine and dried over anhydrous sodium sulfate. The solvent was evaporated under reduced pressure. The residue was purified by silica gel column chromatography (ethyl acetate/hexane) to give the title compound (46.0 mg).
$^1$H NMR (300 MHz, DMSO-d$_6$) δ 3.60-3.82 (3H, m), 3.85 (3H, s), 3.87-4.03 (3H, m), 4.58 (2H, d, J=6.2 Hz), 4.99 (1H, d, J=7.3 Hz), 7.00 (1H, d, J=9.2 Hz), 7.28-7.33 (1H, m), 7.42 (1H, s), 7.88 (1H, d, J=0.8 Hz), 8.16 (1H, s), 9.01 (1H, brs), 9.83 (1H, brs), 13.43 (1H, s).

Example 33

8-(1,4-dioxan-2-yl)-N-(3-fluoro-5-(1-methyl-1H-pyrazol-4-yl)benzyl)-7H-purine-6-carboxamide (tR1)

8-(1,4-Dioxan-2-yl)-N-(3-fluoro-5-(1-methyl-1H-pyrazol-4-yl)benzyl)-7H-purine-6-carboxamide (160 mg) was separated by SFC (column: CHIRALCEL ODH (KC003), 20 mmID×250 mmL, manufactured by Daicel Corporation, mobile phase: carbon dioxide/ethanol=700/300), and the fraction containing the object product and having a shorter retention time was concentrated under reduced pressure to give the title compound (43.7 mg).
retention time: 7.33 min (CHIRALCEL ODH (PL028), 4.6 mmID×150 mmL, manufactured by Daicel Corporation, mobile phase: carbon dioxide/ethanol=700/300)
$^1$H NMR (300 MHz, DMSO-d$_6$) δ 3.63-4.03 (9H, m), 4.50-4.66 (2H, m), 4.90-5.05 (1H, m), 6.92-7.06 (1H, m), 7.24-7.35 (1H, m), 7.43 (1H, brs), 7.88 (1H, s), 8.16 (1H, s), 8.99 (1H, brs), 9.87 (1H, brs), 13.20-13.61 (1H, m).

Example 34

8-(1,4-dioxan-2-yl)-N-(3-fluoro-5-(1-methyl-1H-pyrazol-4-yl)benzyl)-7H-purine-6-carboxamide (tR2)

8-(1,4-Dioxan-2-yl)-N-(3-fluoro-5-(1-methyl-1H-pyrazol-4-yl)benzyl)-7H-purine-6-carboxamide (160 mg) was separated by SFC (column: CHIRALCEL ODH (KC003), 20 mmID×250 mmL, manufactured by Daicel Corporation, mobile phase: carbon dioxide/ethanol=700/300) and the fraction containing the object product and having a longer retention time was concentrated under reduced pressure to give the title compound (32.1 mg).
retention time: 8.53 min (CHIRALCEL ODH (PL028), 4.6 mmID×150 mmL, manufactured by Daicel Corporation, mobile phase: carbon dioxide/ethanol=700/300)
$^1$H NMR (300 MHz, DMSO-d$_6$) δ 3.64-4.04 (9H, m), 4.53-4.63 (2H, m), 4.93-5.02 (1H, m), 6.95-7.05 (1H, m), 7.26-7.36 (1H, m), 7.43 (1H, s), 7.88 (1H, s), 8.16 (1H, s), 8.99 (1H, s), 9.86 (1H, brs), 13.44 (1H, brs).

Example 63

N-(3-fluoro-5-(1-methyl-1H-pyrazol-4-yl)benzyl)-7-methyl-8-(tetrahydro-2H-pyran-2-yl)-7H-purine-6-carboxamide A) ethyl 6-((2,4-dimethoxybenzyl)amino)-5-(tetrahydro-2H-pyran-2-carboxamido)pyrimidine-4-carboxylate To a mixture of tetrahydro-2H-pyran-2-carboxylic acid (1000 mg), DMF (2 drops) and THF (20 mL) was added oxalyl chloride (1.30 mL) at room temperature. The reaction mixture was stirred at the same temperature for 30 min. The solvent was evaporated under reduced pressure, and the residue was diluted with THF (5 mL). The obtained mixture was added to a mixture of ethyl 5-amino-6-((2,4-dimethoxybenzyl)amino)pyrimidine-4-carboxylate (1252 mg) and pyridine (50 mL) at room temperature. The reaction mixture was stirred at the same temperature for 3 hr. To the reaction mixture was added methanol at room temperature and the solvent was evaporated under reduced pressure. The residue was diluted with ethyl acetate and saturated aqueous sodium hydrogen carbonate solution, and the aqueous layer was extracted with ethyl acetate. The organic layer was washed with saturated brine and dried over anhydrous sodium sulfate. The solvent was evaporated under reduced pressure. The residue was purified by silica gel column chromatography (NH, ethyl acetate/hexane) to give the title compound (1468 mg).
MS: [M+H]$^+$ 445.1.

B) ethyl 6-((2,4-dimethoxybenzyl)amino)-5-(N-methyltetrahydro-2H-pyran-2-carboxamido)pyrimidine-4-carboxylate To a mixture of ethyl 6-((2,4-dimethoxybenzyl)amino)-5-(tetrahydro-2H-pyran-2-carboxamido)pyrimidine-4-carboxylate (1468 mg) and DMF (15 mL) were added potassium carbonate (1369 mg) and iodomethane (308 μL) at room temperature. The reaction mixture was stirred at the same temperature for 13 hr. The reaction mixture was diluted with ethyl acetate and water, and the aqueous layer was extracted with ethyl acetate. The organic layer was washed with water and saturated brine and dried over anhydrous sodium sulfate. The solvent was evaporated under reduced pressure. The residue was purified by silica gel column chromatography (NH, ethyl acetate/hexane) to give the title compound (1219 mg).

MS: [M+H]$^+$ 459.2.

C) ethyl 7-methyl-8-(tetrahydro-2H-pyran-2-yl)-7H-purine-6-carboxylate

A mixture of ethyl 6-((2,4-dimethoxybenzyl)amino)-5-(N-methyltetrahydro-2H-pyran-2-carboxamido)pyrimidine-4-carboxylate (1219 mg) and phosphorus oxychloride (9.9 mL) was stirred at 100° C. for 6 hr. The solvent was evaporated under reduced pressure, and the residue was diluted with ethyl acetate and saturated aqueous sodium hydrogen carbonate solution, and the aqueous layer was extracted with ethyl acetate. The organic layer was washed with water and saturated brine and dried over anhydrous sodium sulfate. The solvent was evaporated under reduced pressure. The residue was purified by silica gel column chromatography (NH, ethyl acetate/hexane) to give the title compound (424 mg).

MS: [M+H]$^+$ 291.1.

D) 7-methyl-8-(tetrahydro-2H-pyran-2-yl)-7H-purine-6-carboxylic acid

To a mixture of ethyl 7-methyl-8-(tetrahydro-2H-pyran-2-yl)-7H-purine-6-carboxylate (424 mg), ethanol (2 mL) and THF (2 mL) was added 2N aqueous sodium hydroxide solution (1.4 mL) at 0° C. The reaction mixture was stirred at the same temperature for 30 min. To the reaction mixture was added 2N hydrochloric acid at 0° C. to adjust pH to 4. The solvent was evaporated under reduced pressure. To the residue was added ethanol/methanol mixed solvent (5/1, 20 mL) at 50° C., and insoluble material was filtered off. The filtrate was concentrated under reduced pressure to give the title compound (380 mg).

MS: [M+H]$^+$ 263.1.

E) N-(3-fluoro-5-(1-methyl-1H-pyrazol-4-yl)benzyl)-7-methyl-8-(tetrahydro-2H-pyran-2-yl)-7H-purine-6-carboxamide A mixture of 7-methyl-8-(tetrahydro-2H-pyran-2-yl)-7H-purine-6-carboxylic acid (70 mg), (3-fluoro-5-(1-methyl-1H-pyrazol-4-yl)phenyl)methanamine hydrochloride (77 mg), 1.6 M T3P/DMF solution (0.5 mL), TEA (0.186 mL) and DMF (2 mL) was stirred at room temperature for 7 hr. To the reaction mixture were added ethyl acetate and saturated aqueous sodium hydrogen carbonate solution at room temperature, and the aqueous layer was extracted with ethyl acetate. The organic layer was washed with saturated brine and dried over anhydrous sodium sulfate. The solvent was evaporated under reduced pressure. The residue was purified by silica gel column chromatography (NH, ethyl acetate/hexane) to give the title compound (58.0 mg).

$^1$H NMR (300 MHz, DMSO-d$_6$) δ 1.54-1.76 (3H, m), 1.94-2.17 (3H, m), 3.57-3.79 (1H, m), 3.86 (3H, s), 3.93-4.01 (1H, m), 4.02 (3H, s), 4.57 (2H, d, J=6.2 Hz), 4.89 (1H, dd, J=10.2, 2.4 Hz), 7.01 (1H, d, J=6.1 Hz), 7.29-7.35 (1H, m), 7.43 (1H, s, J=2.7 Hz), 7.89 (1H, d, J=0.8 Hz), 8.18 (1H, s), 9.02 (1H, s), 9.65 (1H, t, J=6.0 Hz).

Example 86

2-cyclopentyl-N-(3-fluoro-5-(1-methyl-1H-pyrazol-4-yl)benzyl)-3H-imidazo[4,5-c]pyridine-4-carboxamide A) 2-cyclopentyl-3H-imidazo[4,5-c]pyridine A mixture of pyridine-3,4-diamine (5 g), cyclopentanecarboxylic acid (5.98 mL) and phosphorus pentoxide/methanesulfonic acid solution (Eaton's reagent) (20 mL) was stirred at 100° C. for 3 hr. To the reaction mixture were added ethyl acetate and water at room temperature, the mixture was neutralized with 2N aqueous sodium hydroxide solution at 0° C., and the aqueous layer was extracted with ethyl acetate. The organic layer was washed with water and saturated brine, and dried over anhydrous magnesium sulfate. The solvent was evaporated under reduced pressure. The residue was purified by silica gel column chromatography (Diol, methanol/ethyl acetate) to give the title compound (4.84 g).

MS: [M+H]$^+$ 188.0.

B) 2-cyclopentyl-3H-imidazo[4,5-c]pyridine5-oxide

To a mixture of 2-cyclopentyl-3H-imidazo[4,5-c]pyridine (2.89 g) and ethyl acetate (45 mL) was added m-chloroperoxy benzoic acid (4.57 g) at room temperature. The reaction mixture was stirred at the same temperature for 3 hr. The reaction mixture was purified by silica gel column chromatography (NH, methanol/ethyl acetate) to give the title compound (2.33 g).

MS: [M+H]$^+$ 204.3.

C) 2-cyclopentyl-3H-imidazo[4,5-c]pyridine-4-carbonitrile

A mixture of 2-cyclopentyl-3H-imidazo[4,5-c]pyridine5-oxide (2.33 g), trimethylsilyl cyanide (2.86 mL), dimethylcarbamoyl chloride (2.22 mL), TEA (3.2 mL) and acetonitrile (30 mL) was stirred at 80° C. for 3 hr. The solvent was evaporated under reduced pressure, and the residue was diluted with ethyl acetate, washed with water and saturated brine, and dried over anhydrous magnesium sulfate. The solvent was evaporated under reduced pressure. The precipitate was collected by filtration and washed with ethyl acetate/hexane to give the title compound (1.96 g).

MS: [M+H]$^+$ 213.3.

D) ethyl 2-cyclopentyl-3H-imidazo[4,5-c]pyridine-4-carboxylate

To a mixture of 2-cyclopentyl-3H-imidazo[4,5-c]pyridine-4-carbonitrile (1.0 g) and ethanol (23.6 mL) was added concentrated sulfuric acid (10.1 mL) at room temperature. The reaction mixture was stirred at 80° C. for 5 hr. The reaction mixture was poured into ice water, and the aqueous layer was washed with ethyl acetate. The mixture was neutralized with ice-cooled 8N aqueous sodium hydroxide solution at 0° C. The aqueous layer was extracted with ethyl acetate. The organic layer was dried over anhydrous magnesium sulfate, and the solvent was evaporated under reduced pressure to give the title compound (1.16 g). This compound was used in the next step without further purification.

MS: [M+H]$^+$ 260.3.

E) 2-cyclopentyl-3H-imidazo[4,5-c]pyridine-4-carboxylic acid

To a mixture of ethyl 2-cyclopentyl-3H-imidazo[4,5-c]pyridine-4-carboxylate (1.16 g), THF (6.8 mL) and water (4 mL) was added 4N aqueous lithium hydroxide solution (2.8 mL) at room temperature. The reaction mixture was stirred at the same temperature for 3 hr. The solvent was evaporated under reduced pressure. To the residue were added water and 2N hydrochloric acid at room temperature to adjust pH to 6. The precipitate was collected by filtration, washed with water, and dried under reduced pressure to give the title compound (0.765 g).

MS: [M+H]$^+$ 232.0.

F) 2-cyclopentyl-N-(3-fluoro-5-(1-methyl-1H-pyrazol-4-yl)benzyl)-3H-imidazo[4,5-c]pyridine-4-carboxamide A mixture of 2-cyclopentyl-3H-imidazo[4,5-c]pyridine-4-carboxylic acid (70 mg), (3-fluoro-5-(1-methyl-1H-pyrazol-4-yl)phenyl)methanamine hydrochloride (95 mg), DIEA (0.257 mL), 1.7 M T3P/ethyl acetate solution (0.534 mL) and ethyl acetate (3 mL) was stirred at 60° C. for 2 hr 30 min. The solvent was evaporated under reduced pressure, and the residue was purified by silica gel column chromatography (NH, ethyl acetate/hexane), and then by silica gel column chromatography (methanol/ethyl acetate). The fractions containing the object product were combined and concentrated under reduced pressure, and the residue was purified by HPLC (C18, mobile phase: water/acetonitrile (containing 0.1% TFA)). To the fractions containing the object product was added saturated aqueous sodium hydrogen carbonate solution, and the mixture was extracted with ethyl acetate. The organic layer was dried over anhydrous sodium sulfate and concentrated under reduced pressure to give the title compound (47.3 mg).

$^1$H NMR (300 MHz, DMSO-d$_6$) δ 1.51-2.18 (8H, m), 3.42-3.57 (1H, m), 3.86 (3H, brs), 4.48-4.71 (2H, m), 6.99 (1H, d, J=8.3 Hz), 7.30 (1H, d, J=9.6 Hz), 7.43 (1H, brs), 7.62-7.82 (1H, m), 7.88 (1H, brs), 8.16 (1H, brs), 8.33 (1H, d, J=4.5 Hz), 9.53 (1H, brs), 12.72 (1H, brs).

Example 159

4-((3S)-3-cyano-3-cyclopropyl-2-oxopyrrolidin-1-yl)-N-(3-fluoro-5-(1-methyl-1H-pyrazol-4-yl)benzyl)-6-methylpyridine-2-carboxamide

A) 4-bromo-6-methylpicolinic acid

To a mixture of 4-bromo-2-methylpyridine (20 g) and acetonitrile (200 mL) were added sulfuric acid (4.56 g), formamide (52.4 g) and water (40 mL) at room temperature. To the mixture was gradually added ammonium peroxodisulfate (39.8 g) at 70° C., and the mixture was stirred at 75° C. for 4 hr. The reaction mixture was cooled to room temperature, diluted with water (150 mL) and neutralized with saturated aqueous sodium hydrogen carbonate solution, and the aqueous layer was extracted with ethyl acetate. The organic layer was washed with water and saturated brine and dried over anhydrous sodium sulfate. The solvent was evaporated under reduced pressure. The residue was collected by filtration and washed with ethyl acetate/hexane mixed solvent to give a solid (15.4 g). A mixture of the obtained solid (15.4 g) and 2N aqueous sodium hydroxide solution (286 mL) was stirred at 100° C. for 40 min. To the reaction mixture was added 6N hydrochloric acid at 0° C. to adjust pH to 4. The solvent was evaporated under reduced pressure. To the residue was added methanol (700 mL), insoluble material was filtered off, and the filtrate was concentrated under reduced pressure. The residue was collected by filtration and washed with ethyl acetate to give the title compound (15.5 g). This compound was used in the next step without further purification.

MS: [M+H]$^+$ 215.9.

B) tert-butyl 4-bromo-6-methylpicolinate

To a mixture of 4-bromo-6-methylpicolinic acid (15.5 g) and tert-butyl alcohol (400 mL) were added pyridine (28.9 mL) and p-toluenesulfonyl chloride (41.0 g) at room temperature. The reaction mixture was stirred at room temperature for 24 hr. The solvent was evaporated under reduced pressure, and the residue was diluted with ethyl acetate and saturated aqueous sodium hydrogen carbonate solution, and the aqueous layer was extracted with ethyl acetate. The organic layer was washed with saturated brine and dried over anhydrous sodium sulfate. The solvent was evaporated under reduced pressure. The residue was purified by silica gel column chromatography (ethyl acetate/hexane) to give the title compound (9.48 g).

$^1$H NMR (300 MHz, DMSO-d$_6$) δ 1.55 (9H, s), 2.52 (3H, s), 7.82 (1H, d, J=1.7 Hz), 7.94 (1H, s).

C) tert-butyl 4-((3S)-3-cyano-3-cyclopropyl-2-oxopyrrolidin-1-yl)-6-methylpicolinate A mixture of tert-butyl 4-bromo-6-methylpicolinate (2.37 g), copper(I) iodide (0.663 g), N,N'-dimethylethylenediamine (0.374 mL), potassium carbonate (2.4 g), (3S)-3-cyclopropyl-2-oxopyrrolidine-3-carbonitrile (1.7 g) and DME (15 mL) was stirred under microwave irradiation at 130° C. for 1 hr. The above-mentioned reaction was performed 3 more times, and four reaction mixtures were combined. The insoluble material was filtered off, the filtrate was diluted with ethyl acetate and saturated aqueous sodium hydrogen carbonate solution, and the aqueous layer was extracted with ethyl acetate. The organic layer was washed with saturated aqueous sodium hydrogen carbonate solution and saturated brine, and dried over anhydrous sodium sulfate. The solvent was evaporated under reduced pressure. The residue was purified by silica gel column chromatography (ethyl acetate/hexane), and the obtained solid was washed with ethyl acetate/hexane to give the title compound (9.69 g).

MS: [M+H]$^+$ 342.1.

D) 4-((3S)-3-cyano-3-cyclopropyl-2-oxopyrrolidin-1-yl)-6-methylpyridine-2-carboxylic acid A mixture of tert-butyl 4-((3S)-3-cyano-3-cyclopropyl-2-oxopyrrolidin-1-yl)-6-methylpicolinate (9.69 g) and TFA (30 mL) was stirred at room temperature for 3 hr. The solvent was evaporated under reduced pressure. To the residue were added ethyl acetate (20 mL) and 4N hydrogen chloride/ethyl acetate solution (20 mL) at room temperature.

The precipitate was collected by filtration, washed with ethyl acetate, and dried under reduced pressure to give the title compound (8.22 g).

MS: [M+H]+ 286.1.

E) 4-((3S)-3-cyano-3-cyclopropyl-2-oxopyrrolidin-1-yl)-N-(3-fluoro-5-(l-methyl-1H-pyrazol-4-yl)benzyl)-6-methylpyridine-2-carboxamide A mixture of TEA (11.24 mL), 1.7 M T3P/ethyl acetate solution (28.5 mL), 4-((3S)-3-cyano-3-cyclopropyl-2-oxopyrrolidin-1-yl)-6-methylpyridine-2-carboxylic acid (4.6 g), (3-fluoro-5-(l-methyl-1H-pyrazol-4-yl)phenyl)methanamine hydrochloride (4.29 g) and DMF (225 mL) was stirred at 50° C. for 2 hr. The reaction mixture was diluted with ethyl acetate and saturated aqueous ammonium chloride solution, and the aqueous layer was extracted with ethyl acetate. The organic layer was washed with saturated brine, dried over anhydrous magnesium sulfate and the solvent was evaporated under reduced pressure. The residue was purified by silica gel column chromatography (NH, ethyl acetate/hexane) to give a crude product (6.17 g). The obtained crude product (6.17 g) was recrystallized from IPE/ethyl acetate (1/1, 40 mL) and washed with IPE/ethyl acetate (5/1) to give the title compound (4.85 g).

$^1$H NMR (300 MHz, DMSO-d$_6$) δ 0.48-0.72 (4H, m), 1.47-1.56 (1H, m), 2.34-2.47 (1H, m), 2.58 (3H, s), 2.61-2.73 (1H, m), 3.85 (3H, s), 3.96-4.09 (2H, m), 4.51 (2H, d, J=6.3 Hz), 6.93 (1H, d, J=9.6 Hz), 7.27-7.39 (2H, m), 7.72 (1H, d, J=2.0 Hz), 7.87 (1H, d, J=0.8 Hz), 8.17 (1H, s), 8.24 (1H, d, J=1.9 Hz), 9.26 (1H, t, J=6.4 Hz).

Example 168

4-((3S)-3-cyano-3-cyclopropyl-2-oxopyrrolidin-1-yl)-N-(3-(1-cyclopropyl-1H-pyrazol-4-yl)-5-fluorobenzyl)-6-methylpyridine-2-carboxamide A) 3-(l-cyclopropyl-1H-pyrazol-4-yl)-5-fluorobenzonitrile A mixture of 3-bromo-5-fluorobenzonitrile (618 mg), 1-cyclopropyl-4-(4,4,5,5-tetramethyl-1,3,2-dioxaborolan-2-yl)-1H-pyrazole (1.0 g), PdCl$_2$(dppf) (113 mg), 2 M aqueous potassium carbonate solution (3.86 mL) and DME (10 mL) was stirred under a nitrogen atmosphere at 80° C. for 2 hr. To the reaction mixture was added water at room temperature, and the aqueous layer was extracted with ethyl acetate. The organic layer was washed with saturated brine and dried over anhydrous sodium sulfate. The solvent was evaporated under reduced pressure. The residue was purified by silica gel column chromatography (NH, ethyl acetate/hexane) to give the title compound (686 mg).

MS: [M+H]+ 228.0.

B) 1-(3-(1-cyclopropyl-1H-pyrazol-4-yl)-5-fluorophenyl)methanamine hydrochloride To a mixture of 3-(1-cyclopropyl-1H-pyrazol-4-yl)-5-fluorobenzonitrile (685.5 mg) and THF (12 mL) was added LAH (229 mg) at 0° C. The reaction mixture was stirred under a nitrogen atmosphere at the same temperature for 20 min. To the reaction mixture was further added LAH (229 mg) at 0° C., and the mixture was stirred under a nitrogen atmosphere at the same temperature for 10 min. To the reaction mixture were added water and 4N aqueous sodium hydroxide solution at room temperature, and the mixture was stirred at the same temperature for 30 min. The insoluble material was filtered off, and the filtrate was concentrated under reduced pressure. To the residue were added ethyl acetate (10 mL) and 4N hydrogen chloride/ethyl acetate solution (10 mL), and the precipitate was collected by filtration and washed with ethyl acetate to give the title compound (894 mg).

MS: [M+H]+ 232.1.

C) 4-((3S)-3-cyano-3-cyclopropyl-2-oxopyrrolidin-1-yl)-N-(3-(1-cyclopropyl-1H-pyrazol-4-yl)-5-fluorobenzyl)-6-methylpyridine-2-carboxamide A mixture of 4-((3S)-3-cyano-3-cyclopropyl-2-oxopyrrolidin-1-yl)-6-methylpyridine-2-carboxylic acid (65 mg), (3-(1-cyclopropyl-1H-pyrazol-4-yl)-5-fluorophenyl)methanamine hydrochloride (67.1 mg), 1.6 M T3P/DMF solution (0.427 mL), DIEA (0.199 mL) and DMF (2.0 mL) was stirred at 700° C. for 2 hr. To the reaction mixture were added ethyl acetate and water at room temperature, and the aqueous layer was extracted with ethyl acetate. The organic layer was washed with saturated brine and dried over anhydrous sodium sulfate. The solvent was evaporated under reduced pressure. The residue was purified by silica gel column chromatography (ethyl acetate/hexane, and then methanol/ethyl acetate) to give the title compound (64.2 mg).

$^1$H NMR (300 MHz, DMSO-d$_6$) δ 0.44-0.74 (4H, m), 0.93-1.02 (2H, m), 1.03-1.10 (2H, m), 1.22-1.28 (1H, m), 1.46-1.57 (1H, m), 2.35-2.44 (1H, m), 2.58 (3H, s), 2.63-2.75 (1H, m), 3.97-4.06 (2H, m), 4.51 (2H, d, J=6.1 Hz), 6.88-6.96 (1H, m), 7.28-7.35 (1H, m), 7.40 (1H, s), 7.72 (1H, d, J=2.1 Hz), 7.87 (1H, d, J=0.8 Hz), 8.23 (1H, d, J=1.8 Hz), 8.28 (1H, s), 9.24 (1H, t, J=6.8 Hz).

Example 237

6-((3S)-3-cyano-3-cyclopropyl-2-oxopyrrolidin-1-yl)-N-(3-fluoro-5-(1-methyl-1H-pyrazol-4-yl)benzyl)-2-methylpyrimidine-4-carboxamide A) 6-chloro-N-(3-fluoro-5-(1-methyl-1H-pyrazol-4-yl)benzyl)-2-methylpyrimidine-4-carboxamide A mixture of 6-hydroxy-2-methylpyrimidine-4-carboxylic acid (500 mg) and phosphorus oxychloride (5 mL) was heated under reflux under a nitrogen atmosphere for 2 hr. The solvent was evaporated under reduced pressure. To the residue was added THF (3 mL). The reaction mixture was added dropwise to a mixture of 1-(3-fluoro-5-(1-methyl-1H-pyrazol-4-yl)phenyl)methanamine (732 mg), TEA (646 mg) and dichloromethane (8 mL) at 0° C. over 10 min, and the reaction mixture was stirred at the same temperature for 2 hr. The reaction mixture was diluted with water, and the aqueous layer was extracted with dichloromethane. The organic layer was washed with saturated brine and dried over anhydrous sodium sulfate. The solvent was evaporated under reduced pressure. The residue was purified by silica gel column chromatography (ethyl acetate/petroleum ether) to give the title compound (198 mg).

MS: [M+H]+ 360.1.

B) 6-((3S)-3-cyano-3-cyclopropyl-2-oxopyrrolidin-1-yl)-N-(3-fluoro-5-(1-methyl-1H-pyrazol-4-yl)benzyl)-2-methylpyrimidine-4-carboxamide A mixture of potassium carbonate (61.5 mg), Xantphos (7.72 mg), 6-chloro-N-(3-fluoro-5-(1-methyl-1H-pyrazol-4-yl)benzyl)-2-methylpyrimidine-4-carboxamide (80 mg), (3S)-3-cyclopropyl-2-oxopyrrolidine-3-carbonitrile (50.1 mg), $Pd_2(dba)_3$ (4.1 mg) and DME (4 mL) was stirred under a nitrogen atmosphere at 85° C. overnight. The reaction mixture was diluted with ethyl acetate and saturated aqueous sodium hydrogen carbonate solution, and the aqueous layer was extracted with ethyl acetate. The organic layer was dried over anhydrous magnesium sulfate, and the solvent was evaporated under reduced pressure. The residue was purified by silica gel column chromatography (NH, ethyl acetate/hexane) to give the title compound (11.60 mg).

$^1$H NMR (300 MHz, DMSO-$d_6$) δ 0.52-0.71 (4H, m), 1.50-1.58 (1H, m), 2.33-2.44 (1H, m), 2.63-2.73 (4H, m), 3.85 (3H, s), 3.93-4.27 (2H, m), 4.51 (2H, d, J=6.61 Hz) 6.93 (1H, d, J=5.69 Hz), 7.30 (1H, d, J=9.91 Hz), 7.37 (1H, s), 7.88 (1H, d, J=0.85 Hz), 8.17 (1H, s), 8.63 (1H, s), 9.46 (1H, t, J=6.29 Hz).

Example 238

4-((3S)-3-cyano-3-cyclopropyl-2-oxopyrrolidin-1-yl)-N-(3-fluoro-5-(1-methyl-1H-pyrazol-4-yl)benzyl)-6-methylpyrimidine-2-carboxamide

A) ethyl 2-((3-methylisoxazol-5-yl)amino)-2-oxoacetate

To a mixture of 3-methyl-1,2-oxazol-5-amine (15.83 g) and pyridine (100 mL) was gradually added ethyl 2-chloro-2-oxoacetate (23.13 g) at room temperature. The reaction mixture was stirred at the same temperature for 1 hr 30 min. The reaction mixture was diluted with ethyl acetate and water, and the aqueous layer was extracted with ethyl acetate. The organic layer was washed with 1N hydrochloric acid and dried over anhydrous sodium sulfate. The solvent was evaporated under reduced pressure. The precipitate was collected by filtration and washed with ethyl acetate/hexane to give the title compound (30.7 g).

MS: [M+H]$^+$ 199.1.

B) ethyl 4-hydroxy-6-methylpyrimidine-2-carboxylate

A mixture of ethyl 2-((3-methylisoxazol-5-yl)amino)-2-oxoacetate (1.0 g), 10% palladium carbon (0.1 g) and ethanol (30 mL) was stirred under normal pressure and a hydrogen atmosphere at room temperature for 5 hr. Hydrogen was removed, and the reaction mixture was heated under reflux overnight. After completion of the reaction, the catalyst was filtered off, and the filtrate was concentrated under reduced pressure. The residue was purified by silica gel column chromatography (ethyl acetate/petroleum ether) to give the title compound (0.6 g).

MS: [M+H]$^+$ 183.2.

C) N-(3-fluoro-5-(1-methyl-1H-pyrazol-4-yl)benzyl)-4-hydroxy-6-methylpyrimidine-2-carboxamide To a mixture of ethyl 4-hydroxy-6-methylpyrimidine-2-carboxylate (1.5 g), 1-(3-fluoro-5-(1-methyl-1H-pyrazol-4-yl)phenyl)methanamine (1.7 g) and toluene (20 mL) was gradually added dropwise 1M trimethylaluminum/toluene solution (16.4 mL) under a nitrogen atmosphere at room temperature. The reaction mixture was stirred under a nitrogen atmosphere at the same temperature overnight. To the reaction mixture was added methanol at room temperature, insoluble material was filtered off, and the filtrate was concentrated under reduced pressure. The residue was purified by silica gel column chromatography (methanol/dichloromethane) to give the title compound (1.4 g).

MS: [M+H]$^+$ 342.2.

D) 4-chloro-N-(3-fluoro-5-(1-methyl-1H-pyrazol-4-yl)benzyl)-6-methylpyrimidine-2-carboxamide A mixture of N-(3-fluoro-5-(1-methyl-1H-pyrazol-4-yl)benzyl)-4-hydroxy-6-methylpyrimidine-2-carboxamide (1.0 g) and phosphorus oxychloride (10 mL) was stirred at 70° C. for 12 hr. The solvent was evaporated under reduced pressure. To the residue was added water at 0° C., and saturated aqueous sodium hydrogen carbonate solution was added to adjust pH to 8. The aqueous layer was extracted with ethyl acetate, the organic layer was dried over anhydrous sodium sulfate, and the solvent was evaporated under reduced pressure. The residue was purified by silica gel column chromatography (ethyl acetate/petroleum ether) to give the title compound (496.6 mg).

MS: [M+H]$^+$ 360.1.

E) 4-((3S)-3-cyano-3-cyclopropyl-2-oxopyrrolidin-1-yl)-N-(3-fluoro-5-(1-methyl-1H-pyrazol-4-yl)benzyl)-6-methylpyrimidine-2-carboxamide A mixture of potassium carbonate (77 mg), Xantphos (9.65 mg), 4-chloro-N-(3-fluoro-5-(1-methyl-1H-pyrazol-4-yl)benzyl)-6-methylpyrimidine-2-carboxamide (100 mg), (3S)-3-cyclopropyl-2-oxopyrrolidine-3-carbonitrile (62.6 mg), $Pd_2(dba)_3$ (5.1 mg) and DME (4 mL) was stirred under a nitrogen atmosphere at 850° C. overnight. The solvent was evaporated under reduced pressure, and the residue was purified by silica gel column chromatography (NH, ethyl acetate/hexane) to give the title compound (47.6 mg).

$^1$H NMR (300 MHz, DMSO-$d_6$) δ 0.42-0.73 (4H, m), 1.54 (1H, tt, J=8.11, 5.11 Hz), 2.30-2.45 (1H, m), 2.58 (3H, s), 2.62-2.75 (1H, m), 3.86 (3H, s), 3.99-4.14 (1H, m), 4.23-4.32 (1H, m), 4.51 (2H, d, J=6.23 Hz), 6.94 (1H, d, J=9.26 Hz), 7.28-7.40 (2H, m), 7.88 (1H, d, J=0.76 Hz), 8.17 (1H, s), 8.22 (1H, s), 9.37 (1H, t, J=6.37 Hz).

According to the methods shown in the above-mentioned Examples or a method analogous thereto, the compounds of Examples 1, 3-22, 24-31, 35-62, 64-85, 87-152, 154-158, 160-167, 169-236, 239, 240 in the following Tables were produced. Example compounds are shown in the following Tables. In the Tables, MS shows measured values.

TABLE 1

| Ex. No. | IUPAC name | structural formula | salt | MS |
|---|---|---|---|---|
| 1 | N-(2-chlorobenzyl)-8-cyclopentyl-7H-purine-6-carboxamide | | | 356.1 |
| 2 | 8-cyclopentyl-N-(3-fluoro-5-(1-methyl-1H-pyrazol-4-yl)benzyl)-7H-purine-6-carboxamide | | | 420.1 |
| 3 | 8-cyclopentyl-N-(3-fluoro-5-(1-methyl-1H-pyrazol-4-yl)benzyl)-7-methyl-7H-purine-6-carboxamide | | | 434.1 |
| 4 | 8-cyclopentyl-N-(3-fluoro-5-(1-methyl-6-oxo-1,6-dihydropyridin-3-yl)benzyl)-7-methyl-7H-purine-6-carboxamide | | | 461.2 |

TABLE 1-continued

| Ex. No. | IUPAC name | structural formula | salt | MS |
|---|---|---|---|---|
| 5 | 8-cyclopentyl-N-(2,3-difluoro-5-(1-methyl-1H-pyrazol-4-yl)benzyl)-7-methyl-7H-purine-6-carboxamide | | | 452.2 |
| 6 | 8-cyclopentyl-N-(3-fluoro-2-methoxy-5-(1-methyl-1H-pyrazol-4-yl)benzyl)-7-methyl-7H-purine-6-carboxamide | | | 464.3 |
| 7 | 8-cyclopentyl-N-(3-fluoro-5-(1-methyl-1H-1,2,3-triazol-4-yl)benzyl)-7-methyl-7H-purine-6-carboxamide | | | 435.1 |
| 8 | 8-cyclopentyl-N-(3-fluoro-5-(1-methyl-6-oxo-1,6-dihydropyridin-3-yl)benzyl)-7H-purine-6-carboxamide | | | 447.1 |

TABLE 1-continued

| Ex. No. | IUPAC name | structural formula | salt | MS |
|---|---|---|---|---|
| 9 | 8-cyclopentyl-N-(3-fluoro-5-(1-methyl-1H-1,2,3-triazol-4-yl)benzyl)-7H-purine-6-carboxamide | | | 421.2 |
| 10 | 8-cyclopentyl-N-((2-methyl-2H-indazol-4-yl)methyl)-7H-purine-6-carboxamide | | | 376.1 |
| 11 | 8-cyclopentyl-N-(3-fluoro-5-(1-isopropyl-1H-pyrazol-4-yl)benzyl)-7H-purine-6-carboxamide | | | 446.1 |
| 12 | 2-chloro-8-cyclopentyl-N-(3-fluoro-5-(1-methyl-1H-pyrazol-4-yl)benzyl)-7H-purine-6-carboxamide | | | 454.2 |

TABLE 1-continued

| Ex. No. | IUPAC name | structural formula | salt | MS |
|---|---|---|---|---|
| 13 | 8-cyclopentyl-N-(3-fluoro-5-(1-methyl-1H-pyrazol-4-yl)benzyl)-2-methyl-7H-purine-6-carboxamide | | | 434.1 |
| 14 | 8-cyclopentyl-N-(3-(1-cyclopropyl-1H-pyrazol-4-yl)-5-fluorobenzyl)-7H-purine-6-carboxamide | | | 446.2 |
| 15 | 2-chloro-N-(3-fluoro-5-(1-methyl-1H-pyrazol-4-yl)benzyl)-8-(tetrahydrofuran-2-yl)-7H-purine-6-carboxamide | | | 456.1 |
| 16 | N-(3-cyano-5-(1-methyl-1H-pyrazol-4-yl)benzyl)-8-cyclopentyl-7H-purine-6-carboxamide | | | 427.2 |

TABLE 1-continued

| Ex. No. | IUPAC name | structural formula | salt | MS |
|---|---|---|---|---|
| 17 | 8-cyclopentyl-N-(imidazo[1,2-a]pyridin-5-ylmethyl)-7H-purine-6-carboxamide | | | 362.2 |
| 18 | 8-cyclopentyl-N-(3-fluoro-5-(1-methyl-1H-pyrazol-4-yl)benzyl)-2-methoxy-7H-purine-6-carboxamide | | | 450.2 |
| 19 | 2-cyano-8-cyclopentyl-N-(3-fluoro-5-(1-methyl-1H-pyrazol-4-yl)benzyl)-7H-purine-6-carboxamide | | | 445.2 |
| 20 | N-(3-cyano-5-(1-methyl-1H-pyrazol-4-yl)benzyl)-8-cyclopentyl-7-methyl-7H-purine-6-carboxamide | | | 441.2 |

TABLE 1-continued

| Ex. No. | IUPAC name | structural formula | salt | MS |
|---|---|---|---|---|
| 21 | 8-cyclopentyl-7-methyl-N-((1-methyl-1H-indazol-7-yl)methyl)-7H-purine-6-carboxamide | | | 390.2 |
| 22 | N-(3-fluoro-5-(1-methyl-1H-pyrazol-4-yl)benzyl)-8-(tetrahydrofuran-2-yl)-7H-purine-6-carboxamide | | | 422.2 |
| 23 | N-(3-cyano-5-(1-methyl-1H-pyrazol-4-yl)benzyl)-7-methyl-8-(tetrahydrofuran-2-yl)-7H-purine-6-carboxamide | | | 443.3 |
| 24 | N-(3-fluoro-5-(1-methyl-1H-pyrazol-4-yl)benzyl)-8-(tetrahydrofuran-3-yl)-7H-purine-6-carboxamide | | | 422.2 |

TABLE 1-continued

| Ex. No. | IUPAC name | structural formula | salt | MS |
|---|---|---|---|---|
| 25 | N-(3-fluoro-5-(1-methyl-1H-pyrazol-4-yl)benzyl)-7-methyl-8-(tetrahydrofuran-2-yl)-7H-purine-6-carboxamide | 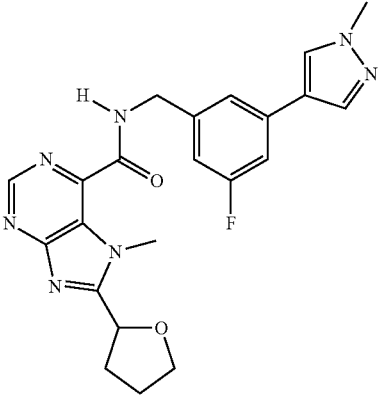 [SMILES: Cn1cc(-c2cc(F)cc(CNC(=O)c3ncnc4nc(C5CCCO5)n(C)c34)c2)cn1] | | 436.2 |
| 26 | N-(3-fluoro-5-(1-methyl-1H-pyrazol-4-yl)benzyl)-7-methyl-8-(tetrahydrofuran-3-yl)-7H-purine-6-carboxamide | 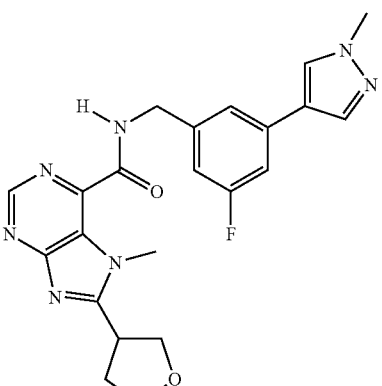 | | 436.2 |
| 27 | 8-(1-fluorocyclopentyl)-N-(3-fluoro-5-(1-methyl-1H-pyrazol-4-yl)benzyl)-7H-purine-6-carboxamide | 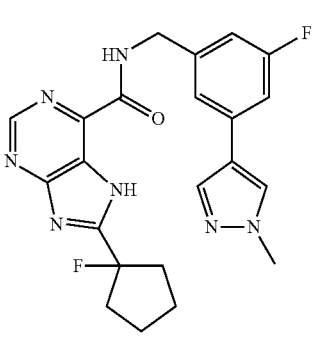 [SMILES: Cn1cc(-c2cc(F)cc(CNC(=O)c3ncnc4nc(C5(F)CCCC5)[nH]c34)c2)cn1] | | 438.2 |
| 28 | 8-(1,1-dioxidotetrahydro-thiophen-3-yl)-N-(3-fluoro-5-(1-methyl-1H-pyrazol-4-yl)benzyl)-7H-purine-6-carboxamide | 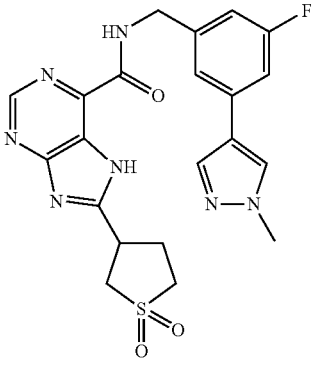 [SMILES: Cn1cc(-c2cc(F)cc(CNC(=O)c3ncnc4nc(C5CCS(=O)(=O)C5)[nH]c34)c2)cn1] | | 470.2 |

TABLE 1-continued

| Ex. No. | IUPAC name | structural formula | salt | MS |
|---|---|---|---|---|
| 29 | N-(3-fluoro-5-(1-methyl-1H-pyrazol-4-yl)benzyl)-8-(3-hydroxycyclopentyl)-7H-purine-6-carboxamide | | | 436.2 |
| 30 | 8-cyclopentyl-N-(3-fluoro-5-(1-(1-hydroxy-2-methylpropan-2-yl)-1H-pyrazol-4-yl)benzyl)-7-methyl-7H-purine-6-carboxamide | | | 492.4 |
| 31 | N-(3-fluoro-5-(1-methyl-1H-pyrazol-4-yl)benzyl)-8-(tetrahydro-2H-pyran-2-yl)-7H-purine-6-carboxamide | | | 436.2 |
| 32 | 8-(1,4-dioxan-2-yl)-N-(3-fluoro-5-(1-methyl-1H-pyrazol-4-yl)benzyl)-7H-purine-6-carboxamide | | | 438.2 |

TABLE 1-continued

| Ex. No. | IUPAC name | salt | MS |
|---|---|---|---|
| 33 | 8-(1,4-dioxan-2-yl)-N-(3-fluoro-5-(1-methyl-1H-pyrazol-4-yl)benzyl)-7H-purine-6-carboxamide (tR1) | | 438.2 |
| 34 | 8-(1,4-dioxan-2-yl)-N-(3-fluoro-5-(1-methyl-1H-pyrazol-4-yl)benzyl)-7H-purine-6-carboxamide (tR2) | | 438.2 |
| 35 | 8-cyclopentyl-N-(3-(4H-1,2,4-triazol-4-yl)benzyl)-7H-purine-6-carboxamide | | 387.2 |
| 36 | 8-cyclopentyl-N-(3-(1H-1,2,4-triazol-1-yl)benzyl)-7H-purine-6-carboxamide | | 389.3 |

TABLE 1-continued

| Ex. No. | IUPAC name | structural formula | salt | MS |
|---|---|---|---|---|
| 37 | 8-cyclopentyl-N-(3-(1H-imidazol-1-yl)benzyl)-7H-purine-6-carboxamide | | | 388.2 |
| 38 | 8-cyclopentyl-2-ethynyl-N-(3-fluoro-5-(1-methyl-1H-pyrazol-4-yl)benzyl)-7H-purine-6-carboxamide | | | 444.3 |
| 39 | 8-cyclopentyl-N-(3-(1H-pyrazol-1-yl)benzyl)-7H-purine-6-carboxamide | | | 388.2 |
| 40 | 8-(3,3-difluorocyclopentyl)-N-(3-fluoro-5-(1-methyl-1H-pyrazol-4-yl)benzyl)-7H-purine-6-carboxamide | | | 456.2 |

TABLE 1-continued

| Ex. No. | IUPAC name | structural formula | salt | MS |
|---|---|---|---|---|
| 41 | N-(3-fluoro-5-(1-methyl-6-oxo-1,6-dihydropyridin-3-yl)benzyl)-7-methyl-8-(tetrahydrofuran-3-yl)-7H-purine-6-carboxamide | | | 463.2 |
| 42 | 2-amino-8-cyclopentyl-N-(3-fluoro-5-(1-methyl-1H-pyrazol-4-yl)benzyl)-7H-purine-6-carboxamide | | | 435.2 |
| 43 | 8-cyclopentyl-N-(3-fluoro-5-(1-methyl-1H-pyrazol-4-yl)benzyl)-2-(methylamino)-7H-purine-6-carboxamide | | | 449.2 |
| 44 | 8-cyclopentyl-N-(3-(1H-1,2,3-triazol-1-yl)benzyl)-7H-purine-6-carboxamide | | | 389.2 |

TABLE 1-continued

| Ex. No. | IUPAC name | structural formula | salt | MS |
|---|---|---|---|---|
| 45 | 8-(1-cyclopropylethyl)-N-(3-fluoro-5-(1-methyl-1H-pyrazol-4-yl)benzyl)-7H-purine-6-carboxamide | | | 420.2 |
| 46 | N-(3-(1-tert-butyl-1H-pyrazol-4-yl)-5-fluorobenzyl)-8-cyclopentyl-7-methyl-7H-purine-6-carboxamide | | | 476.4 |
| 47 | 8-(bicyclo[1.1.1]pent-1-yl)-N-(3-fluoro-5-(1-methyl-1H-pyrazol-4-yl)benzyl)-7H-purine-6-carboxamide | | | 418.2 |
| 48 | 8-cyclopentyl-N-(3-fluoro-5-(1-(1-hydroxy-2-methylpropan-2-yl)-1H-pyrazol-4-yl)benzyl)-7H-purine-6-carboxamide | | | 478.3 |

TABLE 1-continued

| Ex. No. | IUPAC name | structural formula | salt | MS |
|---|---|---|---|---|
| 49 | N-(3-cyano-5-(1-cyclopropyl-1H-pyrazol-4-yl)benzyl)-8-cyclopentyl-7-methyl-7H-purine-6-carboxamide | 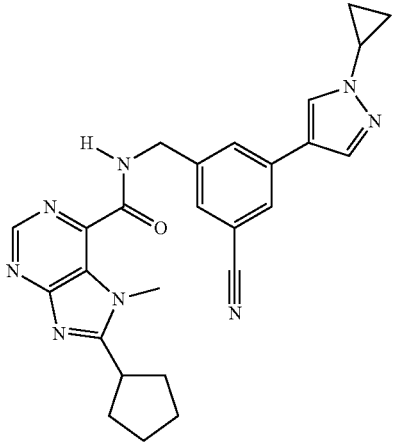 [SMILES: Cn1c(C2CCCC2)nc2ncnc(C(=O)NCc3cc(C#N)cc(-c4cnn(C5CC5)c4)c3)c21] | | 467.2 |
| 50 | N-(3-fluoro-5-(1-methyl-1H-pyrazol-4-yl)benzyl)-8-(tetrahydrothiophen-3-yl)-7H-purine-6-carboxamide | 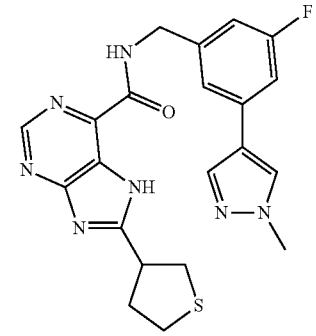 [SMILES: Cn1cc(-c2cc(F)cc(CNC(=O)c3ncnc4nc(C5CCSC5)[nH]c34)c2)cn1] | | 438.2 |
| 51 | 8-cyclopentyl-N-(3-(3,4-dimethyl-1H-pyrazol-1-yl)-5-fluorobenzyl)-7H-purine-6-carboxamide | 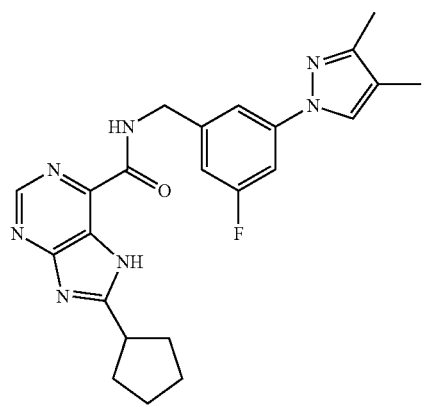 [SMILES: Cc1cn(-c2cc(F)cc(CNC(=O)c3ncnc4nc(C5CCCC5)[nH]c34)c2)nc1C] | | 434.2 |
| 52 | 8-cyclopentyl-7-methyl-N-((4-(1-methyl-1H-pyrazol-4-yl)pyridin-2-yl)methyl)-7H-purine-6-carboxamide | 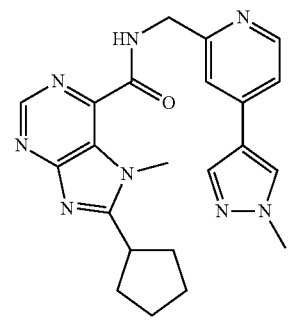 [SMILES: Cn1cc(-c2ccnc(CNC(=O)c3ncnc4nc(C5CCCC5)n(C)c34)c2)cn1] | | 417.2 |

TABLE 1-continued

| Ex. No. | IUPAC name | structural formula | salt | MS |
|---|---|---|---|---|
| 53 | 8-cyclopentyl-7-methyl-N-((6-(1-methyl-1H-pyrazol-4-yl)pyridin-2-yl)methyl)-7H-purine-6-carboxamide | | | 417.2 |
| 54 | 8-cyclopentyl-7-methyl-N-((5-(1-methyl-1H-pyrazol-4-yl)pyridin-3-yl)methyl)-7H-purine-6-carboxamide | | | 417.2 |
| 55 | 8-cyclopentyl-7-methyl-N-((2-(1-methyl-1H-pyrazol-4-yl)pyridin-4-yl)methyl)-7H-purine-6-carboxamide | | | 417.2 |
| 56 | 8-cyclopentyl-N-(3-(3,4-dimethyl-1H-pyrazol-1-yl)-5-fluorobenzyl)-7-methyl-7H-purine-6-carboxamide | | | 448.2 |

TABLE 1-continued

| Ex. No. | IUPAC name | structural formula | salt | MS |
|---|---|---|---|---|
| 57 | 8-cyclopentyl-N-(3-(2H-1,2,3-triazol-2-yl)benzyl)-7H-purine-6-carboxamide | | | 389.3 |
| 58 | 8-cyclobutyl-N-(3-fluoro-5-(1-methyl-1H-pyrazol-4-yl)benzyl)-7H-purine-6-carboxamide | | | 406.2 |
| 59 | 8-(dicyclopropyl-methyl)-N-(3-fluoro-5-(1-methyl-1H-pyrazol-4-yl)benzyl)-7H-purine-6-carboxamide | | | 446.2 |
| 60 | N-(3-(3-cyano-1-methyl-1H-pyrazol-4-yl)-5-fluorobenzyl)-8-cyclopentyl-7-methyl-7H-purine-6-carboxamide | | | 459.3 |

TABLE 1-continued

| Ex. No. | IUPAC name | structural formula | salt | MS |
|---|---|---|---|---|
| 61 | 8-cyclopentyl-N-(pyrazolo[1,5-a]pyridin-7-yl methyl)-7H-purine-6-carboxamide | | | 362.2 |
| 62 | 8-cyclopentyl-N-(3-(2-cyclopropyl-2H-1,2,3-triazol-4-yl)-5-fluorobenzyl)-7H-purine-6-carboxamide | | | 445.2 |
| 63 | N-(3-fluoro-5-(1-methyl-1H-pyrazol-4-yl)benzyl)-7-methyl-8-(tetrahydro-2H-pyran-2-yl)-7H-purine-6-carboxamide | | | 450.2 |
| 64 | N-(3-fluoro-5-(1-methyl-6-oxo-1,6-dihydropyridin-3-yl)benzyl)-7-methyl-8-(tetrahydro-2H-pyran-2-yl)-7H-purine-6-carboxamide | | | 477.2 |

TABLE 1-continued

| Ex. No. | IUPAC name | structural formula | salt | MS |
|---|---|---|---|---|
| 65 | 8-cyclopentyl-N-(3-fluoro-5-(1-methyl-3-(trifluoromethyl)-1H-pyrazol-4-yl)benzyl)-7-methyl-7H-purine-6-carboxamide | | | 502.2 |
| 66 | 8-cyclopropyl-N-(3-fluoro-5-(1-methyl-1H-pyrazol-4-yl)benzyl)-7H-purine-6-carboxamide | | | 392.2 |
| 67 | N-(3-(1-(difluoromethyl)-1H-pyrazol-4-yl)-5-fluorobenzyl)-7-methyl-8-(tetrahydro-2H-pyran-2-yl)-7H-purine-6-carboxamide | | | 486.2 |

TABLE 1-continued

| Ex. No. | IUPAC name | structural formula | salt | MS |
|---|---|---|---|---|
| 68 | N-(3-(1-(difluoromethyl)-1H-pyrazol-4-yl)-5-fluorobenzyl)-8-(1,4-dioxan-2-yl)-7-methyl-7H-purine-6-carboxamide | | | 488.2 |
| 69 | 8-cyclopentyl-N-((1-methyl-1H-benzimidazol-7-yl)methyl)-7H-purine-6-carboxamide | | | 376.1 |
| 70 | 8-cyclopentyl-N-(3-(1-(2,2-difluoroethyl)-1H-1,2,3-triazol-4-yl)-5-fluorobenzyl)-7H-purine-6-carboxamide | | | 471.0 |

TABLE 1-continued

| Ex. No. | IUPAC name | structural formula | salt | MS |
|---|---|---|---|---|
| 71 | 8-cyclopentyl-N-(3-fluoro-5-(2-methyl-2H-1,2,3-triazol-4-yl)benzyl)-7H-purine-6-carboxamide | | | 421.1 |
| 72 | 8-cyclopentyl-N-(3-(2-(2,2-difluoroethyl)-2H-1,2,3-triazol-4-yl)-5-fluorobenzyl)-7H-purine-6-carboxamide | | | 471.2 |
| 73 | 8-cyclopentyl-N-(3-fluoro-5-(1-methyl-1H-1,2,4-triazol-3-yl)benzyl)-7H-purine-6-carboxamide | | | 421.2 |

TABLE 1-continued

| Ex. No. | IUPAC name | salt | MS |
|---|---|---|---|
| 74 | 8-cyclopentyl-N-(3-(1-ethyl-1H-1,2,3-triazol-4-yl)-5-fluorobenzyl)-7H-purine-6-carboxamide | | 435.2 |
| 75 | 8-cyclopentyl-N-((2-methyl-2H-indazol-7-yl)methyl)-7H-purine-6-carboxamide | | 376.2 |
| 76 | 8-cyclopentyl-N-(imidazo[1,2-a]pyridin-8-ylmethyl)-7H-purine-6-carboxamide | | 362.2 |
| 77 | 8-cyclopentyl-N-((1-methyl-1H-benzimidazol-4-yl)methyl)-7H-purine-6-carboxamide | | 376.2 |

TABLE 1-continued

| Ex. No. | IUPAC name | salt | MS |
|---|---|---|---|
| 78 | 8-(1,4-dioxan-2-yl)-N-(3-fluoro-5-(1-(2,2,2-trifluoroethyl)-1H-pyrazol-4-yl)benzyl)-7-methyl-7H-purine-6-carboxamide | | 520.2 |
| 79 | N-(3-fluoro-5-(1-methyl-1H-pyrazol-4-yl)benzyl)-8-(tetrahydro-2H-pyran-3-yl)-7H-purine-6-carboxamide | | 436.2 |
| 80 | N-(3-fluoro-5-(1-methyl-1H-pyrazol-4-yl)benzyl)-8-(tetrahydro-2H-pyran-4-yl)-7H-purine-6-carboxamide | | 436.2 |
| 81 | N-(2-chlorobenzyl)-2-cyclopentyl-3H-imidazo[4,5-c]pyridine-4-carboxamide | | 355.1 |

TABLE 1-continued
| Ex. No. | IUPAC name | structural formula | salt | MS |
|---|---|---|---|---|
| 82 | N-(3-bromobenzyl)-2-cyclopentyl-3H-imidazo[4,5-c]pyridine-4-carboxamide | 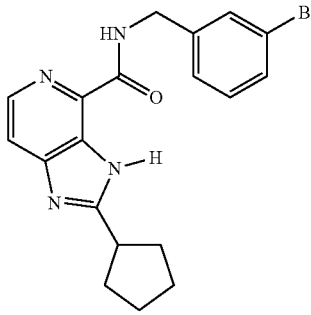 | | 399.0 |
| 83 | N-(biphenyl-3-ylmethyl)-2-cyclopentyl-3H-imidazo[4,5-c]pyridine-4-carboxamide | 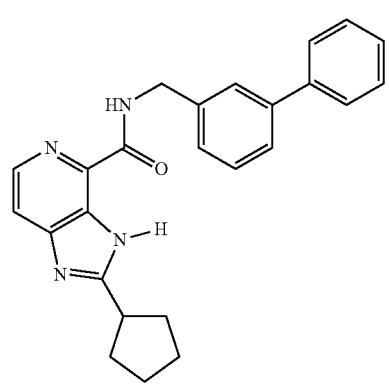 [SMILES: O=C(NCc1cccc(-c2ccccc2)c1)c1nccc2nc(C3CCCC3)[nH]c12] | | 397.2 |
| 84 | 2-cyclopentyl-N-(3-(1-methyl-1H-pyrazol-4-yl)benzyl)-3H-imidazo[4,5-c]pyridine-4-carboxamide | 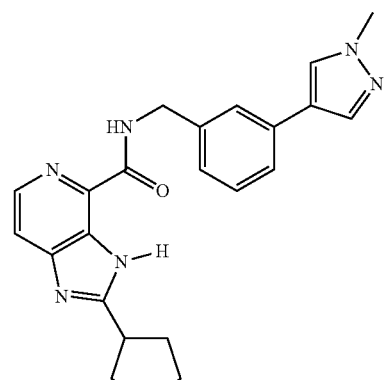 | | 401.2 |
| 85 | N-(2-chlorobenzyl)-2-cyclopentyl-3-methyl-3H-imidazo[4,5-c]pyridine-4-carboxamide | 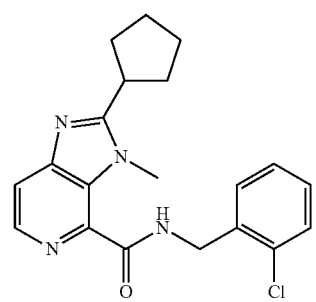 [SMILES: Cn1c(C2CCCC2)nc2ccnc(C(=O)NCc3ccccc3Cl)c21] | | 369.1 |

TABLE 1-continued

| Ex. No. | IUPAC name | structural formula | salt | MS |
|---|---|---|---|---|
| 86 | 2-cyclopentyl-N-(3-fluoro-5-(1-methyl-1H-pyrazol-4-yl)benzyl)-3H-imidazo[4,5-c]pyridine-4-carboxamide | | | 419.2 |
| 87 | N-(2-chlorobenzyl)-2-(1-methylcyclopentyl)-3H-imidazo[4,5-c]pyridine-4-carboxamide | | | 367.0 |
| 88 | 2-cyclopentyl-N-(3-fluoro-5-(1-methyl-1H-pyrazol-4-yl)benzyl)-3-methyl-3H-imidazo[4,5-c]pyridine-4-carboxamide | | | 433.2 |
| 89 | 2-cyclopentyl-N-(3-fluoro-5-(1-methyl-1H-1,2,3-triazol-4-yl)benzyl)-3H-imidazo[4,5-c]pyridine-4-carboxamide | | | 420.1 |

TABLE 1-continued

| Ex. No. | IUPAC name | structural formula | salt | MS |
|---|---|---|---|---|
| 90 | 2-cyclopentyl-N-(2,3-difluoro-5-(1-methyl-1H-pyrazol-4-yl)benzyl)-3H-imidazo[4,5-c]pyridine-4-carboxamide | | | 437.2 |
| 91 | 2-cyclopentyl-N-(3-fluoro-5-(1-methyl-1H-1,2,3-triazol-4-yl)benzyl)-3-methyl-3H-imidazo[4,5-c]pyridine-4-carboxamide | | | 434.1 |
| 92 | 2-cyclopentyl-N-(3-fluoro-5-(1-methyl-6-oxo-1,6-dihydropyridin-3-yl)benzyl)-3-methyl-3H-imidazo[4,5-c]pyridine-4-carboxamide | | | 460.3 |
| 93 | 2-cyclopentyl-N-((1-methyl-1H-indazol-4-yl)methyl)-3H-imidazo[4,5-c]pyridine-4-carboxamide | | | 375.2 |

TABLE 1-continued

| Ex. No. | IUPAC name | structural formula | salt | MS |
|---|---|---|---|---|
| 94 | 2-cyclopentyl-N-((2-methyl-2H-indazol-4-yl)methyl)-3H-imidazo[4,5-c]pyridine-4-carboxamide | | | 375.2 |
| 95 | 2-cyclopentyl-N-((1-methyl-1H-indazol-7-yl)methyl)-3H-imidazo[4,5-c]pyridine-4-carboxamide | | | 375.2 |
| 96 | 2-cyclopentyl-N-(3-fluoro-5-(2-methoxypyridin-4-yl)benzyl)-3-methyl-3H-imidazo[4,5-c]pyridine-4-carboxamide | | | 460.3 |
| 97 | 2-cyclopentyl-N-(3-fluoro-5-(2-oxo-1,2-dihydropyridin-4-yl)benzyl)-3-methyl-3H-imidazo[4,5-c]pyridine-4-carboxamide | | | 446.2 |

TABLE 1-continued

| Ex. No. | IUPAC name | structural formula | salt | MS |
|---|---|---|---|---|
| 98 | 2-cyclopentyl-N-(3-fluoro-5-(1-methyl-2-oxo-1,2-dihydropyridin-4-yl)benzyl)-3-methyl-3H-imidazo[4,5-c]pyridine-4-carboxamide | | | 460.3 |
| 99 | N-(3-fluoro-5-(1-methyl-1H-pyrazol-4-yl)benzyl)-2-isopropyl-3H-imidazo[4,5-c]pyridine-4-carboxamide | | | 393.2 |
| 100 | methyl 3-((((2-cyclopentyl-3H-imidazo[4,5-c]pyridin-4-yl)carbonyl)-amino)methyl)benzoate | | | 379.2 |
| 101 | 2-cyclopentyl-3-ethyl-N-(3-fluoro-5-(1-methyl-1H-pyrazol-4-yl)benzyl)-3H-imidazo[4,5-c]pyridine-4-carboxamide | | | 447.2 |

TABLE 1-continued

| Ex. No. | IUPAC name | structural formula | salt | MS |
|---|---|---|---|---|
| 102 | 3-(2-(benzyloxy)ethyl)-2-cyclopentyl-N-(3-fluoro-5-(1-methyl-1H-pyrazol-4-yl)benzyl)-3H-imidazo[4,5-c]pyridine-4-carboxamide | | | 553.3 |
| 103 | N-(3-fluoro-5-(1-methyl-1H-pyrazol-4-yl)benzyl)-2-(tetrahydrofuran-3-yl)-3H-imidazo[4,5-c]pyridine-4-carboxamide | | | 421.2 |
| 104 | 2-(cyclopentylmethyl)-N-(3-fluoro-5-(1-methyl-1H-pyrazol-4-yl)benzyl)-3H-imidazo[4,5-c]pyridine-4-carboxamide | | | 433.2 |

TABLE 1-continued

| Ex. No. | IUPAC name | structural formula | salt | MS |
|---|---|---|---|---|
| 105 | N-(3-cyano-5-(1-methyl-1H-pyrazol-4-yl)benzyl)-2-cyclopentyl-3H-imidazo[4,5-c]pyridine-4-carboxamide | | | 426.2 |
| 106 | 2-cyclopentyl-N-(3-((1-methyl-1H-pyrazol-4-yl)carbamoyl)benzyl)-3H-imidazo[4,5-c]pyridine-4-carboxamide | | | 442.2 |
| 107 | 3-((((2-cyclopentyl-3H-imidazo[4,5-c]pyridin-4-yl)carbonyl)amino)methyl)benzoic acid | | | 365.2 |

TABLE 1-continued

| Ex. No. | IUPAC name | structural formula | salt | MS |
|---|---|---|---|---|
| 108 | 2-cyclopentyl-3-cyclopropyl-N-(3-fluoro-5-(1-methyl-1H-pyrazol-4-yl)benzyl)-3H-imidazo[4,5-c]pyridine-4-carboxamide | | | 459.3 |
| 109 | 2-benzyl-N-(3-fluoro-5-(1-methyl-1H-pyrazol-4-yl)benzyl)-3H-imidazo[4,5-c]pyridine-4-carboxamide | | | 441.2 |
| 110 | 2-cyclopentyl-N-(3-fluoro-5-(3-(hydroxymethyl)-1-methyl-1H-pyrazol-4-yl)benzyl)-3H-imidazo[4,5-c]pyridine-4-carboxamide | | | 449.1 |

TABLE 1-continued

| Ex. No. | IUPAC name | structural formula | salt | MS |
|---|---|---|---|---|
| 111 | 2-cyclopentyl-N-(3-fluoro-5-(1-(1-hydroxy-2-methylpropan-2-yl)-1H-pyrazol-4-yl)benzyl)-3H-imidazo[4,5-c]pyridine-4-carboxamide | | | 477.2 |
| 112 | N-(3-cyano-5-(1-methyl-1H-pyrazol-4-yl)benzyl)-2-cyclopentyl-3-methyl-3H-imidazo[4,5-c]pyridine-4-carboxamide | | | 440.2 |
| 113 | 2-cyclopentyl-7-fluoro-N-(3-fluoro-5-(1-methyl-1H-pyrazol-4-yl)benzyl)-3-methyl-3H-imidazo[4,5-c]pyridine-4-carboxamide | | | 451.2 |

TABLE 1-continued

| Ex. No. | IUPAC name | structural formula | salt | MS |
|---|---|---|---|---|
| 114 | 2-cyclopentyl-3-(cyclopropylmethyl)-N-(3-fluoro-5-(1-methyl-1H-pyrazol-4-yl)benzyl)-3H-imidazo[4,5-c]pyridine-4-carboxamide | | | 473.3 |
| 115 | 2-cyclopentyl-N-(3-fluoro-5-(1-methyl-1H-pyrazol-4-yl)benzyl)-3-(2-hydroxyethyl)-3H-imidazo[4,5-c]pyridine-4-carboxamide | | | 463.2 |
| 116 | N-(3-cyano-2-fluoro-5-(1-methyl-1H-pyrazol-4-yl)benzyl)-2-cyclopentyl-3-methyl-3H-imidazo[4,5-c]pyridine-4-carboxamide | | | 458.2 |

TABLE 1-continued

| Ex. No. | IUPAC name | structural formula | salt | MS |
|---|---|---|---|---|
| 117 | N-(3-fluoro-5-(1-methyl-1H-pyrazol-4-yl)benzyl)-3-methyl-2-(tetrahydrofuran-3-yl)-3H-imidazo[4,5-c]pyridine-4-carboxamide | | | 435.2 |
| 118 | N-(3-cyano-2-fluoro-5-(6-methylpyridazin-4-yl)benzyl)-2-cyclopentyl-3-methyl-3H-imidazo[4,5-c]pyridine-4-carboxamide | | | 470.3 |
| 119 | 2-cyclopentyl-7-fluoro-N-(3-fluoro-5-(1-methyl-1H-pyrazol-4-yl)benzyl)-3H-imidazo[4,5-c]pyridine-4-carboxamide | | | 437.3 |
| 120 | 2-(cyclopentylmethyl)-N-(3-fluoro-5-(1-methyl-1H-pyrazol-4-yl)benzyl)-3-methyl-3H-imidazo[4,5-c]pyridine-4-carboxamide | | | 447.2 |

TABLE 1-continued

| Ex. No. | IUPAC name | structural formula | salt | MS |
|---|---|---|---|---|
| 121 | N-(3-cyano-5-(6-methylpyridazin-4-yl)benzyl)-2-cyclopentyl-3-methyl-3H-imidazo[4,5-c]pyridine-4-carboxamide | | | 452.2 |
| 122 | 2-benzyl-N-(3-fluoro-5-(1-methyl-1H-pyrazol-4-yl)benzyl)-3-methyl-3H-imidazo[4,5-c]pyridine-4-carboxamide | | | 455.2 |
| 123 | 3-benzyl-2-cyclopentyl-N-(3-fluoro-5-(1-methyl-1H-pyrazol-4-yl)benzyl)-3H-imidazo[4,5-c]pyridine-4-carboxamide | | | 509.3 |
| 124 | 2-cyclopentyl-N-(3-fluoro-5-(6-methylpyridazin-4-yl)benzyl)-3-methyl-3H-imidazo[4,5-c]pyridine-4-carboxamide | | | 445.3 |

TABLE 1-continued

| Ex. No. | IUPAC name | structural formula | salt | MS |
|---|---|---|---|---|
| 125 | 2-(cyclopropylmethyl)-N-(3-fluoro-5-(1-methyl-1H-pyrazol-4-yl)benzyl)-3-methyl-3H-imidazo[4,5-c]pyridine-4-carboxamide | | | 419.2 |
| 126 | 2-(cyclopropylmethyl)-N-(3-fluoro-5-(1-methyl-1H-pyrazol-4-yl)benzyl)-3H-imidazo[4,5-c]pyridine-4-carboxamide | | | 405.2 |
| 127 | (2-cyclopentyl-4-((3-fluoro-5-(1-methyl-1H-pyrazol-4-yl)benzyl)carbamoyl)-3H-imidazo[4,5-c]pyridin-3-yl)acetic acid | | | 477.3 |

TABLE 1-continued

| Ex. No. | IUPAC name | structural formula | salt | MS |
|---|---|---|---|---|
| 128 | 3-(2-amino-2-oxoethyl)-2-cyclopentyl-N-(3-fluoro-5-(1-methyl-1H-pyrazol-4-yl)benzyl)-3H-imidazo[4,5-c]pyridine-4-carboxamide | | | 476.3 |
| 129 | 2-cyclopentyl-N-(3-fluoro-5-(1-methyl-1H-pyrazol-4-yl)benzyl)-3-(2-(methylamino)-2-oxoethyl)-3H-imidazo[4,5-c]pyridine-4-carboxamide | | | 490.3 |
| 130 | 2-cyclopentyl-3-(2-(dimethylamino)-2-oxoethyl)-N-(3-fluoro-5-(1-methyl-1H-pyrazol-4-yl)benzyl)-3H-imidazo[4,5-c]pyridine-4-carboxamide | | | 504.3 |

TABLE 1-continued
| Ex. No. | IUPAC name | structural formula | salt | MS |
|---|---|---|---|---|
| 131 | 3-(cyanomethyl)-2-cyclopentyl-N-(3-fluoro-5-(1-methyl-1H-pyrazol-4-yl)benzyl)-3H-imidazo[4,5-c]pyridine-4-carboxamide | 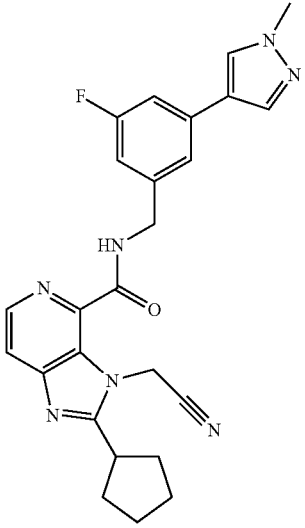 [SMILES: Cn1cc(-c2cc(F)cc(CNC(=O)c3nccc4nc(C5CCCC5)n(CC#N)c34)c2)cn1] | | 458.3 |
| 132 | 2-cyclopentyl-N-(3-fluoro-5-(1-methyl-6-oxo-1,6-dihydropyridin-3-yl)benzyl)-3H-imidazo[4,5-c]pyridine-4-carboxamide | 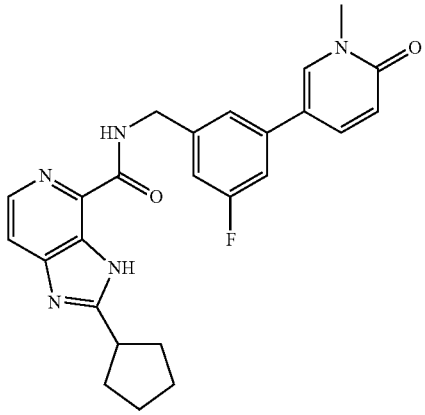 [SMILES: Cn1cc(-c2cc(F)cc(CNC(=O)c3nccc4nc(C5CCCC5)[nH]c34)c2)ccc1=O] | | 446.2 |
| 133 | N-(3-cyano-5-(1-methyl-1H-pyrazol-4-yl)benzyl)-3-methyl-2-(tetrahydrofuran-3-yl)-3H-imidazo[4,5-c]pyridine-4-carboxamide | 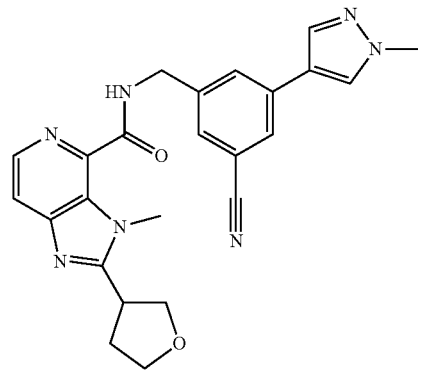 [SMILES: Cn1cc(-c2cc(C#N)cc(CNC(=O)c3nccc4nc(C5CCOC5)n(C)c34)c2)cn1] | | 442.2 |

TABLE 1-continued

| Ex. No. | IUPAC name | structural formula | salt | MS |
|---|---|---|---|---|
| 134 | 2-cyclopentyl-3-methyl-N-((6-(1-methyl-1H-pyrazol-4-yl)pyridin-2-yl)methyl)-3H-imidazo[4,5-c]pyridine-4-carboxamide | | | 416.3 |
| 135 | 2-cyclopentyl-3-methyl-N-((5-(1-methyl-1H-pyrazol-4-yl)pyridin-3-yl)methyl)-3H-imidazo[4,5-c]pyridine-4-carboxamide | | | 416.2 |
| 136 | 2-cyclopentyl-3-methyl-N-((2-(1-methyl-1H-pyrazol-4-yl)pyridin-4-yl)methyl)-3H-imidazo[4,5-c]pyridine-4-carboxamide | | | 416.2 |
| 137 | 2-cyclopentyl-N-(3-fluoro-5-(5-(hydroxymethyl)-1-methyl-1H-pyrazol-4-yl)benzyl)-3H-imidazo[4,5-c]pyridine-4-carboxamide | | | 449.2 |

TABLE 1-continued

| Ex. No. | IUPAC name | structural formula | salt | MS |
|---|---|---|---|---|
| 138 | 2-cyclopentyl-N-(3-(3,4-dimethyl-1H-pyrazol-1-yl)-5-fluorobenzyl)-3-methyl-3H-imidazo[4,5-c]pyridine-4-carboxamide | | | 447.2 |
| 139 | 2-cyclopentyl-3-methyl-N-((4-(1-methyl-1H-pyrazol-4-yl)pyridin-2-yl)methyl)-3H-imidazo[4,5-c]pyridine-4-carboxamide | | | 416.2 |
| 140 | 2-(3,3-difluorocyclopentyl)-N-(3-fluoro-5-(1-methyl-1H-pyrazol-4-yl)benzyl)-3-methyl-3H-imidazo[4,5-c]pyridine-4-carboxamide | | | 469.2 |
| 141 | 2-(3-fluorocyclopentyl)-N-(3-fluoro-5-(1-methyl-1H-pyrazol-4-yl)benzyl)-3H-imidazo[4,5-c]pyridine-4-carboxamide | | | 435.3 |

TABLE 1-continued

| Ex. No. | IUPAC name | structural formula | salt | MS |
|---|---|---|---|---|
| 142 | N-(3-cyano-5-(1-methyl-1H-pyrazol-4-yl)benzyl)-2-(3-fluorocyclopentyl)-3H-imidazo[4,5-c]pyridine-4-carboxamide | | | 442.2 |
| 143 | 2-(3,3-difluorocyclopentyl)-N-(3-fluoro-5-(1-methyl-1H-pyrazol-4-yl)benzyl)-3H-imidazo[4,5-c]pyridine-4-carboxamide | | | 455.2 |
| 144 | 3-(2-amino-2-oxoethyl)-2-(3,4-difluorocyclopentyl)-N-(3-fluoro-5-(1-methyl-1H-pyrazol-4-yl)benzyl)-3H-imidazo[4,5-c]pyridine-4-carboxamide | | | 512.2 |
| 145 | 2-(3,3-difluorocyclopentyl)-N-(3-fluoro-5-(1-methyl-1H-pyrazol-4-yl)benzyl)-3-(2-hydroxyethyl)-3H-imidazo[4,5-c]pyridine-4-carboxamide | | | 499.2 |

TABLE 1-continued

| Ex. No. | IUPAC name | structural formula | salt | MS |
|---|---|---|---|---|
| 146 | 2-cyclopentyl-3-methyl-N-((4-(1-methyl-1H-pyrazol-4-yl)pyrimidin-2-yl)methyl)-3H-imidazo[4,5-c]pyridine-4-carboxamide | | | 417.1 |
| 147 | 3-(2-amino-2-oxoethyl)-2-(3,3-difluorocyclopentyl)-N-(3-fluoro-5-(1-methyl-1H-pyrazol-4-yl)benzyl)-3H-imidazo[4,5-c]pyridine-4-carboxamide | | | 512.2 |
| 148 | 3-(2-amino-2-oxoethyl)-2-(3-fluorocyclopentyl)-N-(3-fluoro-5-(1-methyl-1H-pyrazol-4-yl)benzyl)-3H-imidazo[4,5-c]pyridine-4-carboxamide | | | 494.2 |
| 149 | 4-((3S)-3-cyano-3-cyclopropyl-2-oxopyrrolidin-1-yl)-N-(3-fluoro-5-(1-methyl-1H-pyrazol-4-yl)benzyl)pyridine-2-carboxamide | | | 459.3 |

TABLE 1-continued

| Ex. No. | IUPAC name | structural formula | salt | MS |
|---|---|---|---|---|
| 150 | 4-((3S)-3-cyano-3-cyclopropyl-2-oxopyrrolidin-1-yl)-N-(3-fluoro-5-(1-methyl-6-oxo-1,6-dihydropyridin-3-yl)benzyl)pyridine-2-carboxamide | | | 486.2 |
| 151 | 4-((3S)-3-cyano-3-cyclopropyl-2-oxopyrrolidin-1-yl)-N-(3-fluoro-5-(1-methyl-1H-1,2,3-triazol-4-yl)benzyl)pyridine-2-carboxamide | | | 460.3 |
| 152 | 4-((3S)-3-cyano-3-cyclopropyl-2-oxopyrrolidin-1-yl)-N-(3-fluoro-5-(1-isopropyl-1H-pyrazol-4-yl)benzyl)pyridine-2-carboxamide | | | 487.2 |

TABLE 1-continued

| Ex. No. | IUPAC name | structural formula | salt | MS |
|---|---|---|---|---|
| 154 | 4-((3S)-3-cyano-3-cyclopropyl-2-oxopyrrolidin-1-yl)-N-(3-(1-methyl-1H-pyrazol-4-yl)benzyl)pyridine-2-carboxamide | | | 441.2 |
| 155 | 4-((3S)-3-cyano-3-cyclopropyl-2-oxopyrrolidin-1-yl)-N-(3-(1-cyclopropyl-1H-pyrazol-4-yl)-5-fluorobenzyl)pyridine-2-carboxamide | | | 485.2 |
| 156 | 4-((3S)-3-cyano-3-cyclopropyl-2-oxopyrrolidin-1-yl)-N-((5-(1-methyl-1H-pyrazol-4-yl)-2-thienyl)methyl)-pyridine-2-carboxamide | | | 447.2 |
| 157 | 4-((3S)-3-cyano-3-cyclopropyl-2-oxopyrrolidin-1-yl)-N-((4-(1-methyl-1H-pyrazol-4-yl)-2-thienyl)methyl)-pyridine-2-carboxamide | | | 447.1 |

TABLE 1-continued

| Ex. No. | IUPAC name | structural formula | salt | MS |
|---|---|---|---|---|
| 158 | 4-(3,3-dimethyl-2-oxopyrrolidin-1-yl)-N-(3-fluoro-5-(1-methyl-1H-pyrazol-4-yl)benzyl)pyridine-2-carboxamide | | HCl | 422.2 |
| 159 | 4-((3S)-3-cyano-3-cyclopropyl-2-oxopyrrolidin-1-yl)-N-(3-fluoro-5-(1-methyl-1H-pyrazol-4-yl)benzyl)-6-methylpyridine-2-carboxamide | | | 473.2 |
| 160 | N-(3-fluoro-5-(1-methyl-1H-pyrazol-4-yl)benzyl)-4-(2-oxopyrrolidin-1-yl)pyridine-2-carboxamide | | | 394.2 |
| 161 | N-(3-fluoro-5-(1-methyl-1H-pyrazol-4-yl)benzyl)-4-(4-hydroxy-2-oxopyrrolidin-1-yl)pyridine-2-carboxamide | | | 410.2 |

TABLE 1-continued

| Ex. No. | IUPAC name | structural formula | salt | MS |
|---|---|---|---|---|
| 162 | 4-(3,3-dimethyl-2,4-dioxopyrrolidin-1-yl)-N-(3-fluoro-5-(1-methyl-1H-pyrazol-4-yl)benzyl)pyridine-2-carboxamide | | | 436.0 |
| 163 | N-(3-fluoro-5-(1-methyl-1H-pyrazol-4-yl)benzyl)-4-(4-hydroxy-3,3-dimethyl-2-oxopyrrolidin-1-yl)pyridine-2-carboxamide | | | 438.2 |
| 164 | 4-(3,3-diethyl-2-oxopyrrolidin-1-yl)-N-(3-fluoro-5-(1-methyl-1H-pyrazol-4-yl)benzyl)pyridine-2-carboxamide | | HCl | 450.2 |
| 165 | 4-(3,3-dimethyl-2-oxopyrrolidin-1-yl)-N-(3-fluoro-5-(1-methyl-1H-pyrazol-4-yl)benzyl)-6-methylpyridine-2-carboxamide | | HCl | 436.3 |

TABLE 1-continued

| Ex. No. | IUPAC name | structural formula | salt | MS |
|---|---|---|---|---|
| 166 | N-(3-fluoro-5-(1-methyl-1H-pyrazol-4-yl)benzyl)-4-(3-(hydroxymethyl)-2-oxopyrrolidin-1-yl)pyridine-2-carboxamide | | | 424.2 |
| 167 | 4-((3S)-3-cyano-3-cyclopropyl-2-oxopyrrolidin-1-yl)-N-(3-cyano-5-(1-methyl-1H-pyrazol-4-yl)benzyl)-6-methylpyridine-2-carboxamide | | | 480.3 |
| 168 | 4-((3S)-3-cyano-3-cyclopropyl-2-oxopyrrolidin-1-yl)-N-(3-(1-cyclopropyl-1H-pyrazol-4-yl)-5-fluorobenzyl)-6-methylpyridine-2-carboxamide | | | 499.3 |
| 169 | 4-((3S)-3-cyano-3-cyclopropyl-2-oxopyrrolidin-1-yl)-N-(3-fluoro-5-(1-methyl-6-oxo-1,6-dihydropyridin-3-yl)benzyl)-6-methylpyridine-2-carboxamide | | | 500.3 |

TABLE 1-continued

| Ex. No. | IUPAC name | structural formula | salt | MS |
|---|---|---|---|---|
| 170 | 4-((3S)-3-cyano-3-cyclopropyl-2-oxopyrrolidin-1-yl)-N-(3-fluoro-5-(2-methoxypyridin-4-yl)benzyl)-6-methylpyridine-2-carboxamide | | | 500.2 |
| 171 | 4-((3S)-3-cyano-3-cyclopropyl-2-oxopyrrolidin-1-yl)-N-(3-(1-(2,2-difluoroethyl)-1H-pyrazol-4-yl)-5-fluorobenzyl)-6-methylpyridine-2-carboxamide | | | 523.3 |
| 172 | 4-((3S)-3-cyano-3-cyclopropyl-2-oxopyrrolidin-1-yl)-N-(3-(1-(difluoromethyl)-1H-pyrazol-4-yl)-5-fluorobenzyl)-6-methylpyridine-2-carboxamide | | | 509.3 |

TABLE 1-continued

| Ex. No. | IUPAC name | structural formula | salt | MS |
|---|---|---|---|---|
| 173 | 4-((3S)-3-cyano-3-cyclopropyl-2-oxopyrrolidin-1-yl)-N-(3-fluoro-5-(1-(2,2,2-trifluoroethyl)-1H-pyrazol-4-yl)benzyl)-6-methylpyridine-2-carboxamide | | | 541.4 |
| 174 | 4-((3S)-3-cyano-3-cyclopropyl-2-oxopyrrolidin-1-yl)-N-(3-cyano-5-(1-cyclopropyl-1H-pyrazol-4-yl)benzyl)-6-methylpyridine-2-carboxamide | | | 506.3 |
| 175 | N-(3-(1-tert-butyl-1H-pyrazol-4-yl)-5-fluorobenzyl)-4-((3S)-3-cyano-3-cyclopropyl-2-oxopyrrolidin-1-yl)-6-methylpyridine-2-carboxamide | | | 515.3 |

TABLE 1-continued

| Ex. No. | IUPAC name | structural formula | salt | MS |
|---|---|---|---|---|
| 176 | N-(3-bromo-5-fluorobenzyl)-4-((3S)-3-cyano-3-cyclopropyl-2-oxopyrrolidin-1-yl)-6-methylpyridine-2-carboxamide | | | 471.1 |
| 177 | 4-((3S)-3-cyano-3-cyclopropyl-2-oxopyrrolidin-1-yl)-N-(3-(1,3-dimethyl-1H-pyrazol-4-yl)-5-fluorobenzyl)-6-methylpyridine-2-carboxamide | | | 487.3 |
| 178 | 4-((3S)-3-cyano-3-cyclopropyl-2-oxopyrrolidin-1-yl)-N-(3-(1,5-dimethyl-1H-pyrazol-4-yl)-5-fluorobenzyl)-6-methylpyridine-2-carboxamide | | | 487.3 |
| 179 | 4-(4,4-dimethyl-3-oxo-1,2-oxazolidin-2-yl)-N-(3-fluoro-5-(1-methyl-1H-pyrazol-4-yl)benzyl)-6-methylpyridine-2-carboxamide | | HCl | 438.2 |

TABLE 1-continued

| Ex. No. | IUPAC name | structural formula | salt | MS |
|---|---|---|---|---|
| 180 | 4-((3S)-3-cyano-3-cyclopropyl-2-oxopyrrolidin-1-yl)-N-(3-fluoro-5-(1-(2-hydroxy-2-methylpropyl)-1H-pyrazol-4-yl)benzyl)-6-methylpyridine-2-carboxamide | | | 531.3 |
| 181 | 4-((3S)-3-cyano-3-cyclopropyl-2-oxopyrrolidin-1-yl)-N-(3-fluoro-5-(1-(2-(morpholin-4-yl)ethyl)-1H-pyrazol-4-yl)benzyl)-6-methylpyridine-2-carboxamide | | | 572.4 |
| 182 | 4-((3S)-3-cyano-3-cyclopropyl-2-oxopyrrolidin-1-yl)-N-(3-fluoro-5-(1-(tetrahydro-2H-pyran-4-yl)-1H-pyrazol-4-yl)benzyl)-6-methylpyridine-2-carboxamide | | | 543.3 |
| 183 | 4-((3S)-3-cyano-3-cyclopropyl-2-oxopyrrolidin-1-yl)-N-(3-fluoro-5-(1-(tetrahydro-2H-pyran-2-yl)-1H-pyrazol-4-yl)benzyl)-6-methylpyridine-2-carboxamide | | | 543.3 |

TABLE 1-continued

| Ex. No. | IUPAC name | structural formula | salt | MS |
|---|---|---|---|---|
| 184 | 4-((3S)-3-cyano-3-cyclopropyl-2-oxopyrrolidin-1-yl)-N-(3-fluoro-5-(1-methyl-1H-pyrazol-3-yl)benzyl)-6-methylpyridine-2-carboxamide | | | 473.2 |
| 185 | 4-((3S)-3-cyano-3-cyclopropyl-2-oxopyrrolidin-1-yl)-N-(3-fluoro-5-(1-methyl-1H-pyrazol-5-yl)benzyl)-6-methylpyridine-2-carboxamide | | | 473.2 |
| 186 | 4-((3S)-3-cyano-3-cyclopropyl-2-oxopyrrolidin-1-yl)-N-(3-(1,3-dimethyl-1H-pyrazol-5-yl)-5-fluorobenzyl)-6-methylpyridine-2-carboxamide | | | 487.2 |
| 187 | 4-((3S)-3-cyano-3-cyclopropyl-2-oxopyrrolidin-1-yl)-N-(3-fluoro-5-(2-methyl-1,3-thiazol-5-yl)benzyl)-6-methylpyridine-2-carboxamide | | | 490.2 |

TABLE 1-continued

| Ex. No. | IUPAC name | structural formula | salt | MS |
|---|---|---|---|---|
| 188 | 4-((3S)-3-cyano-3-cyclopropyl-2-oxopyrrolidin-1-yl)-N-(3-(2,4-dimethyl-1,3-thiazol-5-yl)-5-fluorobenzyl)-6-methylpyridine-2-carboxamide | | | 504.2 |
| 189 | 4-((3S)-3-cyano-3-cyclopropyl-2-oxopyrrolidin-1-yl)-N-(3-fluoro-5-(6-methoxypyridin-2-yl)benzyl)-6-methylpyridine-2-carboxamide | | | 500.3 |
| 190 | 4-((3S)-3-cyano-3-cyclopropyl-2-oxopyrrolidin-1-yl)-N-(3-fluoro-5-(6-fluoropyridin-2-yl)benzyl)-6-methylpyridine-2-carboxamide | | | 488.2 |
| 191 | 4-((3S)-3-cyano-3-cyclopropyl-2-oxopyrrolidin-1-yl)-N-(3-fluoro-5-(4-methoxypyridin-2-yl)benzyl)-6-methylpyridine-2-carboxamide | | | 500.3 |

TABLE 1-continued

| Ex. No. | IUPAC name | structural formula | salt | MS |
|---|---|---|---|---|
| 192 | 4-((3S)-3-cyano-3-cyclopropyl-2-oxopyrrolidin-1-yl)-N-(3-fluoro-5-(pyridin-3-yl)benzyl)-6-methylpyridine-2-carboxamide | | | 470.2 |
| 193 | 4-((3S)-3-cyano-3-cyclopropyl-2-oxopyrrolidin-1-yl)-N-(3-fluoro-5-(2-methylpyridin-3-yl)benzyl)-6-methylpyridine-2-carboxamide | | | 484.3 |
| 194 | 4-((3S)-3-cyano-3-cyclopropyl-2-oxopyrrolidin-1-yl)-N-(3-fluoro-5-(2-fluoropyridin-3-yl)benzyl)-6-methylpyridine-2-carboxamide | | | 488.2 |
| 195 | 4-((3S)-3-cyano-3-cyclopropyl-2-oxopyrrolidin-1-yl)-N-(3-fluoro-5-(2-methoxypyridin-3-yl)benzyl)-6-methylpyridine-2-carboxamide | | | 500.3 |

TABLE 1-continued

| Ex. No. | IUPAC name | structural formula | salt | MS |
|---|---|---|---|---|
| 196 | 4-((3S)-3-cyano-3-cyclopropyl-2-oxopyrrolidin-1-yl)-N-(3-fluoro-5-(2-(trifluoromethyl)-pyridin-3-yl)benzyl)-6-methylpyridine-2-carboxamide | 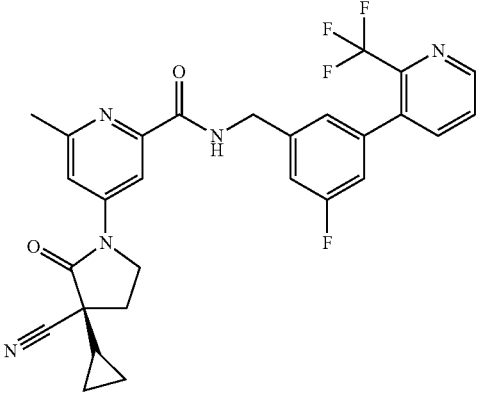 [SMILES: Cc1cc(N2CC[C@@](C#N)(C3CC3)C2=O)cc(C(=O)NCc2cc(F)cc(-c3cccnc3C(F)(F)F)c2)n1] | | 538.3 |
| 197 | 4-((3S)-3-cyano-3-cyclopropyl-2-oxopyrrolidin-1-yl)-N-(3-fluoro-5-(6-methylpyridin-3-yl)benzyl)-6-methylpyridine-2-carboxamide | 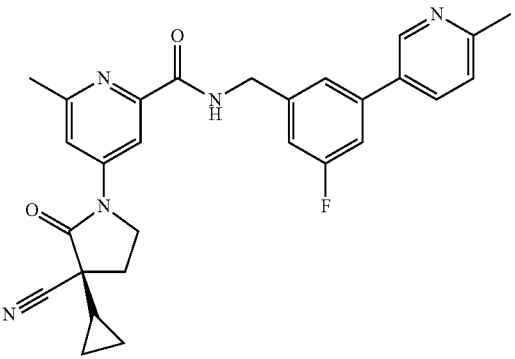 [SMILES: Cc1ccc(-c2cc(F)cc(CNC(=O)c3cc(N4CC[C@@](C#N)(C5CC5)C4=O)cc(C)n3)c2)cn1] | | 484.3 |
| 198 | 4-((3S)-3-cyano-3-cyclopropyl-2-oxopyrrolidin-1-yl)-N-(3-fluoro-5-(6-methoxypyridin-3-yl)benzyl)-6-methylpyridine-2-carboxamide | 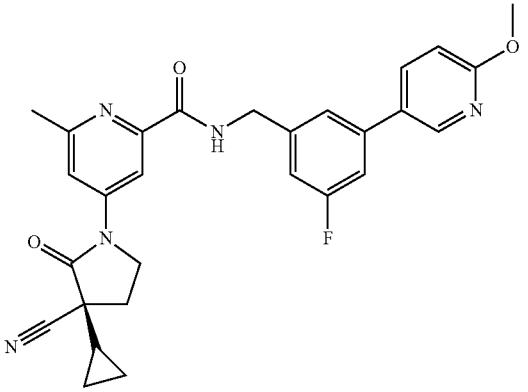 [SMILES: COc1ccc(-c2cc(F)cc(CNC(=O)c3cc(N4CC[C@@](C#N)(C5CC5)C4=O)cc(C)n3)c2)cn1] | | 500.3 |
| 199 | 4-((3S)-3-cyano-3-cyclopropyl-2-oxopyrrolidin-1-yl)-N-(3-fluoro-5-(6-fluoropyridin-3-yl)benzyl)-6-methylpyridine-2-carboxamide | 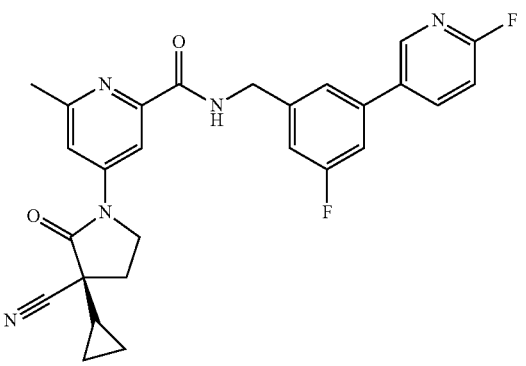 [SMILES: Cc1cc(N2CC[C@@](C#N)(C3CC3)C2=O)cc(C(=O)NCc2cc(F)cc(-c3ccc(F)nc3)c2)n1] | | 488.3 |

TABLE 1-continued

| Ex. No. | IUPAC name | structural formula | salt | MS |
|---|---|---|---|---|
| 200 | 4-((3S)-3-cyano-3-cyclopropyl-2-oxopyrrolidin-1-yl)-N-(3-fluoro-5-(5-methylpyridin-3-yl)benzyl)-6-methylpyridine-2-carboxamide | | | 484.3 |
| 201 | 4-((3S)-3-cyano-3-cyclopropyl-2-oxopyrrolidin-1-yl)-N-(3-fluoro-5-(5-fluoropyridin-3-yl)benzyl)-6-methylpyridine-2-carboxamide | | | 488.2 |
| 202 | 4-((3S)-3-cyano-3-cyclopropyl-2-oxopyrrolidin-1-yl)-N-(3-fluoro-5-(5-methoxypyridin-3-yl)benzyl)-6-methylpyridine-2-carboxamide | | | 500.3 |
| 203 | 4-((3S)-3-cyano-3-cyclopropyl-2-oxopyrrolidin-1-yl)-N-(3-fluoro-5-(4-methoxypyridin-3-yl)benzyl)-6-methylpyridine-2-carboxamide | | | 500.3 |

TABLE 1-continued

| Ex. No. | IUPAC name | structural formula | salt | MS |
|---|---|---|---|---|
| 204 | 4-((3S)-3-cyano-3-cyclopropyl-2-oxopyrrolidin-1-yl)-N-(3-fluoro-5-(6-fluoro-5-methylpyridin-3-yl)benzyl)-6-methylpyridine-2-carboxamide | 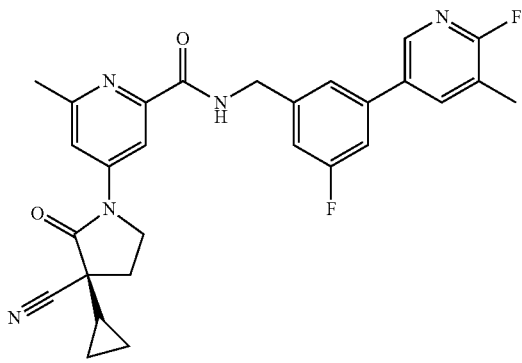 [SMILES: Cc1cc(N2CC[C@@](C#N)(C3CC3)C2=O)cc(C(=O)NCc2cc(F)cc(-c3cnc(F)c(C)c3)c2)n1] | | 502.2 |
| 205 | 4-((3S)-3-cyano-3-cyclopropyl-2-oxopyrrolidin-1-yl)-N-(3-fluoro-5-(pyrimidin-5-yl)benzyl)-6-methylpyridine-2-carboxamide | 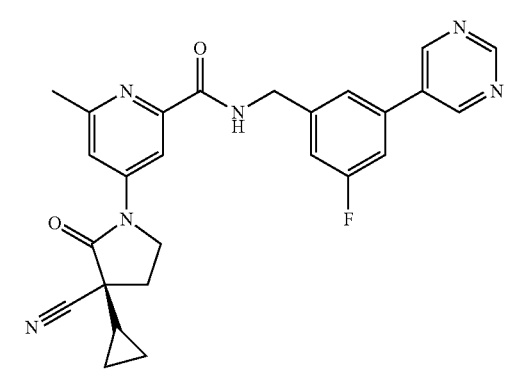 [SMILES: Cc1cc(N2CC[C@@](C#N)(C3CC3)C2=O)cc(C(=O)NCc2cc(F)cc(-c3cncnc3)c2)n1] | | 471.2 |
| 206 | 4-((3S)-3-cyano-3-cyclopropyl-2-oxopyrrolidin-1-yl)-N-(3-fluoro-5-(2-methoxypyrimidin-5-yl)benzyl)-6-methylpyridine-2-carboxamide | 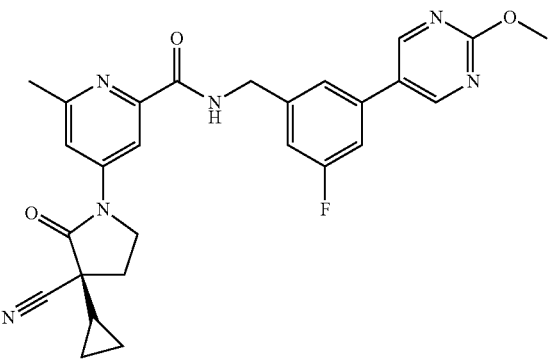 [SMILES: COc1ncc(-c2cc(F)cc(CNC(=O)c3cc(N4CC[C@@](C#N)(C5CC5)C4=O)cc(C)n3)c2)cn1] | | 501.3 |
| 207 | 4-((3S)-3-cyano-3-cyclopropyl-2-oxopyrrolidin-1-yl)-N-(3-fluoro-5-(6-methylpyridazin-4-yl)benzyl)-6-methylpyridine-2-carboxamide | 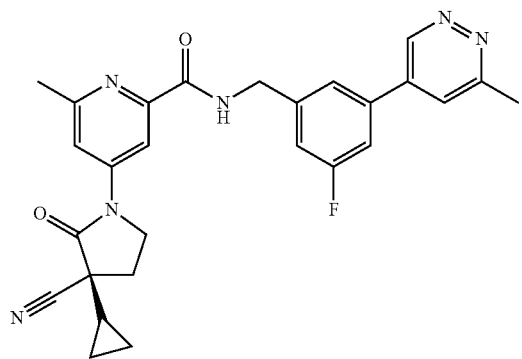 [SMILES: Cc1cc(-c2cc(F)cc(CNC(=O)c3cc(N4CC[C@@](C#N)(C5CC5)C4=O)cc(C)n3)c2)cnn1] | | 485.3 |

TABLE 1-continued

| Ex. No. | IUPAC name | structural formula | salt | MS |
|---|---|---|---|---|
| 208 | 4-((3S)-3-cyano-3-cyclopropyl-2-oxopyrrolidin-1-yl)-N-(3-fluoro-5-(pyridin-4-yl)benzyl)-6-methylpyridine-2-carboxamide | | | 470.2 |
| 209 | 4-((3S)-3-cyano-3-cyclopropyl-2-oxopyrrolidin-1-yl)-N-(3-fluoro-5-(2-methylpyridin-4-yl)benzyl)-6-methylpyridine-2-carboxamide | | | 484.3 |
| 210 | 4-((3S)-3-cyano-3-cyclopropyl-2-oxopyrrolidin-1-yl)-N-(3-fluoro-5-(3-methoxypyridin-4-yl)benzyl)-6-methylpyridine-2-carboxamide | | | 500.3 |
| 211 | 4-((3S)-3-cyano-3-cyclopropyl-2-oxopyrrolidin-1-yl)-N-(3-fluoro-5-(2-fluoropyridin-4-yl)benzyl)-6-methylpyridine-2-carboxamide | | | 488.2 |

TABLE 1-continued

| Ex. No. | IUPAC name | structural formula | salt | MS |
|---|---|---|---|---|
| 212 | 4-((3S)-3-cyano-3-cyclopropyl-2-oxopyrrolidin-1-yl)-N-(3-fluoro-5-(2-(trifluoromethyl)-pyridin-4-yl)benzyl)-6-methylpyridine-2-carboxamide | | | 538.3 |
| 213 | 4-((3S)-3-cyano-3-cyclopropyl-2-oxopyrrolidin-1-yl)-N-(3-fluoro-5-(1-methyl-2-oxo-1,2-dihydropyridin-4-yl)benzyl)-6-methylpyridine-2-carboxamide | | | 500.3 |
| 214 | 4-((3S)-3-cyano-3-cyclopropyl-2-oxopyrrolidin-1-yl)-6-(difluoromethyl)-N-(3-fluoro-5-(1-methyl-1H-pyrazol-4-yl)benzyl)pyridine-2-carboxamide | | | 509.2 |
| 215 | 4-((3S)-3-cyano-3-cyclopropyl-2-oxopyrrolidin-1-yl)-N-(3-cyano-5-(1-(difluoromethyl)-1H-pyrazol-4-yl)benzyl)-6-methylpyridine-2-carboxamide | | | 516.2 |

TABLE 1-continued

| Ex. No. | IUPAC name | structural formula | salt | MS |
|---|---|---|---|---|
| 216 | N-(3-chloro-5-(1-methyl-1H-pyrazol-4-yl)benzyl)-4-((3S)-3-cyano-3-cyclopropyl-2-oxopyrrolidin-1-yl)-6-methylpyridine-2-carboxamide | | | 489.2 |
| 217 | 4-((3S)-3-cyano-3-cyclopropyl-2-oxopyrrolidin-1-yl)-6-methyl-N-(3-methyl-5-(1-methyl-1H-pyrazol-4-yl)benzyl)pyridine-2-carboxamide | | | 469.2 |
| 218 | 4-((3S)-3-cyano-3-cyclopropyl-2-oxopyrrolidin-1-yl)-6-methyl-N-(3-(1-methyl-1H-pyrazol-4-yl)-5-(trifluoromethyl)benzyl)-pyridine-2-carboxamide | | | 523.1 |
| 219 | 4-((3S)-3-cyano-3-cyclopropyl-2-oxopyrrolidin-1-yl)-6-ethyl-N-(3-fluoro-5-(1-methyl-1H-pyrazol-4-yl)benzyl)pyridine-2-carboxamide | | | 487.2 |

TABLE 1-continued

| Ex. No. | IUPAC name | salt | MS |
|---|---|---|---|
| 220 | 4-((3S,5S)-3-cyano-3-cyclopropyl-5-methyl-2-oxopyrrolidin-1-yl)-N-(3-fluoro-5-(1-methyl-1H-pyrazol-4-yl)benzyl)pyridine-2-carboxamide | HCl | 473.2 |
| 221 | 4-((3S,5S)-3-cyano-3-cyclopropyl-5-methyl-2-oxopyrrolidin-1-yl)-N-(3-fluoro-5-(1-methyl-1H-pyrazol-4-yl)benzyl)-6-methylpyridine-2-carboxamide | HCl | 487.3 |
| 222 | tert-butyl 4-(3-((((4-((3S)-3-cyano-3-cyclopropyl-2-oxopyrrolidin-1-yl)-6-methylpyridin-2-yl)carbonyl)amino)methyl)-5-fluorophenyl)-1H-pyrazole-1-carboxylate | | 559.3 |
| 223 | 4-((3S)-3-cyano-3-cyclopropyl-2-oxopyrrolidin-1-yl)-N-(3-fluoro-5-(1H-pyrazol-4-yl)benzyl)-6-methylpyridine-2-carboxamide | | 459.3 |

TABLE 1-continued

| Ex. No. | IUPAC name | structural formula | salt | MS |
|---|---|---|---|---|
| 224 | 4-((3S)-3-cyano-3-cyclopropyl-2-oxopyrrolidin-1-yl)-N-(3-fluoro-5-(1-methyl-1H-pyrazol-4-yl)benzyl)-6-methoxypyridine-2-carboxamide | | | 489.2 |
| 225 | 4-((3S)-3-cyano-3-cyclopropyl-2-oxopyrrolidin-1-yl)-6-cyclopropyl-N-(3-fluoro-5-(1-methyl-1H-pyrazol-4-yl)benzyl)pyridine-2-carboxamide | | | 499.2 |
| 226 | N-(3-fluoro-5-(1-methyl-1H-pyrazol-4-yl)benzyl)-4-(3-isopropyl-2-oxoimidazolidin-1-yl)-6-methylpyridine-2-carboxamide | | | 451.2 |
| 227 | 4-((3S)-3-cyano-3-cyclopropyl-2-oxopyrrolidin-1-yl)-N-(3-(1H-imidazol-1-yl)benzyl)-6-methylpyridine-2-carboxamide | | | 441.2 |

TABLE 1-continued

| Ex. No. | IUPAC name | structural formula | salt | MS |
|---|---|---|---|---|
| 228 | 4-((3S)-3-cyano-3-cyclopropyl-2-oxopyrrolidin-1-yl)-N-(3-fluoro-5-(4-methyl-1H-imidazol-1-yl)benzyl)-6-methylpyridine-2-carboxamide | | | 473.2 |
| 229 | 4-(3-cyano-3-cyclobutyl-2-oxopyrrolidin-1-yl)-N-(3-fluoro-5-(1-methyl-1H-pyrazol-4-yl)benzyl)-6-methylpyridine-2-carboxamide | | CF$_3$COOH | 487.2 |
| 230 | 4-(3-cyano-3-(cyclopropylmethyl)-2-oxopyrrolidin-1-yl)-N-(3-fluoro-5-(1-methyl-1H-pyrazol-4-yl)benzyl)-6-methylpyridine-2-carboxamide | | CF$_3$COOH | 487.3 |
| 231 | 4-(3-tert-butyl-3-cyano-2-oxopyrrolidin-1-yl)-N-(3-fluoro-5-(1-methyl-1H-pyrazol-4-yl)benzyl)-6-methylpyridine-2-carboxamide | | | 489.2 |

TABLE 1-continued

| Ex. No. | IUPAC name | salt | MS |
|---|---|---|---|
| 232 | N-(3-fluoro-5-(1-methyl-1H-pyrazol-4-yl)benzyl)-6-methyl-4-(5-oxo-6-azaspiro[3.4]oct-6-yl)pyridine-2-carboxamide | | 448.2 |
| 233 | N-(3-fluoro-5-(1-methyl-1H-pyrazol-4-yl)benzyl)-6-methyl-4-(4-oxo-5-azaspiro[2.4]hept-5-yl)pyridine-2-carboxamide | | 434.2 |
| 234 | 4-(3-cyclopropyl-2-oxopyrrolidin-1-yl)-N-(3-fluoro-5-(1-methyl-1H-pyrazol-4-yl)benzyl)-6-methylpyridine-2-carboxamide | | 448.2 |
| 235 | 4-(3-cyclopropyl-3-(hydroxymethyl)-2-oxopyrrolidin-1-yl)-N-(3-fluoro-5-(1-methyl-1H-pyrazol-4-yl)benzyl)-6-methylpyridine-2-carboxamide | | 478.3 |
| 236 | 4-(3-cyano-3-(1-methylcyclopropyl)-2-oxopyrrolidin-1-yl)-N-(3-fluoro-5-(1-methyl-1H-pyrazol-4-yl)benzyl)-6-methylpyridine-2-carboxamide | CF₃COOH | 487.3 |

TABLE 1-continued

| Ex. No. | IUPAC name | structural formula | salt | MS |
|---|---|---|---|---|
| 237 | 6-((3S)-3-cyano-3-cyclopropyl-2-oxopyrrolidin-1-yl)-N-(3-fluoro-5-(1-methyl-1H-pyrazol-4-yl)benzyl)-2-methylpyrimidine-4-carboxamide | | | 474.1 |
| 238 | 4-((3S)-3-cyano-3-cyclopropyl-2-oxopyrrolidin-1-yl)-N-(3-fluoro-5-(1-methyl-1H-pyrazol-4-yl)benzyl)-6-methylpyrimidine-2-carboxamide | | | 474.3 |
| 239 | 4-((3S,5S)-3-cyano-3-cyclopropyl-5-methyl-2-oxopyrrolidin-1-yl)-N-(3-fluoro-5-(1-methyl-1H-pyrazol-4-yl)benzyl)-6-methylpyrimidine-2-carboxamide | | | 488.2 |
| 240 | 4-(3,3-dimethyl-2-oxopyrrolidin-1-yl)-N-(3-fluoro-5-(1-methyl-1H-pyrazol-4-yl)benzyl)-6-methylpyrimidine-2-carboxamide | | | 437.2 |

Experimental Example 1

The PRS inhibitory activity of the compounds of the present invention was evaluated by the following method.

An expression plasmid of Catalytic Domain of human EPRS was obtained by PCR using human skeletal muscle cDNA Library (Takara Bio Inc.) as a template and 2 kinds of Primers 5'-ATAATAGCTAGCGAGAACCTG-TACTTTCAGGGATCCTCAAGTGGAGCAGGA-GAAGGGCA-3' (hEPRS-TEV-NheF) (SEQ ID NO: 1) and 5'-ATAATAGCGGCCGCTCAGTAGCTGCGAC-CAAATAAGGT-3' (hEPRS-St-Not-R) (SEQ ID NO: 2). PCR was performed using PrimeStar GXL DNA Polymerase (Takara Bio Inc.) and included (1) 98° C., 1 min, (2) 35 cycles of 98° C., 10 sec, 65° C., 10 sec, 72° C., 1 min, and (3) reaction at 72° C., 1 min. This was cleaved with Nhe I and Not I (Takara Bio Inc.) and inserted using Ligation High (TOYOBO CO., LTD.) into the Nhe I/Not I site of pET21a (Novagen) with His-Avitag inserted thereinto. This was introduced into ECOS JM109 (NIPPON GENE CO., LTD.) to construct His-Avi-hEPRS (998-1512) expression plasmid.

Recombinant human PRS protein was prepared by transforming the His-Avi-hEPRS (998-1512) expression plasmid prepared above into ECOS Competent *E. coli* BL21(DE3) (NIPPON GENE CO., LTD.). *Escherichia coli* obtained by transformation was inoculated into 300 mL of LB medium (1% peptone, 0.5% yeast extract, 0.5% sodium chloride, 0.01% ampicillin) and cultured at 30° C. for 16 hr. The obtained culture medium was transferred into a jar culture tank charged with 6 L of the main fermentation medium (0.3% potassium dihydrogen phosphate, 0.6% disodium hydrogen phosphate, 0.1% ammonium chloride, 0.05% sodium chloride, 0.024% magnesium sulfate, 0.02% NEWPOL LB-625, 1.5% sorbitol, 1.5% casamino acid, 0.5% yeast extract, 0.01% ampicillin) and culturing was started at 37° C., quantity of airflow 5 L/min, stirring rotating speed 400 rpm. At the time point when the turbidity of the culture medium reached about 550 Klett units, the culture temperature was lowered to 16° C., isopropyl-β-D-thiogalactopyranoside (IPTG) was added to the final concentration 0.1 mM, and culturing was performed for another 16 hr to induce expression of human PRS. After completion of culturing, the culture medium was centrifuged at 5,000 rpm for 10 min. The obtained human PRS expressing *Escherichia coli* was suspended in a buffer containing 50 mM Tris-HCl (pH 8.0), 150 mM NaCl, 1 mM DTT, 5 U/ml Benzonase, 20 mM Imidazole and sonicated using Sonifier (BRANSON). The homogenate was centrifuged (33,000×G, 60 min, Beckman Coulter), the obtained supernatant was subjected to adsorption by passage through Ni-NTA Superflow (QIAGEN) column equilibrated in advance with 50 mM Tris-HCl (pH 8.0), 300 mM NaCl, 1 mM DTT, and elution was performed with a buffer containing 50 mM Tris-HCl (pH 8.0), 300 mM NaCl, 1 mM DTT, 250 mM Imidazole. Furthermore, gel filtration was performed using Superdex200 pg column equilibrated in advance with a buffer containing 50 mM Tris-HCl (pH 8.0), 150 mM NaCl, 1 mM DTT, 10% glycerol to give purified human PRS protein. The protein concentration was measured using BCA Protein Assay Kit (PIERCE) and BSA as the standard.

A test compound was dissolved in 5 μL of an assay buffer (50 mM Tris-HCl (pH 7.5), 20 mM KCl, 1 mM DTT, 0.01% Tween 20) and incubated for 60 min with 5 μL of 40 nM human PRS protein dissolved in the assay buffer containing 40 mM $MgCl_2$. An enzyme reaction of the human PRS protein was started by adding 10 μL of a substrate solution containing 300 μM ATP, 160 μM L-Proline, 400 μM pyrophosphate, [$^{32}$P]pyrophosphate (PerkinElmer) prepared to 1 MBq/mL. After incubation at room temperature for 30 min, the reaction was discontinued by adding 50 μL of discontinuation/washing solution (1M HCl, 200 mM sodium pyrophosphate) to the reaction mixture. The reaction solution was transferred to a filter plate (Merck Millipore, Billerica, Mass.) previously added with 200 μL of charcoal solution (0.5% HCl solution containing 10% charcoal (w/v)). The filter plate was washed 5 times with washing solution, the labeled resultant product was extracted into 96 well Opti-Plate (PerkinElmer) with an extraction liquid (60% ethanol (v/v) containing 2M ammonia) and microscinti 20 (PerkinElmer) was added. The radioactivity was measured using TopCount (PerkinElmer). The inhibitory rate (%) of the test compound was calculated with the radioactivity of a sample free of an enzyme reaction as 100% inhibition.

The inhibitory rate (%) of PRS with 300 nM test compound is shown in Table 2.

TABLE 2

| Example No. | inhibitory rate (%) |
| --- | --- |
| 1 | 98 |
| 2 | 101 |
| 3 | 101 |
| 4 | 101 |
| 5 | 102 |
| 6 | 79 |
| 7 | 102 |
| 10 | 97 |
| 11 | 102 |
| 12 | 77 |
| 13 | 86 |
| 14 | 100 |
| 16 | 102 |
| 18 | 99 |
| 21 | 92 |
| 23 | 102 |
| 24 | 96 |
| 27 | 99 |
| 28 | 101 |
| 30 | 102 |
| 31 | 102 |
| 32 | 101 |
| 33 | 99 |
| 34 | 101 |
| 40 | 102 |
| 42 | 98 |
| 45 | 101 |
| 52 | 99 |
| 56 | 102 |
| 58 | 99 |
| 63 | 102 |
| 71 | 100 |
| 81 | 97 |
| 82 | 98 |
| 83 | 98 |
| 84 | 100 |
| 85 | 97 |
| 86 | 101 |
| 87 | 74 |
| 88 | 101 |
| 89 | 101 |
| 90 | 101 |
| 91 | 101 |
| 92 | 100 |
| 93 | 91 |
| 94 | 97 |
| 95 | 99 |
| 96 | 101 |
| 97 | 101 |
| 98 | 101 |
| 99 | 96 |
| 101 | 102 |
| 103 | 99 |
| 104 | 98 |
| 106 | 99 |
| 108 | 102 |
| 109 | 100 |
| 113 | 101 |
| 114 | 101 |
| 115 | 101 |
| 117 | 100 |
| 123 | 69 |
| 126 | 98 |
| 127 | 101 |
| 128 | 102 |
| 131 | 101 |
| 136 | 77 |
| 146 | 78 |
| 149 | 95 |
| 150 | 87 |
| 157 | 85 |
| 159 | 101 |
| 165 | 100 |
| 167 | 99 |
| 168 | 100 |
| 169 | 100 |
| 179 | 93 |
| 182 | 101 |

TABLE 2-continued

| Example No. | inhibitory rate (%) |
|---|---|
| 187 | 99 |
| 205 | 86 |
| 207 | 96 |
| 209 | 100 |
| 214 | 99 |
| 216 | 101 |
| 217 | 101 |
| 218 | 83 |
| 219 | 94 |
| 221 | 99 |
| 224 | 74 |
| 225 | 66 |
| 226 | 91 |
| 228 | 100 |
| 229 | 100 |
| 230 | 91 |
| 232 | 100 |
| 233 | 100 |
| 234 | 87 |
| 235 | 69 |
| 237 | 74 |
| 238 | 101 |

From the results, it was clarified that the compound of the present invention has a PRS inhibitory activity.

Experimental Example 2

The proliferation inhibitory activity of the compound of the present invention against human ovarian cancer cell A2780 was evaluated by the following method.

Human ovarian cancer cells A2780 were seeded in a 384 well culture plate at 1000 cells in 30 μL of medium per well by using RPMI-1640 medium (Wako Pure Chemical Industries, Ltd.) containing 10% fetal bovine serum and penicillin/streptomycin. The next day, 10 μL of RPMI-1640 medium containing the test compound was added to the cells. After 3 days of culture, 20 μL of CellTiter-Glo Luminescent Cell Viability Assay solution (Promega) was added. The luminescence signal was measured using EnVision (PerkinElmer) and the inhibitory rate (%) of the test compound was calculated with a well free of seeding of cell as 100% inhibition.

The proliferation inhibitory rate (%) of A2780 cells by 1 μM test compound is shown in Table 3.

TABLE 3

| Example No. | inhibitory rate (%) |
|---|---|
| 1 | 60 |
| 2 | 97 |
| 3 | 99 |
| 4 | 99 |
| 5 | 98 |
| 7 | 95 |
| 10 | 55 |
| 11 | 95 |
| 14 | 97 |
| 16 | 93 |
| 18 | 77 |
| 23 | 69 |
| 24 | 57 |
| 27 | 97 |
| 30 | 99 |
| 31 | 97 |
| 32 | 76 |
| 40 | 98 |
| 42 | 59 |
| 45 | 99 |
| 52 | 69 |

TABLE 3-continued

| Example No. | inhibitory rate (%) |
|---|---|
| 56 | 99 |
| 58 | 66 |
| 63 | 98 |
| 71 | 70 |
| 81 | 56 |
| 84 | 97 |
| 86 | 97 |
| 88 | 99 |
| 89 | 98 |
| 90 | 96 |
| 91 | 98 |
| 92 | 99 |
| 94 | 64 |
| 95 | 56 |
| 96 | 95 |
| 97 | 98 |
| 98 | 98 |
| 101 | 98 |
| 103 | 73 |
| 104 | 68 |
| 106 | 84 |
| 109 | 84 |
| 113 | 99 |
| 115 | 94 |
| 117 | 78 |
| 126 | 56 |
| 127 | 70 |
| 128 | 97 |
| 131 | 93 |
| 159 | 96 |
| 165 | 75 |
| 167 | 98 |
| 168 | 98 |
| 169 | 98 |
| 182 | 97 |
| 187 | 65 |
| 207 | 59 |
| 209 | 80 |
| 214 | 72 |
| 216 | 89 |
| 217 | 80 |
| 221 | 64 |
| 228 | 88 |
| 229 | 91 |
| 232 | 64 |
| 233 | 70 |
| 238 | 95 |

From the results, it was clarified that the compound of the present invention suppresses proliferation of human ovarian cancer cell A2780.

Experimental Example 3

An antitumor action of the compound of the present invention on mice transplanted with human malignant melanoma cell line SKMEL-2 and human fibrosarcoma cell line HT-1080 was evaluated by the following method.

Human malignant melanoma cell line SKMEL-2 was subcutaneously transplanted by injection to 7-week-old BALB/cA Jcl-nu/nu female mice (CLEA Japan, Inc.) at $1.0 \times 10^7$ cells (G1). At the time point when the tumor volume reached around 800 mm$^3$ after transplantation, the cells were subcultured and transplanted into 7-week-old BALB/cA Jcl-nu/nu female mouse (CLEA Japan, Inc.) by using trocar (G2). Thereafter, in the same manner, at the time point when the tumor volume reached around 800 mm$^3$, the cells were subcultured and transplanted twice into 7-week-old BALB/cA Jcl-nu/nu female mouse (CLEA Japan, Inc.) (G4). Using trocar, SKMEL-2 tumor of G4 was transplanted into 7-week-old BALB/cA Jcl-nu/nu female mouse (CLEA Japan, Inc.). At 13 days from transplantation, the tumor diameter of the engrafted tumor was measured and the tumor volume was calculated by the following formula.

Human fibrosarcoma cell line HT-1080 was subcutaneously transplanted by injection into 7-week-old BALB/cA Jcl-nu/nu female mouse (CLEA Japan, Inc.) by $7.5 \times 10^6$ cells. At 8 days from transplantation, the tumor diameter of the engrafted tumor was measured and the tumor volume was calculated by the following formula.

tumor volume=major axis×minor axis×minor axis× (½)

Individuals having a tumor volume of 100 to 300 mm³ were selected for SKMEL-2, and individuals having a tumor volume of 200 to 400 mm³ were selected for HT-1080, and 4 or 5 mice per group were used for the experiment. A 0.5% methylcellulose suspension of the test compound was orally administered to the mice at the dose (dose per administration), administration frequency and dosing period shown in Table 3. The tumor diameter was measured one day before the start of administration and one day after completion of administration and the tumor volume was calculated.

The tumor proliferation rate (T/C (%)) of the test compound administration group in comparison with the control administration group was calculated by the following formula.

T/C (%)=(tumor volume of test compound administration group after completion of administration−tumor volume of test compound administration group before start of administration)/ (tumor volume of control administration group after completion of administration−tumor volume of control administration group before start of administration)×100

T/C (%) on mice transplanted with human malignant melanoma cell line SKMEL-2 and human fibrosarcoma cell line HT-1080 at each dose, administration frequency and dosing period of the test compound is shown in Table 4.

TABLE 4

| Example No. | T/C (%) | dose (mg/kg) | administration frequency, dosing period | cell line |
|---|---|---|---|---|
| 159 | 64 | 5 | administration once per day, 14 days | SKMEL-2 |
| 159 | 7.7 | 10 | administration once per day, 14 days | SKMEL-2 |

TABLE 4-continued

| Example No. | T/C (%) | dose (mg/kg) | administration frequency, dosing period | cell line |
|---|---|---|---|---|
| 32 | −8.2 | 10 | administration once per day, 11 days | HT-1080 |

From the results, it was clarified that the compound of the present invention shows an antitumor effect on human malignant melanoma cell line SKMEL-2 cell and human fibrosarcoma cell line HT-1080.

Formulation Example 1 (Production of Capsule)

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2 (Production of Tablets)

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The entire amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Ex. 1 per tablet are obtained.

INDUSTRIAL APPLICABILITY

The compound of the present invention may have a PRS inhibitory action and may be expected to be useful as a prophylactic or therapeutic agent for PRS associated diseases and the like including cancer.

This application is based on patent application No. 2016-180748 filed in Japan, the contents of which are encompassed in full herein.

The invention claimed is:

1. A compound represented by the following formula (I):

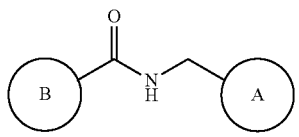

wherein a group represented by

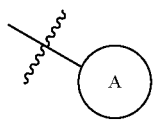

is an optionally substituted aromatic ring group; and
a group represented by

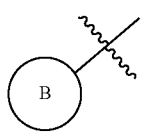

is a group represented by the following formula (III):

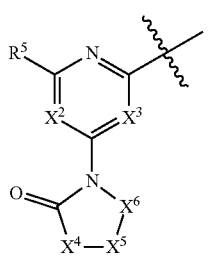

wherein
$R^5$ is a hydrogen atom, a halogen atom, a cyano group, an optionally substituted alkyl group, an optionally substituted cycloalkyl group, an optionally substituted alkenyl group, an optionally substituted alkynyl group, an optionally substituted amino group, or an optionally substituted hydroxy group;
$X^2$ is $CR^6$;
$X^3$ is $CR^7$;
$R^6$ and $R^7$ are each independently a hydrogen atom, a halogen atom, or an optionally substituted alkyl group;

$X^4$ is $CR^8R^9$ or $NR^{10}$, $X^5$ is $CR^{11}R^{12}$ or carbonyl, $X^6$ is $CR^{13}R^{14}$ or an oxygen atom;
$R^8$ and $R^9$ are each independently a hydrogen atom, a cyano group, an optionally substituted hydrocarbon group, or an optionally substituted heterocyclic group;
$R^8$ and $R^9$ are optionally bonded to each other to form, together with the adjacent carbon atom, an optionally further substituted ring;
$R^{10}$, $R^{13}$, and $R^{14}$ are each independently a hydrogen atom, an optionally substituted hydrocarbon group, or an optionally substituted heterocyclic group;
$R^{11}$ and $R^{12}$ are each independently a hydrogen atom, an optionally substituted hydrocarbon group, an optionally substituted heterocyclic group, or an optionally substituted hydroxy group;
or a pharmaceutically acceptable salt thereof.

2. The compound according to claim 1, wherein the group represented by

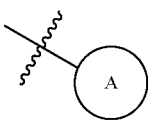

is a $C_{6-14}$ aryl group, a 5- or 6-membered monocyclic aromatic heterocyclic group or a 8 to 14-membered fused polycyclic aromatic heterocyclic group, each of which is optionally substituted by 1 to 5 substituents selected from the group consisting of:
(1) a halogen atom,
(2) a cyano group,
(3) a $C_{1-6}$ alkyl group optionally substituted by 1 to 3 halogen atoms,
(4) a $C_{6-14}$ aryl group,
(5) a $C_{1-6}$ alkoxy group,
(6) a carboxy group,
(7) a $C_{1-6}$ alkoxy-carbonyl group,
(8) a carbamoyl group optionally mono- or di-substituted by a 5- to 14-membered aromatic heterocyclic group optionally substituted by 1 to 3 $C_{1-6}$ alkyl groups, and
(9) a 5- to 14-membered aromatic heterocyclic group optionally substituted by 1 to 3 substituents selected from the group consisting of:
  (i) a cyano group,
  (ii) a $C_{1-6}$ alkyl group optionally substituted by 1 to 3 substituents selected from the group consisting of a halogen atom, a hydroxy group and a 3- to 14-membered non-aromatic heterocyclic group,
  (iii) a $C_{3-10}$ cycloalkyl group,
  (iv) a $C_{1-6}$ alkoxy group,
  (v) an oxo group,
  (vi) a $C_{1-6}$ alkoxy-carbonyl group, and
  (vii) a 3- to 14-membered non-aromatic heterocyclic group;

the group represented by

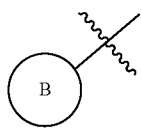

is a group represented by the following formula (III):

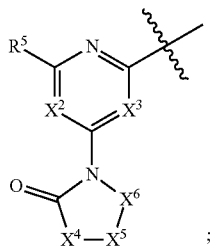

$R^5$ is a hydrogen atom, a $C_{1-6}$ alkyl group optionally substituted by 1 to 3 halogen atoms, a cycloalkyl group, or a hydroxy group optionally substituted by a $C_{1-6}$ alkyl group;
$X^2$ is $CR^6$ ($R^6$ is a hydrogen atom);
$X^3$ is $CR^7$ ($R^7$ is a hydrogen atom);
$X^4$ is $CR^8R^9$ or $NR^{10}$;

$R^8$ and $R^9$ are each independently selected from the group consisting of:
(1) a hydrogen atom,
(2) a cyano group,
(3) a $C_{1-6}$ alkyl group optionally substituted by 1 to 3 substituents selected from the group consisting of a hydroxy group and a $C_{3-10}$ cycloalkyl group, and
(4) a $C_{3-10}$ cycloalkyl group optionally substituted by 1 to 3 $C_{1-6}$ alkyl groups, or
$R^8$ and $R^9$ are bonded to each other to form $C_{3-10}$ cycloalkane together with the adjacent carbon atom;
$R^{10}$ is a $C_{1-6}$ alkyl group;
$X^5$ is $CR^{11}R^{12}$ ($R^{11}$ and $R^{12}$ are each independently a hydrogen atom or a hydroxy group) or a carbonyl; and
$X^6$ is $CR^{13}R^{14}$ ($R^{13}$ and $R^{14}$ are each independently a hydrogen atom or a $C_{1-6}$ alkyl group) or an oxygen atom;
or a pharmaceutically acceptable salt thereof.

3. A pharmaceutical composition comprising the compound according to claim 1 or a pharmaceutically acceptable salt thereof and a pharmacologically acceptable carrier.

4. A method for inhibiting PRS in a mammal, comprising administering an effective amount of the compound according to claim 1 or a pharmaceutically acceptable salt thereof to the mammal.

5. A method for treating ovarian or skin cancer in a mammal, comprising administering an effective amount of the compound according to claim 1 or a pharmaceutically acceptable salt thereof to the mammal.

* * * * *

SEQUENCE LISTING

```
<160> NUMBER OF SEQ ID NOS: 2

<210> SEQ ID NO 1
<211> LENGTH: 59
<212> TYPE: DNA
<213> ORGANISM: Artificial Sequence
<220> FEATURE:
<223> OTHER INFORMATION: PCR primer

<400> SEQUENCE: 1
ataatagcta gcgagaacct gtactttcag ggatcctcaa gtggagcagg agaagggca      59

<210> SEQ ID NO 2
<211> LENGTH: 38
```

```
<212> TYPE: DNA
<213> ORGANISM: Artificial Sequence
<220> FEATURE:
<223> OTHER INFORMATION: PCR primer

<400> SEQUENCE: 2
ataatagcgg ccgctcagta gctgcgacca aataaggt                           38
```